(12) United States Patent
Chassaing et al.

(10) Patent No.: US 8,507,474 B2
(45) Date of Patent: Aug. 13, 2013

(54) ANTHELMINTIC AGENTS AND THEIR USE

(75) Inventors: Christophe Pierre Alain Chassaing, Schwabenheim (DE); Thorsten Meyer, Schwabenheim (DE)

(73) Assignee: Intervet International B.V., Boxmeer (NL)

( * ) Notice: Subject to any disclaimer, the term of this patent is extended or adjusted under 35 U.S.C. 154(b) by 0 days.

(21) Appl. No.: 13/378,377

(22) PCT Filed: Jun. 16, 2010

(86) PCT No.: PCT/EP2010/058462
§ 371 (c)(1),
(2), (4) Date: Dec. 15, 2011

(87) PCT Pub. No.: WO2010/146083
PCT Pub. Date: Dec. 23, 2010

(65) Prior Publication Data
US 2012/0094981 A1  Apr. 19, 2012

Related U.S. Application Data

(60) Provisional application No. 61/218,269, filed on Jun. 18, 2009.

(30) Foreign Application Priority Data

Jun. 18, 2009 (EP) ..................... 09163036

(51) Int. Cl.
| | |
|---|---|
| *C07D 213/04* | (2006.01) |
| *C07D 213/84* | (2006.01) |
| *C07D 285/125* | (2006.01) |
| *C07D 401/04* | (2006.01) |
| *C07D 401/12* | (2006.01) |
| *C07D 417/04* | (2006.01) |
| *A61K 31/551* | (2006.01) |
| *A61K 31/496* | (2006.01) |
| *A61K 31/4545* | (2006.01) |
| *A61P 33/10* | (2006.01) |

(52) U.S. Cl.
USPC ................ 514/218; 514/253.01; 514/253.12; 514/254.03; 514/318; 540/575; 544/360; 544/367; 546/194

(58) Field of Classification Search
None
See application file for complete search history.

(56) References Cited

U.S. PATENT DOCUMENTS
2002/0142969 A1  10/2002  Jeschke et al.

FOREIGN PATENT DOCUMENTS
| | | |
|---|---|---|
| EP | 0 293 078 A1 | 11/1988 |
| WO | WO 2004/002943 A1 | 1/2004 |
| WO | WO 2008/011130 A2 | 1/2008 |

OTHER PUBLICATIONS

Liu et al., caplus an 2009:886309.*
Database Chemcats [Online] Chemical Abstract Service, Columbus Ohio, US; Feb. 9, 2009, XP002581103 retrieved from STN Database Accession No. 2048484683 *abstract* & "Aurora Screening Library" Feb. 9, 2009, Aurora Fine Chemicals LLC, San Diego, CA, 92125, US.

* cited by examiner

*Primary Examiner* — Sun Jae Loewe

(57) ABSTRACT

This invention is directed to compounds of the formula (I) and salts therefore that are generally useful as anthelmintic agents or as intermediates in processes for making anthelmintic agents. This invention also is directed to processes for making the compounds of this invention, pharmaceutical compositions and kits comprising the compounds of this invention, uses of the compounds of this invention to make medicaments, and treatments comprising the administration of the compounds of this invention to animals in need of the treatments.

10 Claims, No Drawings

ANTHELMINTIC AGENTS AND THEIR USE

FIELD OF THE INVENTION

This invention relates to compounds (and salts thereof) that are generally useful as anthelmintic agents or as intermediates in processes for making anthelmintic agents. This invention also relates to processes for making the compounds (and salts thereof) and intermediates of said preparation processes. Moreover this invention relates to pharmaceutical compositions and kits comprising the compounds (and salts thereof), uses of the compounds (and salts thereof) to make medicaments, and treatments comprising the administration of the compounds (and salts thereof) to animals in need of the treatments.

BACKGROUND OF THE INVENTION

Parasitic diseases in humans and animals cause substantial suffering and economic losses throughout the world. Thus, control of parasitic infections remains an important global endeavor. The causative organisms include helminths, such as nematodes, cestodes, and trematodes. These organisms can infect, for example, the stomach, intestinal tract, lymphatic system, tissues, liver, lungs, heart, and brain.

There are many known drugs (or "anthelmintic agents") available to treat various anthelminitc infections. These reportedly include, for example, various avermectins (e.g., ivermectin, selamectin, doramectin, abamectin, and eprinomectin); milbemycins (moxidectin and milbemycin oxime); pro-benzimidazoles (e.g., febantel, netobimin, and thiophanate); thiazole benzimidazole derivatives (e.g., thiabendazole and cambendazole); carbamate benzimidazole derivatives (e.g., fenbendazole, albendazole (oxide), mebendazole, oxfendazole, parbendazole, oxibendazole, flubendazole, and triclabendazole); imidazothiazoles (e.g., levamisole and tetramisole); tetrahydropyrimidine (morantel and pyrantel), organophosphates (e.g., trichlorphon, haloxon, dichlorvos, and naphthalophos); salicylanilides (e.g., closantel, oxyclozanide, rafoxanide, and niclosamide); nitrophenolic compounds (e.g., nitroxynil and nitroscanate); benzoenedisulphonamides (e.g., clorsulon); pyrazinaisoquinoline (e.g., praziquantel and epsiprantel); heterocyclic compounds (e.g., piperazine, diethylcarbamazine, dichlorophen, and phenothiazine); arsenicals (e.g., thiacetarsamide, melorsamine, and arsenamide); cyclooctadepsipeptides (e.g., emodepside); and paraherquamides. See, e.g., McKellar, Q. A., et al., "Veterinary anthelmintics: old and new," *Review: Trends in Parasitology*, 20(10), 456-61 (October 2004).

While many parasitic infections can be treated with known drugs, evolutionary development of resistance by the parasites can render such drugs obsolete over time. See, e.g., Jabbar, A., et al., "Anthelmintic resistance: the state of play revisited," *Life Sciences*, 79, 2413-31 (2006). In addition, known drugs may have other deficiencies, such as limited spectrum of activity and the need for repeated treatments. Thus, there still exists a need for new anthelmintic agents to ensure safe, effective, and convenient treatment of a wide range of endoparasitic infections over a long period of time. The following disclosure describes a group of such agents, as well as methods for making and using them.

SUMMARY OF THE INVENTION

Briefly, this invention relates to compounds (and salts thereof) that can generally be used as anthelmintic agents. The compounds correspond in structure to Formula I:

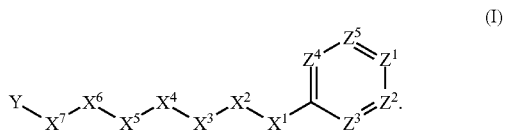

In Formula (I), $X^1$ is selected from the group consisting of —O—, —C(O)—, —S—, —S(O)—, —S(O)$_2$—, and —NH—. The —NH— is optionally substituted with a substituent selected from the group consisting of alkyl, alkenyl, alkynyl, alkoxyalkyl, carbocyclyl, and carbocyclylalkyl. Any such substituent is optionally substituted with one or more independently selected halogen. Preferably $X^1$ is selected from the group consisting of —O— and —NH—. The —NH— is optionally substituted with a substituent selected from the group consisting of alkyl.

$X^2$ is selected from the group consisting of straight-chain $C_3$-$C_5$-alkyl, straight-chain $C_3$-$C_5$-alkenyl, straight-chain $C_3$-$C_5$-alkynyl, and $C_4$-$C_6$-carbocyclyl. The straight-chain $C_3$-$C_5$-alkyl, straight-chain $C_3$-$C_5$-alkenyl, straight-chain $C_3$-$C_5$-alkynyl, and $C_4$-$C_6$-carbocyclyl are optionally substituted with one or more independently selected alkyl.

$X^3$ is selected from the group consisting of —CH$_2$—, —O—, —C(O)—, —S—, —S(O)—, —S(O)$_2$—, and —NH—. The —CH$_2$— is optionally substituted with up to two substituents independently selected from the group consisting of alkyl and carbocyclyl. The —NH— is optionally substituted with a substituent selected from the group consisting of alkyl, alkenyl, alkynyl, alkoxyalkyl, carbocyclyl, and carbocyclylalkyl. Any such substituent of —CH$_2$— and —NH— is optionally substituted with one or more independently selected halogen. Preferably $X^3$ is —O—.

$X^4$ is selected from the group consisting of —CH$_2$— and —NH—. The —CH$_2$— is optionally substituted with up to two substituents independently selected from the group consisting of alkyl, haloalkyl, and alkenyl. The —NH— is optionally substituted with a substituent selected from the group consisting of alkyl, alkenyl, alkynyl, alkoxy alkyl, carbocyclyl, and carbocyclylalkyl. Any such substituent of —NH— is optionally substituted with one or more independently selected halogen. Preferably $X^4$ is —CH$_2$—. The —CH$_2$— is optionally substituted with up to two substituents independently selected from the group consisting of alkyl, haloalkyl, and alkenyl.

$X^5$ is selected from the group consisting of —CH$_2$—, —O—, —C(S)—, —C(O)—, —S(O)—, and —S(O)$_2$—. The —CH$_2$— is optionally substituted with up to two substituents independently selected from the group consisting of alkyl and carbocyclyl. Preferably $X^5$ is selected from the group consisting of —C(S)— and —C(O)—.

$X^6$ is a linker. The linker is a hydrocarbon group, except: (a) the linker comprises one or more nitrogen atoms, and (b) one or more of the carbons in the hydrocarbon optionally are substituted with one or more substituents independently selected from the group consisting of oxo, thiocarbonyl, halogen, hydroxy, and alkoxy. The linker comprises at least one chain of from 3 to 6 atoms that bridges $X^5$ to $X^7$. From 1 to 2 of the chain atoms are nitrogen, preferably the linker binds via one of said nitrogen chain atoms to $X^5$.

$X^7$ is selected from the group consisting of a bond, —O—, —C(O)—, —NH—, —S—, —S(O)—, —S(O)$_2$—, —CH$_2$—, —CH$_2$CH$_2$—, —C(O)—CH$_2$—, —CH$_2$—C(O)—, —O—CH$_2$—, —CH$_2$—O—, —NH—CH$_2$—, —CH$_2$—NH—, —S—CH$_2$—, —CH$_2$—S—, —S(O)—CH$_2$—, —CH$_2$—S(O)—, —S(O)$_2$—CH$_2$—, and —CH$_2$—S $(O)_2$—. The —NH— is optionally substituted with alkyl. The —$CH_2$—, —$CH_2CH_2$—, —$C(O)$—$CH_2$—, —$CH_2$—$C(O)$—, —O—$CH_2$—, —$CH_2$—O—, —NH—$CH_2$—, —$CH_2$—NH—, —S—$CH_2$—, —$CH_2$—S—, —$S(O)$—$CH_2$—, —$CH_2$—$S(O)$—, —$S(O)_2$—$CH_2$—, and —$CH_2$—$S(O)_2$— are optionally substituted with one or more independently selected alkyl. Preferably $X^7$ is selected from the group consisting of a bond or —NH—, optionally substituted with alkyl.

Y is a 5-membered or 6-membered heteroaryl group. The heteroaryl group is optionally substituted with one or more substituents independently selected from the group consisting of halogen, cyano, OH, alkyl, alkoxy, nitro, aminosulfonyl, alkoxycarbonyl, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl. The alkyl, alkoxy, aminosulfonyl, alkoxycarbonyl, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl are optionally substituted with one or more substituents independently selected from the group consisting of halogen, cyano, alkyl, alkoxy, haloalkyl, haloalkoxy, alkylsulfanyl, and haloalkylsulfanyl.

$Z^1$ is selected from the group consisting of N and CH, preferably CH. The CH is preferably substituted with a substituent selected from the group consisting of halogen, nitro, cyano, amino sulfonyl, alkyl, alkoxy, alkoxycarbonyl, alkylsulfanyl, alkylsulfinyl, alkylsulfonyl, aryl, arylsulfanyl, arylsulfinyl, arylsulfonyl, heteroaryl, heteroarylsulfanyl, heteroarylsulfinyl, and heteroarylsulfonyl. The alkyl, alkoxy, alkoxycarbonyl, alkylsulfanyl, alkylsulfinyl, alkylsulfonyl, alkylsulfanyl, aryl, arylsulfanyl, arylsulfinyl, arylsulfonyl, heteroaryl, heteroarylsulfanyl, heteroarylsulfinyl, and heteroarylsulfonyl are optionally substituted with one or more substituents independently selected from the group consisting of halogen and alkyl; and the aminosulfonyl is optionally substituted with up to two independently selected alkyl.

$Z^2$ is selected from the group consisting of N and CH, preferably CH. The CH is preferably substituted with a substituent selected from the group consisting of cyano, halogen, nitro, alkyl, alkoxy, haloalkyl, and haloalkylsulfanyl.

Each of $Z^3$, $Z^4$, and $Z^5$ is independently selected from the group consisting of N and CH. The CH is optionally substituted with a substituent selected from the group consisting of halogen, cyano, nitro, alkyl, alkoxy, alkylsulfanyl, haloalkyl, haloalkoxy, and haloalkylsulfanyl.

In a preferred compound of Formula (I)

$X^1$ is selected from the group consisting of —O—, —S—, —$S(O)$—, —$S(O)_2$—, and —NH—. The —NH— is optionally substituted with a substituent selected from the group consisting of alkyl and alkoxyalkyl. Any such substituent is optionally substituted with one or more independently selected halogen.

$X^2$ is selected from the group consisting of straight-chain $C_3$-$C_5$-alkyl, straight-chain $C_3$-$C_5$-alkenyl, straight-chain $C_3$-$C_5$-alkynyl, and $C_4$-$C_6$-carbocyclyl. The straight-chain $C_3$-$C_5$-alkyl, straight-chain $C_3$-$C_5$-alkenyl, straight-chain $C_3$-$C_5$-alkynyl, and $C_4$-$C_6$-carbocyclyl are optionally substituted with one or more independently selected alkyl.

$X^3$ is selected from the group consisting of —$CH_2$—, —O—, —$C(O)$—, —S—, —$S(O)$—, —$S(O)_2$—, and —NH—. The —$CH_2$— is optionally substituted with up to two substituents independently selected from the group consisting of alkyl and carbocyclyl. The —NH— is optionally substituted with a substituent selected from the group consisting of alkyl and alkoxyalkyl. Any such substituent of —NH— is optionally substituted with one or more independently selected halogen. Preferably $X^3$ is —O—.

$X^4$ is selected from the group consisting of —$CH_2$— and —NH—. The —$CH_2$— is optionally substituted with up to two substituents independently selected from the group consisting of alkyl, haloalkyl and alkenyl. The —NH— is optionally substituted with a substituent selected from the group consisting of alkyl, alkenyl, alkynyl, alkoxy alkyl, carbocyclyl, and carbocyclylalkyl. Any such substituent of —NH— is optionally substituted with one or more independently selected halogen. Preferably $X^4$ is —$CH_2$—. The —$CH_2$— is optionally substituted with up to two substituents independently selected from the group consisting of alkyl, haloalkyl, and alkenyl.

$X^5$ is selected from the group consisting of —$CH_2$—, —O—, —$C(S)$—, —$C(O)$—. The —$CH_2$— is optionally substituted with up to two substituents independently selected from the group consisting of alkyl and carbocyclyl. Preferably $X^5$ is selected from the group consisting of —$C(S)$— and —$C(O)$—.

$X^6$ is a linker. The linker is a hydrocarbon group, except: (a) the linker comprises one or more nitrogen atoms, and (b) one or more of the carbons in the hydrocarbon optionally are substituted with one or more substituents independently selected from the group consisting of oxo, thiocarbonyl, halogen, hydroxy, and alkoxy. The linker comprises at least one chain of from 3 to 6 atoms that bridges $X^5$ to $X^7$. From 1 to 2 of the chain atoms are nitrogen. Preferably, the linker binds via one of said nitrogen chain atoms to $X^5$, and has no chain of less than 3 atoms that bridges $X^5$ and $X^7$.

$X^7$ is selected from the group consisting of a bond, —O—, —$C(O)$—, —NH—, —S—, —$S(O)$—, —$S(O)_2$—, —$CH_2$—, —$CH_2CH_2$—, —$C(O)$—$CH_2$—, —$CH_2$—$C(O)$—, —O—$CH_2$—, —$CH_2$—O—, —NH—$CH_2$—, —$CH_2$—NH—, —S—$CH_2$—, —$CH_2$—S—, —$S(O)$—$CH_2$—, —$CH_2$—$S(O)$—, —$S(O)_2$—$CH_2$—, and —$CH_2$—$S(O)_2$—. The —NH— is optionally substituted with alkyl. The —$CH_2$—, —$CH_2CH_2$—, —$C(O)$—$CH_2$—, —$CH_2$—$C(O)$—, —O—$CH_2$—, —$CH_2$—O—, —NH—$CH_2$—, —$CH_2$—NH—, —S—$CH_2$—, —$CH_2$—S—, —$S(O)$—$CH_2$—, —$CH_2$—$S(O)$—, —$S(O)_2$—$CH_2$—, and —$CH_2$—$S(O)_2$— are optionally substituted with one or more independently selected alkyl. Preferably $X^7$ is selected from the group consisting of a bond or —NH—, optionally substituted with alkyl.

Y is a 5-membered or 6-membered heteroaryl group, preferably containing one, two, three or four nitrogen ring atoms. The heteroaryl group is optionally substituted with one or more substituents independently selected from the group consisting of halogen, cyano, OH, alkyl, alkoxy, nitro, aminosulfonyl, alkoxycarbonyl, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl. The alkyl, alkoxy, aminosulfonyl, alkoxycarbonyl, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl are optionally substituted with one or more substituents independently selected from the group consisting of halogen, cyano, alkyl, alkoxy, haloalkyl, haloalkoxy, alkylsulfanyl, and haloalkylsulfanyl.

$Z^1$ is selected from the group consisting of N and CH, preferably CH. The CH is preferably substituted with a substituent selected from the group consisting of halogen, nitro, cyano, amino sulfonyl, alkyl, alkoxy, alkoxycarbonyl, alkylsulfanyl, alkylsulfinyl, alkylsulfonyl, arylsulfanyl, arylsulfinyl, arylsulfonyl, heteroaryl, heteroarylsulfanyl, heteroarylsulfinyl, and heteroarylsulfonyl. The alkyl, alkoxy, alkoxycarbonyl, alkylsulfanyl, alkylsulfinyl, alkylsulfonyl, alkylsulfanyl, aryl, arylsulfanyl, arylsulfinyl, arylsulfonyl, heteroaryl, heteroarylsulfanyl, heteroarylsulfinyl, and heteroarylsulfonyl are optionally substituted with one or more substituents independently selected from the group consisting of halogen and alkyl, preferably the substituents are fluorine; and the aminosulfonyl is optionally substituted with up to two independently selected alkyl.

$Z^2$ is selected from the group consisting of N and CH, preferably CH. The CH is preferably substituted with a substituent selected from the group consisting of cyano, halogen, nitro, alkyl, alkoxy, haloalkyl, and haloalkylsulfanyl, preferably with a haloalkyl-substituent such as fluoroalkyl, more preferably difluoromethyl and trifluoromethyl.

Each of $Z^3$, $Z^4$, and $Z^5$ is independently selected from the group consisting of N and CH, preferably CH. The CH is optionally substituted with a substituent selected from the group consisting of halogen, cyano, nitro, alkyl, alkoxy, alkylsulfanyl, haloalkyl, haloalkoxy, and haloalkylsulfanyl.

In a more preferred compound of Formula (I), $X^1$ is selected from the group consisting of —O—, —S—, and —NH—. The —NH— is optionally substituted with a substituent selected from the group consisting of alkyl and alkoxyalkyl. Any such substituent is optionally substituted with one or more independently selected halogen.

$X^2$ is selected from the group consisting of straight-chain $C_3$-$C_5$-alkyl, and $C_4$-$C_6$-carbocyclyl. The straight-chain $C_3$-$C_5$-alkyl, and $C_4$-$C_6$-carbocyclyl are optionally substituted with one or more independently selected alkyl.

$X^3$ is selected from the group consisting of —CH$_2$—, —O—, —C(O)—, and —NH—. The —CH$_2$— is optionally substituted with up to two substituents independently selected from the group consisting of alkyl and carbocyclyl. The —NH— is optionally substituted with a substituent selected from the group consisting of alkyl and alkoxyalkyl. Any such substituent of —NH— is optionally substituted with one or more independently selected halogen. Preferably $X^3$ is —O—.

$X^4$ is selected from the group consisting of —CH$_2$— and —NH—, preferably —CH$_2$—. The —CH$_2$— is optionally substituted with up to two substituents independently selected from the group consisting of alkyl, haloalkyl and alkenyl. The —NH— is optionally substituted with a substituent selected from the group consisting of alkyl, alkenyl, alkynyl, alkoxyalkyl.

$X^5$ is selected from the group consisting of —C(S)—, and —C(O)—.

$X^6$ is a linker selected from the group consisting of

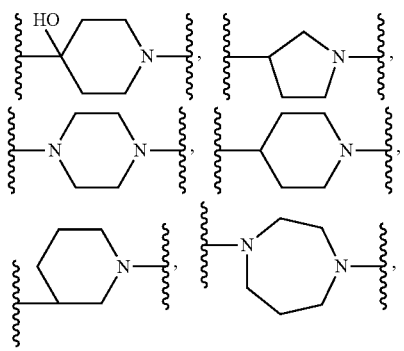

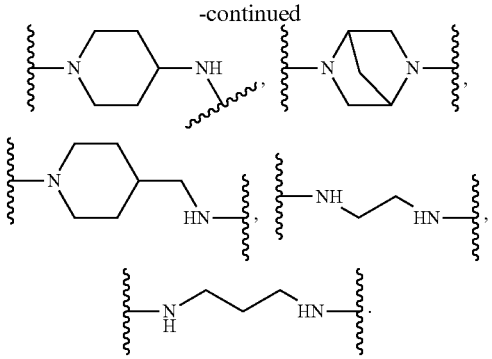

Any such group is optionally substituted with one or more substituents independently selected from the group consisting of halogen, $C_1$-$C_6$-alkyl, hydroxy, $C_1$-$C_6$-alkoxy, oxo, and thio carbonyl.

$X^7$ is selected from the group consisting of a bond, —O—, —NH—, —S—, —CH$_2$—. The —NH— is optionally substituted with alkyl. The —CH$_2$— is optionally substituted with one or more independently selected alkyl. Preferably $X^7$ is selected from the group consisting of a bond or —NH—, optionally substituted with alkyl.

Y is a 5-membered or 6-membered heteroaryl group, such as furanyl, thienyl, oxazolyl, isoxazolyl, thiazolyl, isothiazolyl, thiodiazolyl, oxadiazolyl, pyrrolyl, pyrazolyl, imidazolyl, tetrazolyl, pyridinyl, pyrazinyl, pyrimidinyl, pyridazinyl. The heteroaryl group is optionally substituted with one or more substituents independently selected from the group consisting of halogen, cyano, hydroxy, alkyl, alkoxy, nitro, aminosulfonyl, alkoxycarbonyl, alkylsulfanyl, aryl, aryloxy, arylalkoxy, arylsulfanyl, heteroaryl, heteroaryloxy, and heteroarylsulfanyl. The alkyl, alkoxy, aminosulfonyl, alkoxycarbonyl, alkylsulfanyl, aryl, aryloxy, arylalkoxy, arylsulfanyl, heteroaryl, heteroaryloxy, and heteroarylsulfanyl are optionally substituted with one or more substituents independently selected from the group consisting of halogen, cyano, alkyl, alkoxy, haloalkyl, and haloalkoxy.

$Z^1$ is selected from the group consisting of N and CH, preferably CH. The CH is preferably substituted with a substituent selected from the group consisting of halogen, nitro, cyano, amino sulfonyl, alkyl, alkoxy, alkoxycarbonyl, alkylsulfanyl, alkylsulfinyl, alkylsulfonyl, arylsulfanyl, arylsulfinyl, arylsulfonyl, heteroaryl, heteroarylsulfanyl, heteroarylsulfinyl, and heteroarylsulfonyl. The alkyl, alkoxy, alkoxycarbonyl, alkylsulfanyl, alkylsulfinyl, alkylsulfonyl, alkylsulfanyl, aryl, arylsulfanyl, arylsulfinyl, arylsulfonyl, heteroaryl, heteroarylsulfanyl, heteroarylsulfinyl, and heteroarylsulfonyl are optionally substituted with one or more substituents independently selected from the group consisting of halogen and alkyl, preferably the substituents are fluorine; and the aminosulfonyl is optionally substituted with up to two independently selected alkyl.

$Z^2$ is selected from the group consisting of N and CH, preferably CH. The CH is preferably substituted with a substituent selected from the group consisting of cyano, halogen, nitro, alkyl, alkoxy, haloalkyl, and haloalkylsulfanyl, preferably with a haloalkyl-substituent such as fluoroalkyl, more preferably difluoromethyl and trifluoromethyl.

Each of $Z^3$, $Z^4$, and $Z^5$ is independently selected from the group consisting of N and CH, preferably CH. The CH is optionally substituted with a substituent selected from the group consisting of halogen, cyano, nitro, alkyl, alkoxy, alkylsulfanyl, haloalkyl, haloalkoxy, and haloalkylsulfanyl.

In an even more preferred compound of Formula (I), $X^1$ is selected from the group consisting of —O—, —S—, and —NH—.

$X^2$ is selected from the group consisting of $C_4$-$C_6$-carbocyclyl. The $C_4$-$C_6$-carbocyclyl is optionally substituted with one or more independently selected alkyl.

$X^3$ is selected from the group consisting of —CH$_2$—, and —O—. The —CH$_2$— is optionally substituted with up to two substituents independently selected from the group consisting of alkyl and carbocyclyl. Preferably $X^3$ is —O—.

$X^4$ is selected from the group consisting of —CH$_2$— and —NH—, preferably —CH$_2$—. The —CH$_2$— and —NH— are optionally substituted with up to two methyl-substituents.

$X^5$ is selected from the group consisting of —C(S)—, and —C(O)—.

$X^6$ is a linker selected from the group consisting of

Any such group is optionally substituted with one or more substituents independently selected from the group consisting of halogen, $C_1$-$C_6$-alkyl, hydroxy, $C_1$-$C_6$-alkoxy, oxo, and thiocarbonyl.

$X^7$ is selected from the group consisting of a bond, —O—, —NH—, —S—, —CH$_2$—. The —NH— is optionally substituted with alkyl. The —CH$_2$— is optionally substituted with one or more independently selected alkyl. Preferably $X^7$ is selected from the group consisting of a bond or —NH—, optionally substituted with alkyl.

Y is a nitrogen-containing 5-membered or 6-membered heteroaryl group, preferably containing one, two, three or four nitrogen ring atoms, such as oxazolyl, isoxazolyl, thiazolyl, isothiazolyl, thiodiazolyl, oxadiazolyl, pyrazolyl, imidazolyl, triazolyl, tetrazolyl, pyridinyl, pyrazinyl, pyrimidinyl, and pyridazinyl. The heteroaryl group is optionally substituted with one or more substituents independently selected from the group consisting of halogen, cyano, hydroxy, alkyl, alkoxy, nitro, amino sulfonyl, alkylsulfanyl. The alkyl, alkoxy, amino sulfonyl, alkoxycarbonyl, alkylsulfanyl, are optionally substituted with one or more substituents independently selected from the group consisting of halogen, such as fluorine, bromine or chlorine.

$Z^1$ is CH which is substituted with a substituent selected from the group consisting of halogen, nitro, cyano, amino sulfonyl, alkyl, alkoxy, alkoxycarbonyl, alkylsulfanyl, alkylsulfinyl, alkylsulfonyl, arylsulfanyl, arylsulfinyl, arylsulfonyl, heteroaryl, heteroarylsulfanyl, heteroarylsulfinyl, and heteroarylsulfonyl. The alkyl, alkoxy, alkoxycarbonyl, alkylsulfanyl, alkylsulfinyl, alkylsulfonyl, alkylsulfanyl, aryl, arylsulfanyl, arylsulfinyl, arylsulfonyl, heteroaryl, heteroarylsulfanyl, heteroarylsulfinyl, and heteroarylsulfonyl are optionally substituted with one or more substituents independently selected from the group consisting of halogen and alkyl, preferably the substituents are fluorine; and the aminosulfonyl is optionally substituted with up to two independently selected alkyl.

$Z^2$ is CH which is substituted with a substituent selected from the group consisting of cyano, halogen, nitro, alkyl, alkoxy, haloalkyl, and haloalkylsulfanyl, preferably with a haloalkyl-substituent such as fluoroalkyl, more preferably difluoromethyl and trifluoromethyl.

Each of $Z^3$, $Z^4$, and $Z^5$ is CH. The CH is optionally substituted with a substituent selected from the group consisting of halogen, cyano, nitro, alkyl, alkoxy, alkylsulfanyl, haloalkyl, haloalkoxy, and haloalkylsulfanyl.

Particularly preferred are compounds of the Formula (I), wherein $X^1$ is —O— or —NH—,
$X^2$ is cyclohexyl,
$X^3$ is —O—,
$X^4$ is —CH$_2$—,
$X^5$ is —C(S)— or —C(O)—,
$X^6$ is a linker selected from the group consisting of $X^7$ is a bond or —NH—, Y is thiadiazolyl, pyridinyl (e.g. 2-pyridinyl, 3-pyridinyl or 4-pyridinyl) or, pyrimidinyl (e.g. 2,4-pyrimidinyl, 2,6-pyrimidinyl, 3,5-pyrimidinyl), the thiadiazolyl, pyridinyl and pyrimidinyl are optionally substituted with one or more substituents R independently selected from the group consisting of chloro, cyano, difluoromethyl, trifluoromethyl, methoxy, trifluoromethoxy, and hydroxy, $Z^1$ is C-cyano or C-nitro,
$Z^2$ is C-difluoromethyl or C-trifluoromethyl, preferably C-trifluoromethyl, and
$Z^3$, $Z^4$, and $Z^5$ are CH.

Even more preferred are compounds of the Formula (I), wherein $X^1$ is —O— or —NH—,
$X^2$ is cyclohexyl,
$X^3$ is —O—,
$X^4$ is —CH$_2$—,
$X^5$ is —C(S)— or —C(O)—,
$X^6$ is a linker selected from the group consisting of

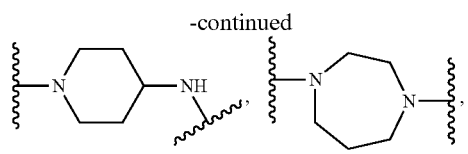

$X^7$ is a bond or —NH—,

Y is thiadiazolyl, or pyridinyl (e.g. 2-pyridinyl, 3-pyridinyl, or 4-pyridinyl), optionally substituted with one or more substituents R, each R is independently selected from the group consisting of chloro, cyano, difluoromethyl, trifluoromethyl, methoxy, and trifluoromethoxy, $Z^1$ is C-cyano or C-nitro, $Z^2$ is C-difluormethyl or C-trifluoromethyl, preferably C-trifluoromethyl, and $Z^3$, $Z^4$, and $Z^5$ are CH.

The compounds of the formula (I) and salts thereof are hereinafter together referred to as "compound(s) of this invention".

This invention also is directed, in part, to methods for making the compounds of this invention, and intermediates thereof. The preferred embodiments specified in this description for the compounds of the formula (I) represent likewise preferred embodiments for the intermediates, such as the intermediates of the formulae (II), (III), (IV) and (V) as defined in the experimental section below.

This invention also is directed, in part, to pharmaceutical compositions. The pharmaceutical compositions comprise a) at least one compound of this invention; and b) at least one excipient, and/or at least one active compound (preferably anthelmintic compound) which differs in structure from the component a).

This invention also is directed, in part, to methods for treating a disease in an animal, particularly a helminth infection. The methods comprise administering at least one compound of this invention to the animal.

This invention also is directed, in part, to a use of at least one compound of this invention as a medicament, e.g. for controlling helminthic infections. This invention also is directed, in part, to a use of at least one compound of this invention to prepare a medicament for treating a disease (e.g., a helminth infection) in an animal.

This invention also is directed, in part, to a kit. The kit comprises at least one compound of this invention. In addition, the kit comprises at least one other component, such as another ingredient (e.g., an excipient or active ingredient), and/or an apparatus for combining the compound of this invention with another ingredient, and/or an apparatus for administering the compound of this invention, and/or a diagnostic tool.

Further benefits of Applicants' invention will be apparent to one skilled in the art from reading this specification.

DETAILED DESCRIPTION OF PREFERRED EMBODIMENTS

This detailed description of preferred embodiments is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating preferred embodiments of this invention, are intended for purposes of illustration only. This invention, therefore, is not limited to the preferred embodiments described in this specification, and may be variously modified.

Compounds of the Invention

The invention relates to compounds of formula (I) and salts and intermediates thereof. The compounds of the formula (I) generally correspond in structure to Formula (I):

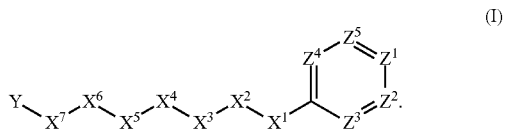

The substituents in Formula (I) and in the intermediates of the Formulae (II), (III), (IV) and (V) (as defined in the experimental section below) are preferably defined as follows:

A. Preferred Embodiments of $X^1$

In some embodiments, $X^1$ is selected from the group consisting of —O—, —C(O)—, —S—, —S(O)—, —S(O)$_2$—, and —NH—. Here, the —NH— is optionally substituted with a substituent selected from the group consisting of $C_1$-$C_6$-alkyl, $C_2$-$C_6$-alkenyl, $C_2$-$C_6$-alkynyl, $C_1$-$C_6$-alkoxy-$C_1$-$C_6$-alkyl, $C_3$-$C_6$-carbocyclyl, and $C_3$-$C_6$-carbocyclyl-$C_1$-$C_6$-alkyl. Any such substituent is optionally substituted with one or more independently selected halogen.

Preferably $X^1$ is selected from the group consisting of —O— and —NH—. The —NH— is optionally substituted with a substituent selected from the group consisting of $C_1$-$C_6$-alkyl.

In some embodiments, $X^1$ is —O—. In such embodiments, the compound of the formula (I) is encompassed by the following formula:

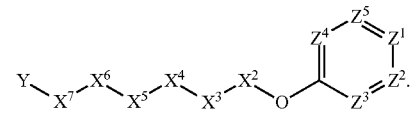

In some embodiments, $X^1$ is —NH— optionally substituted with $C_1$-$C_6$-alkyl. To illustrate, in some such embodiments, $X^1$ is —NH—. In such embodiments, the compound of the formula (I) is encompassed by the following formula:

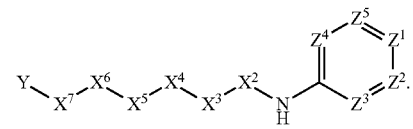

B. Preferred Embodiment $X^2$

In some embodiments, $X^2$ is selected from the group consisting of straight-chain $C_3$-$C_5$-alkyl, straight-chain $C_3$-$C_5$-alkenyl, straight-chain $C_3$-$C_5$-alkynyl, and $C_4$-$C_6$-carbocyclyl are optionally substituted with one or more independently selected $C_1$-$C_6$-alkyl.

In some embodiments, $X^2$ is $C_4$-$C_6$-carbocyclyl such as cyclohexyl. In such embodiments, the compound of the formula (I) is encompassed by the following formula:

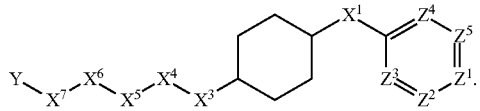

C. Preferred Embodiments of $X^3$

In some embodiments, $X^3$ is —O—. In such embodiments, the compound of the formula (I) is encompassed by the following formula:

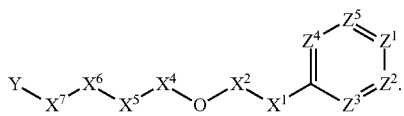

D. Preferred Embodiments of $X^4$

In some embodiments, $X^4$ is —$CH_2$—. The —$CH_2$— is optionally substituted with up to two substituents independently selected from the group consisting of $C_1$-$C_6$-alkyl, $C_1$-$C_6$-haloalkyl, $C_2$-$C_6$-alkenyl. In some embodiments, $X^4$ is —$CH_2$—. In such embodiments, the compound of the formula (I) is encompassed by the following formula:

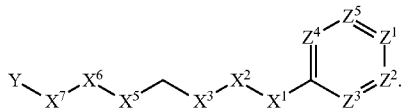

E. Preferred Embodiments of $X^5$

In some embodiments, $X^5$ is selected from the group consisting of —O—, —$CH_2$—, —C(S)—, —C(O)—, —S(O)—, and —$S(O)_2$—. The —$CH_2$— is optionally substituted with up to two substituents independently selected from the group consisting of $C_1$-$C_6$-alkyl and cycloalkyl (e.g., $C_3$-$C_6$-cycloalkyl, such as cyclopropyl).

In some embodiments, $X^5$ is —C(O)—. In those embodiments, the compound of the formula (I) is encompassed by the following formula:

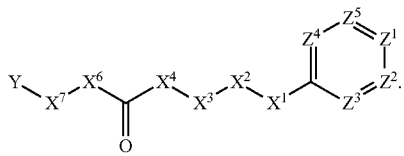

In other embodiments, $X^5$ is —C(S)—. In those embodiments, the compound of the formula (I) is encompassed by the following formula:

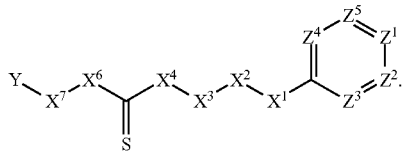

F. Preferred Embodiments of $X^6$ $X^6$ is a linker. The linker is a hydrocarbon group, except: (a) the linker comprises one or more nitrogen atoms, and (b) one or more of the carbons in the hydrocarbon optionally are substituted with one or more substituents independently selected from the group consisting of oxo, halogen, hydroxy, and alkoxy. The linker comprises at least one chain of from 3 to 6 atoms that bridges $X^5$ to $X^7$. From 1 to 2 of the chain atoms are nitrogen. Preferably the linker binds via one of the nitrogen chain atoms to $X^5$. It is also preferred that the linker has no chain of less than 3 atoms that bridges $X^5$ and $X^7$.

In some embodiments, the linker is a hydrocarbon group, except: (a) the linker comprises one or more nitrogen atoms, and (b) one or more of the carbons in the hydrocarbon optionally are substituted with one or more substituents independently selected from the group consisting of oxo, halogen, hydroxy, and $C_1$-$C_6$-alkoxy.

In some embodiments, the linker is a hydrocarbon group, except: (a) the linker comprises one or more nitrogen atoms, and (b) one or more of the carbons in the hydrocarbon optionally are substituted with oxo.

In some embodiments, the linker is a hydrocarbon group, except: (a) the linker comprises one or more nitrogen atoms, and (b) one carbon in the hydrocarbon is substituted with oxo.

In some embodiments, the linker is a hydrocarbon group, except for comprising one or more nitrogen atoms.

In some embodiments, the linker comprises no greater than one nitrogen atom.

In other embodiments, the linker comprises two nitrogen atoms.

In some embodiments, the linker comprises at least one chain of from 3 to 5 atoms that bridges $X^5$ to $X^7$.

In some embodiments, the linker comprises at least one 3-atom chain that bridges $X^5$ to $X^7$.

In some embodiments, the linker comprises at least one 4-atom chain that bridges $X^5$ to $X^7$. In some such embodiments, the linker has no chain of less than 4 atoms that bridges $X^5$ to $X^7$.

In some embodiments, the linker comprises at least one 5-atom chain that bridges $X^5$ to $X^7$. In some such embodiments, the linker has no chain of less than 5 atoms that bridges $X^5$ to $X^7$.

In some embodiments, the linker comprises at least one 6-atom chain that bridges $X^5$ to $X^7$. In some such embodiments, the linker has no chain of less than 6 atoms that bridges $X^5$ to $X^7$.

In some embodiments, $X^6$ is selected from the group of linkers consisting of those shown in Table I, wherein each of said linkers $X^6$ binds via a nitrogen chain atom to $X^5$ (see the right linkage in the structures shown in Table I),

TABLE I

Examples of X⁶ Linkers

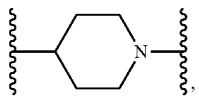

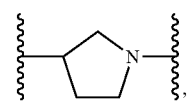 [SMILES: *C1CCN(*)C1]

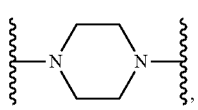

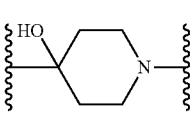

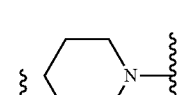

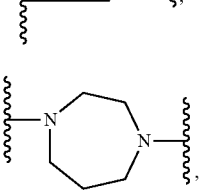

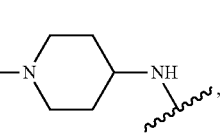

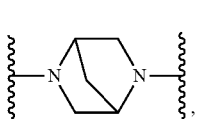

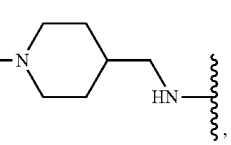

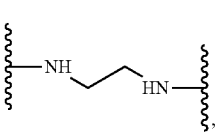

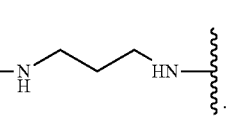

Any such group is optionally substituted with one or more substituents independently selected from the group consisting of halogen, $C_1$-$C_6$-alkyl, hydroxy, $C_1$-$C_6$-alkoxy, oxo, and thiocarbonyl.

In some embodiments, the linker comprises at least one 3-atom chain that bridges $X^5$ to $X^7$. To illustrate, the following are some of the structures from Table I that exemplify such linkers:

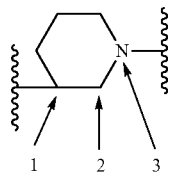 [SMILES: *C1CCCN(*)C1]

In some embodiments, the linker comprises at least one 4-atom chain that bridges $X^5$ to $X^7$. To illustrate, the following are some of the structures from Table I that exemplify such linkers:

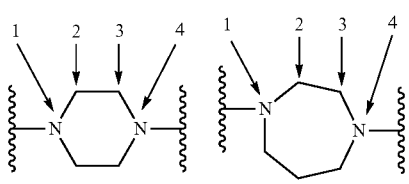

In some embodiments, the linker comprises at least one 5-atom chain that bridges $X^5$ to $X^7$. To illustrate, the following are some of the structures from Table I that exemplify such linkers:

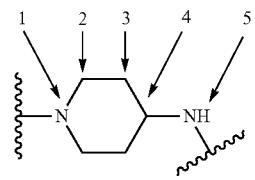 [SMILES: *NC1CCN(*)CC1]

In some embodiments, the linker comprises at least one 6-atom chain that bridges $X^5$ to $X^7$. To illustrate, the following is a structure from Table I that exemplifies such a linker

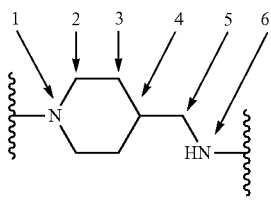

In some embodiments, the structures in Table I are not substituted with any $C_1$-$C_6$-alkyl or oxo.

In some embodiments, $X^6$ does not comprise a ring. In some such embodiments, $X^6$ is a linker selected from the group consisting of:

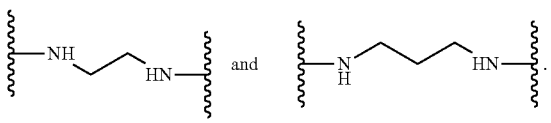 [SMILES: *NCCN* ; *NCCCN*]

Any such group is optionally substituted with one or more substituents independently selected from the group consisting of $C_1$-$C_6$-alkyl and oxo.

In some embodiments, $X^6$ is one of the single- or double-ring structures in Table I. The ring(s) is/are optionally substituted with one or more substituents independently selected from the group consisting of halogen, hydroxy, $C_1$-$C_6$-alkyl, $C_1$-$C_6$-alkoxy, oxo, and thiocarbonyl.

In some embodiments, $X^6$ is one of the 4- to 7-member single ring structures in Table I. The ring is optionally substituted with one or more substituents independently selected from the group consisting of halogen, hydroxy, $C_1$-$C_6$-alkyl, $C_1$-$C_6$-alkoxy, oxo, and thiocarbonyl.

In some embodiments, $X^6$ is one of the 4- to 7-member single ring structures in Table I. The ring is optionally substituted with one or more substituents independently selected from the group consisting of halogen, hydroxy, $C_1$-$C_6$-alkyl, $C_1$-$C_6$-alkoxy, and oxo.

In some embodiments, $X^6$ is one of the 4- to 7-member single ring structures in Table I. The ring is optionally substituted with one or more substituents independently selected from the group consisting of $C_1$-$C_6$-alkyl and oxo.

In some embodiments, $X^6$ is:

In those embodiments, the compound of the formula (I) is encompassed by the following formula:

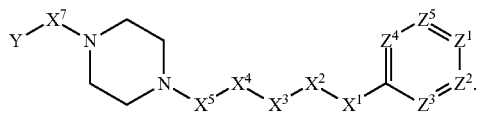

In some embodiments, $X^6$ is:

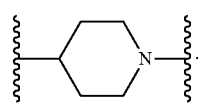

In such embodiments, the compound of the formula (I) is encompassed by the following formula:

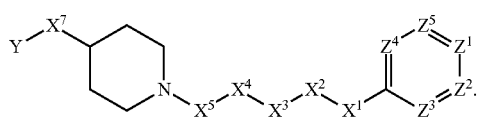

In some embodiments, $X^6$ is:

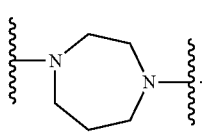

In such embodiments, the compound of the formula (I) is encompassed by the following formula:

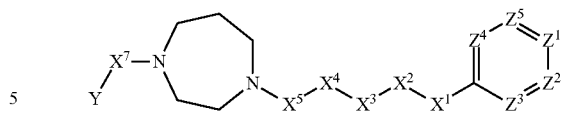

In some embodiments, $X^6$ is:

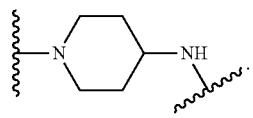

In such embodiments, the compound of the formula (I) is encompassed by the following formula:

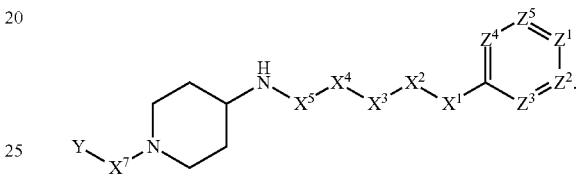

In some embodiments, one or more carbon atoms in the linker are substituted with one or two substituents independently selected from the group consisting of halogen, hydroxy, $C_1$-$C_6$-alkyl, $C_1$-$C_6$-alkoxy, oxo, and thiocarbonyl.

In some embodiments, one or more carbon atoms in the linker are substituted with one or two substituents independently selected from the group consisting of halogen, hydroxy, $C_1$-$C_6$-alkyl, $C_1$-$C_6$-alkoxy, and oxo.

In some embodiments, $X^6$ is one of the single- or double-ring structures in Table I, and one or two of the ring atoms in the ring structure are substituted with a substituent independently selected from the group consisting of methyl, hydroxy and oxo. To illustrate, in some embodiments, the a ring atom is substituted with a hydroxy substituent. The linker in such an instance may be, for example:

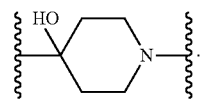

In such embodiments, the compound of the formula (I) is encompassed by the following formula:

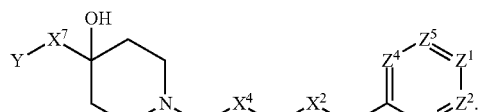

G. Preferred Embodiments of $X^7$

Preferably $X^7$ is selected from the group consisting of a bond or —NH—, optionally substituted with $C_1$-$C_6$-alkyl. In some embodiments, $X^7$ is —NH—. In such embodiments, the compound of the formula (I) is encompassed by the following formula:

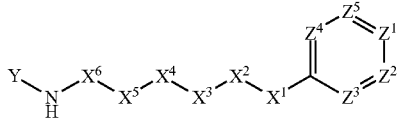

In some embodiments, $X^7$ is a bond. In such embodiments, the compound of the formula (I) is encompassed by the following formula:

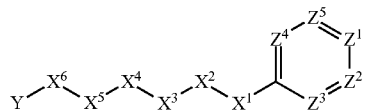

H. Preferred Embodiments of Y

In some embodiments, Y is a 5-membered or 6-membered heteroaryl group, such as such as furanyl, thienyl, oxazolyl, isoxazolyl, thiazolyl, isothiazolyl, thiodiazolyl, oxadiazolyl, pyrrolyl, pyrazolyl, imidazolyl, tetrazolyl, pyridinyl, pyrazinyl, pyrimidinyl, pyridazinyl.

In some embodiments Y is a nitrogen-containing 5-membered or 6-membered heteroaryl group, preferably containing one, two, three or four nitrogen ring atoms. In addition said heteroaryl group may contain further hetero-atoms such as oxygen or sulfur.

In some embodiments Y is a nitrogen-containing 5-membered or 6-membered heteroaryl group, preferably containing one, two or three nitrogen ring atoms, such as oxazolyl, isoxazolyl, thiazolyl, isothiazolyl, thiodiazolyl, oxadiazolyl, pyrazolyl, imidazolyl, triazolyl, tetrazolyl, pyridinyl, pyrazinyl, pyrimidinyl, and pyridazinyl.

In some embodiments Y is thiadiazolyl, pyridinyl (e.g. 2-pyridinyl, 3-pyridinyl or 4-pyridinyl), pyrimidinyl (e.g. 2,4-pyrimidinyl, 2,6-pyrimidinyl, 3,5-pyrimidinyl).

In some embodiments, the heteroaryl group Y carries one or more substituents R, preferably one or two substituents R, more preferably one substituent R. In some embodiments the substituent(s) R is/are selected from the group consisting of chloro, cyano, trifluoromethyl, methoxy, trifluoromethoxy, and oxo.

In some embodiments the substituent R is located in the 2, 3 or 4-position relative to the bond of Y with $X^7$, said substituent R preferably selected from the group consisting of chloro, cyano, trifluoromethyl, methoxy, trifluoromethoxy, and oxo.

I. Preferred Embodiments of $Z^1$, $Z^2$, $Z^3$, $Z^4$, and $Z^5$

In some embodiments, $Z^1$ is selected from the group consisting of N and CH. The CH is preferably substituted with a substituent selected from the group consisting of halogen, nitro, cyano, amino sulfonyl, $C_1$-$C_6$-alkyl, $C_1$-$C_6$-alkoxy, $C_1$-$C_6$-alkoxycarbonyl, $C_1$-$C_6$-alkylsulfanyl, $C_1$-$C_6$-alkylsulfinyl, $C_1$-$C_6$-alkylsulfonyl, aryl, arylsulfanyl, arylsulfinyl, arylsulfonyl, heteroaryl, heteroarylsulfanyl, heteroarylsulfinyl, and heteroarylsulfonyl. The $C_1$-$C_6$-alkyl, $C_1$-$C_6$-alkoxy, $C_1$-$C_6$-alkoxycarbonyl, $C_1$-$C_6$-alkylsulfanyl, $C_1$-$C_6$-alkylsulfinyl, $C_1$-$C_6$-alkylsulfonyl, $C_1$-$C_6$-alkylsulfanyl, aryl, arylsulfanyl, arylsulfinyl, arylsulfonyl, heteroaryl, heteroarylsulfanyl, heteroarylsulfinyl, and heteroarylsulfonyl are optionally substituted with one or more substituents independently selected from the group consisting of halogen and $C_1$-$C_6$-alkyl. The aminosulfonyl is optionally substituted with up to two independently selected $C_1$-$C_6$-alkyl. In some such embodiments, each aryl is phenyl, and each heteroaryl is a 5- to 6-member heteroaryl.

In some embodiments, $Z^1$ is CH. Such embodiments are encompassed by the following structure:

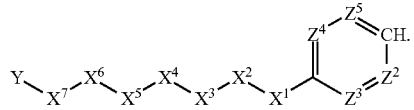

In some embodiments, $Z^1$ is CH substituted with a substituent selected from the group consisting of halogen, nitro, cyano, $C_1$-$C_6$-alkoxy, and $C_1$-$C_6$-alkylsulfanyl. The $C_1$-$C_6$-alkoxy and $C_1$-$C_6$-alkylsulfanyl are optionally substituted with one or more independently selected halogen.

In some embodiments, $Z^1$ is CH substituted with an electron-withdrawing substituent. Such substituents include, for example, halogen, nitro, cyano, halo-$C_1$-$C_6$-alkyl, halo-$C_1$-$C_6$-alkoxy, and halo-$C_1$-$C_6$-alkylsulfanyl.

In some embodiments, $Z^1$ is CH substituted with nitro. Such embodiments are encompassed by the following structure:

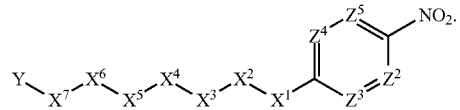

In some embodiments, $Z^1$ is CH substituted with cyano. Such embodiments are encompassed by the following structure:

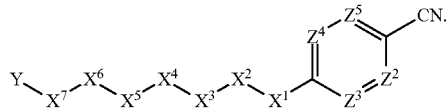

In some embodiments, $Z^2$ is selected from the group consisting of N and CH. The CH is preferably substituted with a substituent selected from the group consisting of cyano, halogen, nitro, $C_1$-$C_6$-alkyl, $C_1$-$C_6$-alkoxy, halo-$C_1$-$C_6$-alkyl, and halo-$C_1$-$C_6$-alkylsulfanyl.

In some embodiments, $Z^2$ is CH substituted with a substituent selected from the group consisting of cyano, halogen, nitro, $C_1$-$C_6$-alkyl, $C_1$-$C_6$-alkoxy, halo-$C_1$-$C_6$-alkyl, and halo-$C_1$-$C_6$-alkylsulfanyl.

In some embodiments, $Z^2$ is CH substituted with halo-$C_1$-$C_6$-alkyl. In some such embodiments, for example, $Z^2$ is CH substituted with fluoro-$C_1$-$C_6$-alkyl, such as difluoromethyl or trifluoromethyl. An example of such embodiments is encompassed by the following structure:

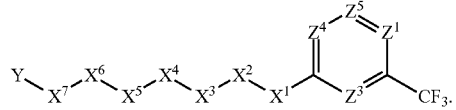

Each of $Z^3$, $Z^4$, and $Z^5$ is independently selected from the group consisting of N and CH. The CH is optionally substituted with a substituent selected from the group consisting of halogen, cyano, nitro, alkyl, alkoxy, alkylsulfanyl, haloalkyl, haloalkoxy, and haloalkylsulfanyl.

Each of $Z^3$, $Z^4$, and $Z^5$ is independently selected from the group consisting of N and CH. The CH is optionally substituted with a substituent selected from the group consisting of halogen, cyano, nitro, $C_1$-$C_6$-alkyl, $C_1$-$C_6$-alkoxy, $C_1$-$C_6$-alkylsulfanyl, halo-$C_1$-$C_6$-alkyl, halo-$C_1$-$C_6$-alkoxy, and halo-$C_1$-$C_6$-alkylsulfanyl.

In some embodiments, one of $Z^3$, $Z^4$, and $Z^5$ is CH.
In some embodiments, two of $Z^3$, $Z^4$, and $Z^5$ are CH.
In some embodiments, all of $Z^3$, $Z^4$, and $Z^5$ are each CH. Such embodiments are encompassed by the following structure:

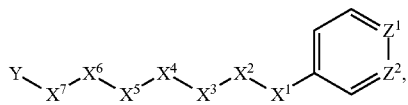

wherein, in a preferred embodiment, $Z^1$ is CH, C-cyano or C-nitro, and $Z^2$ is CH, C-difluoromethyl or C-trifluormethyl, even more preferred $Z^1$ is C-cyano or C-nitro, and $Z^2$ is C-difluoromethyl or C-trifluormethyl.

J. Salts

A salt of the compounds of the formula (I) may be advantageous due to one or more of the salt's physical properties, such as pharmaceutical stability in differing temperatures and humidities; crystalline properties; and/or a desirable solubility in water, oil, or other solvent. In some instances, a salt may be used as an aid in the isolation, purification, and/or resolution of the compound. Acid and base salts can typically be formed by, for example, mixing the compound with an acid or base, respectively, using various known methods in the art. To the extent a salt of the compound is intended to be administered in vivo (i.e., to an animal) for a therapeutic benefit, the salt preferably is pharmaceutically acceptable.

Salts may also be of advantage in the synthesis of the compounds of this invention. For instance intermediates of the compounds of this invention, such as amides of the formula (II), may advantageously be used in form of their salts in the preparation process of the compounds of this invention.

In general, an acid addition salt can be prepared by reacting a free base compound with an approximately stoichiometric amount of an inorganic or organic acid. Examples of often suitable inorganic acids for making (pharmaceutically acceptable) salts include hydrochloric, hydrobromic, hydroiodic, nitric, carbonic, sulfuric, and phosphoric acid. Examples of often suitable organic acids for making (pharmaceutically acceptable) salts generally include, for example, aliphatic, cycloaliphatic, aromatic, araliphatic, heterocyclic, carboxylic, and sulfonic classes of organic acids. Specific examples of often suitable organic acids include cholic, sorbic, lauric, acetic, trifluoroacetic, formic, propionic, succinic, glycolic, gluconic, digluconic, lactic, malic, tartaric acid, citric, ascorbic, glucuronic, maleic, fumaric, pyruvic, aspartic, glutamic, aryl carboxylic acid (e.g., benzoic), anthranilic acid, mesylic, stearic, salicylic, p-hydroxybenzoic, phenylacetic, mandelic, embonic (pamoic), alkylsulfonic (e.g., ethanesulfonic), arylsulfonic (e.g., benzenesulfonic), pantothenic, 2-hydroxyethanesulfonic, sulfanilic, cyclohexylaminosulfonic, β-hydroxybutyric, galactaric, galacturonic, adipic, alginic, butyric, camphoric, camphorsulfonic, cyclopentanepropionic, dodecylsulfic, glycoheptanoic, glycerophosphic, heptanoic, hexanoic, nicotinic, 2-naphthalesulfonic, oxalic, palmoic, pectinic, 3-phenylpropionic, picric, pivalic, thiocyanic, tosylic, and undecanoic acid. In some such embodiments, for example, the salt comprises a trifluoroacetate, mesylate, or tosylate salt. In other embodiments, the salt comprises a hydrochloric acid salt.

In general, a base addition salt can be prepared by reacting a free acid compound with an approximately stoichiometric amount of an inorganic or organic base. Examples of base addition salts may include, for example, metallic salts and organic salts. Metallic salts, for example, include alkali metal (group Ia) salts, alkaline earth metal (group IIa) salts, and other physiologically acceptable metal salts. Such salts may be made from aluminum, calcium, lithium, magnesium, potassium, sodium, and zinc. For example, a free acid compound may be mixed with sodium hydroxide to form such a base addition salt. Organic salts may be made from amines, such as trimethylamine, diethylamine, N,N'-dibenzylethylenediamine, chloroprocaine, ethanolamine, diethanolamine, ethylenediamine, meglumine (N-methylglucamine), and procaine. Basic nitrogen-containing groups may be quaternized with agents such as $C_1$-$C_6$-alkyl halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others.

K. Isomers and Tautomers

The compounds of this invention and their intermediates may exist in various isomeric or tautomeric forms. A reference to a compound of this invention or an intermediate thereof always includes all possible isomeric and tautomeric forms of such compound.

In some embodiments, a compound of this invention may have a hydroxy-substituted aryl or heteroaryl group. A reference to such enol-compound always includes the keto-tautomer as well.

In some embodiments, a compound of this invention may have two or more isomers, such as optical isomers or conformational isomers. For example, the following compound can have a cis or trans configuration:

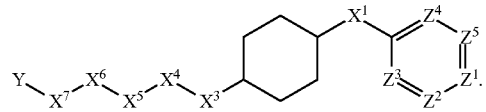

In some preferred embodiments, this compound has the trans configuration such that the compound is encompassed by following formula:

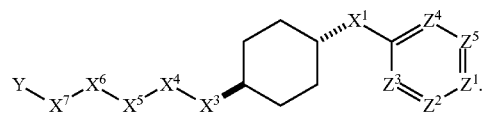

In other embodiments, the compound has the cis configuration such that the compound is encompassed by the following formula:

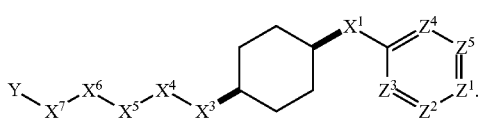

Unless otherwise stated, a compound structure that does not indicate a particular conformation is intended to encompass compositions of all the possible conformational isomers of the compound, as well as compositions comprising fewer than all the possible conformational isomers. In some embodiments, the compound is a chiral compound. In some embodiments, the compound is a non-chiral compound.

Treatment Methods Using Compounds of this Invention

The compounds of this invention may generally be used as a medicament. In accordance with this invention, it has been discovered that the compounds of this invention are particularly useful for treating diseases, such as helminth infections, preferably nematode, cestode or trematode infections, such as nematode infections. In a preferred embodiment the compounds of this invention are used to treat a helminth infection, such as an infection caused by one or more helminths selected from the group consisting of *Anaplocephala* spp.; *Ancylostoma* spp.; *Anecator* spp.; *Ascaridia* spp.; *Ascaris* spp.; *Brugia* spp.; *Bunostomum* spp.; *Capillaria* spp.; *Chabertia* spp.; *Cooperia* spp.; *Cyathostomum* spp.; *Cylicocyclus* spp.; *Cylicodontophorus* spp.; *Cylicostephanus* spp.; *Craterostomum* spp.; *Dicrocoelium* spp.; *Dictyocaulus* spp.; *Dipetalonema* spp.; *Diphyllobothrium* spp.; *Dipylidium* spp.; *Dirofilaria* spp.; *Dracunculus* spp.; *Echinococcus* spp.; *Enterobius* spp.; *Fasciola* spp.; *Filaroides* spp.; *Habronema* spp.; *Haemonchus* spp.; *Heterakis* spp.; *Hyostrongylus* spp.; *Metastrongylus* spp.; *Moniezia* spp.; *Necator* spp.; *Nematodirus* spp.; *Nippostrongylus* spp.; *Oesophagostomum* spp.; *Onchocerca* spp.; *Ostertagia* spp.; *Oxyuris* spp.; *Paramphistomum* spp.; *Parascaris* spp.; *Schistosoma* spp.; *Stephanurus* spp.; *Strongylus* spp.; *Syngamus* spp.; *Taenia* spp.; *Toxocara* spp.; *Strongyloides* spp.; *Teladorsagia* spp.; *Toxascaris* spp.; *Trichinella* spp.; *Trichuris* spp.; *Trichostrongylus* spp.; *Triodontophorous* spp.; *Uncinaria* spp., and/or *Wuchereria* spp.; preferably nematode infections are treated, such as infections by *Trichostrongylus axei*, *Trichostrongylus colubriformis*, *Haemonchus contortus*, *Ascaridia galli*, and/or *Oesophagostomum dentatum*.

It is contemplated that the compounds of this invention may be used to treat a range of animals, especially mammals. Such mammals include, for example, humans. Other mammals include, for example, farm or livestock mammals (e.g., swine, bovines, sheep, goats, etc.), laboratory mammals (e.g., mice, rats, jirds, etc.), companion mammals (e.g., dogs, cats, equines, etc.), and wild and zoo mammals (e.g., buffalo, deer, etc.). It is contemplated that the compounds and salts of this invention also are suitable to treat non-mammals, such as birds (e.g., turkeys, chickens, etc.) and fish (e.g., salmon, trout, koi, etc.).

In some embodiments, one or more compounds of this invention are used to treat an infection by a helminth, such as a nematode, cestode or trematode, preferably a nematode (such as *Haemonchus contortus*), that is resistant to one or more other anthelmintic agents. In some embodiments, the compound of this invention is active against a helminth, such as a nematode, cestode or trematode, preferably a nematode such as *Haemonchus contortus*, that resistant to one or more of the following: an avermectin (e.g., ivermectin, selamectin, doramectin, abamectin, and eprinomectin); a milbemycin (moxidectin and milbemycin oxime); a pro-benzimidazole (e.g., febantel, netobimin, and thiophanate); a benzimidazole derivative, such as a thiazole benzimidazole derivative (e.g., thiabendazole and cambendazole) or a carbamate benzimidazole derivative (e.g., fenbendazole, albendazole (oxide), mebendazole, oxfendazole, parbendazole, oxibendazole, flubendazole, and triclabendazole); an imidazothiazole (e.g., levamisole and tetramisole); a tetrahydropyrimidine (morantel and pyrantel), an organophosphate (e.g., trichlorphon, haloxon, dichlorvos, and naphthalophos); a salicylanilide (e.g., closantel, oxyclozanide, rafoxanide, and niclosamide); a nitrophenolic compound (e.g., nitroxynil and nitroscanate); benzoenedisulphonamide (e.g., clorsulon); a pyrazinaisoquinoline (e.g., praziquantel and epsiprantel); a heterocyclic compound (e.g., piperazine, diethylcarbamazine, dichlorophen, and phenothiazine); an arsenical (e.g., thiacetarsamide, melorsamine, and arsenamide); cyclooctadepsipeptide (e.g., emodepside); and a paraherquamide.

In some such embodiments, for example, the compound of this invention is active against a helminth (for example, *Haemonchus contortus*) resistant to an avermectin, such as ivermectin. In other embodiments, the compound of this invention is alternatively or additionally active against a helminth (for example, *Haemonchus contortus*) resistant to a benzimidazole derivative, such as fenbendazole. In other embodiments, the compound of this invention is alternatively or additionally active against a helminth (for example, *Haemonchus contortus*) resistant to levamisole. And, in other embodiments, the compound of this invention is alternatively or additionally active against a helminth (for example, *Haemonchus contortus*) resistant to pyrantel.

The compounds of this invention may be administered in various dosage forms. The term "dosage form" means that the active ingredient(s) are formulated into a product suitable for administering to the animal via the envisaged dosage route.

One possible dosage form is the oral dosage form, wherein the compound of this invention is administered via the mouth. Oral dosage forms comprise liquids (Drench formulations) (solutions, suspensions and emulsions), semi-solids (pastes), and solids (tablets, capsules, powders, granules, chewable treats, premixes and medicated blocks). Several modified-release delivery systems have been developed, that take advantage of the unique anatomy of the ruminant forestomach. These systems generally comprise intraruminal boluses with a controlled rate of release and are administered using a balling gun. As an alternative the compounds may be administered to a non-human animal with the feedstuff and for this purpose a concentrated feed additive or premix may be prepared for mixing with the normal animal feed or a concentrate (liquid or dry) is mixed with the drinking water for the animal. Other forms of non-direct oral administration include for example the application of the composition onto the coat of the animal and its later ingestion during the self cleaning of the animal.

It is contemplated that the compounds of this invention may alternatively be administered via non-oral routes, such as rectally, via inhalation (e.g., via a mist or aerosol), topically (e.g., via a transdermal patch), or parenterally (e.g., subcutaneous injection, intravenous injection, intramuscular injection, etc.).

For instance the compounds of this invention may be administered topically using a transdermal formulation (i.e. a formulation that passes through the skin). Alternatively the compounds of this invention may be administered topically via the mucosa. Typical formulations for transdermal and mucosal administration include, for example, pour-ons, spot-ons, dips, sprays, mousses, shampoos, powders, gels, hydrogels, lotions, solutions, creams, ointments, dusting powders, dressings, foams, films, skin patches, limb bands, collars, ear tags, wafers, sponges, fibers, bandages, and microemulsions. The pour-on or spot-on methods, for example, comprise applying the composition to a specific location of the skin or coat, such as on the neck or backbone of the animal. This may be achieved by, for example, applying a swab or drop of the pour-on or spot-on formulation to a relatively small area of the recipient animal's skin or coat (i.e., generally no greater than about 10% of the animal recipient's skin or coat). In some embodiments, the compound of this invention is dispersed from the application site to wide areas of the fur due to the spreading nature of the components in the formulation and the animal's movements while, in parallel, being absorbed through the skin and distributed via the animal recipient's fluids and/or tissues.

Parenteral dosage forms and delivery systems for non-oral routes include injectables (solutions, suspensions, emulsions, and dry powders for reconstitution), and implants. A solution for injection is a mixture of two or more components that form a single phase that is homogeneous down to the molecular level. A suspension for injection consists of insoluble solid particles dispersed in a liquid medium, with the solid particles accounting for about 0.5% to about 30% of the suspension. The liquid may be aqueous, oily, or both. An emulsion for injection is a heterogeneous dispersion of one immiscible liquid in another; it relies on an emulsifying agent for stability. A dry powder for parenteral administration is reconstituted as a solution or as a suspension immediately prior to injection. The principal advantage of this dosage form is that it overcomes the problem of instability in solution. The majority of implants used in veterinary medicine are compressed tablets or dispersed matrix systems in which the drug is uniformly dispersed within a nondegradable polymer.

In another aspect the present invention thus provides an anthelmintic dosage form comprising an anthelmitically effective amount of one or more compounds of this invention and one or more excipients.

A dosage form may comprise one or more suitable excipients. Such excipients generally include, for example, sweetening agents, flavoring agents, coloring agents, preservative agents, inert diluents (e.g., calcium carbonate, sodium carbonate, lactose, calcium phosphate, sodium phosphate, or kaolin), granulating and disintegrating agents (e.g., corn starch or alginic acid), binding agents (e.g., gelatin, acacia, or carboxymethyl cellulose), and lubricating agents (e.g., magnesium stearate, stearic acid, or talc). Liquid compositions will generally comprise a solvent, such as, for example, one or more of dimethylformamide, N,N-dimethylacetamide, pyrrolidone, N-methylpyrrolidone, polyethyleneglycol, diethyleneglycolmonoethyl ester, dimethylsulfoxide, andethyl lactate. The solvent preferably has sufficient chemical properties and quantity to keep the compound or salt solubilized under normal storage conditions. In some instances, it may be desirable for the compositions to comprise one or more preservatives. The presence of a preservative may, for example, allow for the compositions to be stored for longer periods. Every excipient in the composition preferably is pharmaceutically acceptable.

The formulation type chosen for a dosage form in any instance will depend upon the particular purpose envisaged and the physical, chemical and biological properties of the compound of this invention.

The dosage forms according to this invention are useful in controlling helminth infections of animals. "Controlling" means to alleviate or reduce parasite numbers in an animal, and/or to inhibit the development of parasite infections in an animal, in whole or in part. Preferably "controlling" means that the parasite count is reduced, after a first administration, by an amount ranging from 5% to about 100%. The effect of the compounds of this invention can be e.g. ovicidal, larvicidal, and/or adulticidal or a combination thereof. The effect can manifest itself directly, i.e. killing the parasites either immediately or after some time has elapsed, for example when molting occurs, or by destroying their eggs, or indirectly, e.g. reducing the number of eggs laid and/or the hatching rate. An "effective amount," is the amount or quantity of a compound that is required to alleviate or reduce parasite numbers in an animal, and/or to inhibit the development of parasite infections in or on an animal, in whole or in part. This amount is readily determined by observation or detection of the parasite numbers both before and after contacting the sample of parasites including their stages with the compound of this invention, directly and/or indirectly, e.g., by contacting articles, surfaces, foliage, or animals with the compound. For an in vivo administration the compound of this invention, is preferably administered in an effective amount which is synonymous with "pharmaceutically effective amount" or "anthelmitically effective amount".

A single administration of a compound of this invention is typically sufficient to treat a helminth infection, such as a nematode, cestode or trematode infection, preferably a nematode infection. Although such a single dose is typically preferred, it is contemplated that multiple doses can be used. When the compound of this invention is orally administered, the total dose to treat a disease such as a helminth infection is generally greater than about 0.01 mg/kg (i.e., milligram of compound of this invention per kilogram body weight). In some such embodiments, the total dose is from about 0.01 to about 100 mg/kg, from about 0.01 to about 50 mg/kg, from about 0.1 to about 25 mg/kg, or from about 1 to about 20. For sheep, for example, the dose is generally from about 1 to about 15 mg/kg, from about 8 to about 12 mg/kg, or about 10 mg/kg. The same dose range may be suitable for other routes of administration. For example, in some embodiments, the same dose range is used for subcutaneous administration. The desired dose, however, may be less in some instances where the compound of this invention is administered parenterally, particularly intravenously. For example, in some such embodiments, the dose is from about 0.01 to about 50 mg/kg, from about 0.01 to about 15 mg/kg, or from about 0.1 to about 10. For sheep, for example, a suitable intravenous dose may be from about 0.01 to about 10 mg/kg, from about 0.1 to about 5 mg/kg, or about 1 mg/kg.

If the compound of this invention is administered parenterally via an injection, the concentration of the compound of this invention in the dosage form preferably is sufficient to provide the desired therapeutically effective amount of the compound of this invention in a volume that is acceptable for parenteral administration.

Factors affecting the preferred dosage may include, for example, the type (e.g., species and breed), age, size, sex, diet, activity, and condition of the intended recipient; the administration route; pharmacological considerations, such as the activity, efficacy, pharmacokinetic, and toxicology profiles of the particular composition administered; and whether the compound of this invention being administered as part of a combination of active ingredients. Thus, the preferred amount of the compound of this invention can vary, and, therefore, can deviate from the typical dosages set forth above. Determining such dosage adjustments is generally within the skill of those in the art.

In a still further aspect the invention provides a method of treating a helminth infection which comprises administering to the animal an anthelmintically effective amount of one or more compounds of this invention. Preferably nematode, cestode or trematode infections are treated, more preferably nematode infections.

This invention is also directed to combinations comprising a) one or more compounds of this invention with b) one or more active compounds which differ in structure from component a). The active compounds b) are preferably anthelmintic compounds, more preferably selected from the group consisting of avermectins (e.g., ivermectin, selamectin, doramectin, abamectin, and eprinomectin); milbemycins (moxidectin and milbemycin oxime); pro-benzimidazoles (e.g., febantel, netobimin, and thiophanate); benzimidazole derivatives, such as a thiazole benzimidazole derivative (e.g., thiabendazole and cambendazole) or a carbamate benzimidazole derivatives (e.g., fenbendazole, albendazole (oxide), mebendazole, oxfendazole, parbendazole, oxibendazole, flubendazole, and triclabendazole); an imidazothiazoles (e.g., levamisole and tetramisole); a tetrahydropyrimidine (morantel and pyrantel), organophosphates (e.g., trichlorphon, haloxon, dichlorvos, and naphthalophos); salicylanilides (e.g., closantel, oxyclozanide, rafoxanide, and niclosamide); nitrophenolic compounds (e.g., nitroxynil and nitroscanate); benzoenedisulphonamides (e.g., clorsulon); pyrazinaisoquinolines (e.g., praziquantel and epsiprantel); heterocyclic compounds (e.g., piperazine, diethylcarbamazine, dichlorophen, and phenothiazine); arsenicals (e.g., thiacetarsamide, melorsamine, and arsenamide); cyclooctadepsipeptides (e.g., emodepside); paraherquamides; and aminoacetonitrile compounds (e.g. monepantel, AAD 1566); (including all pharmaceutically acceptable forms, such as salts).

Preferred combinations are comprising a) one compound selected from the group B1-B7, C1-C14, D1-D8, E1-E11, and F1-F30, (or a salt thereof) and b) one compound selected from the group consisting of avermectins (e.g., ivermectin, selamectin, doramectin, abamectin, and eprinomectin); a milbemycins (moxidectin and milbemycin oxime); pro-benzimidazoles (e.g., febantel, netobimin, and thiophanate); benzimidazole derivatives, such as thiazole benzimidazole derivatives (e.g., thiabendazole and cambendazole), carbamate benzimidazole derivatives (e.g., fenbendazole, albendazole (oxide), mebendazole, oxfendazole, parbendazole, oxibendazole, flubendazole, and triclabendazole); imidazothiazoles (e.g., levamisole and tetramisole); tetrahydropyrimidines (morantel and pyrantel), organophosphates (e.g., trichlorphon, haloxon, dichlorvos, and naphthalophos); salicylanilides (e.g., closantel, oxyclozanide, rafoxanide, and niclosamide); nitrophenolic compounds (e.g., nitroxynil and nitroscanate); benzoenedisulphonamides (e.g., clorsulon); pyrazinaisoquinolines (e.g., praziquantel and epsiprantel); heterocyclic compounds (e.g., piperazine, diethylcarbamazine, dichlorophen, and phenothiazine); arsenicals (e.g., thiacetarsamide, melorsamine, and arsenamide); cyclooctadepsipeptides (e.g., emodepside); paraherquamides; and aminoacetonitrile compounds (e.g. monepantel, AAD 1566); (including all pharmaceutically acceptable forms, such as salts).

This invention also is directed to kits that are, for example, suitable for use in performing the methods of treatment described above. The kit comprises a therapeutically effective amount of one or more compounds of this invention, and an additional component. The additional component(s) may be, for example, one or more of the following: another ingredient (e.g., an excipient or active ingredient), an apparatus for combining the compound of this invention with another ingredient and/or for administering the compound of this invention, or a diagnostic tool.

EXAMPLES

The following examples are merely illustrative, and not limiting to the remainder of the disclosure in any way. The synthesis of the intermediates A1 to A24 described in section A, was started from commercially available compounds, except that in examples A11 to A24 the amine salts prepared in examples A8 to A15 were used. The synthesis of the final products described in sections B, C, D, E and F was started from one or two of the intermediates A1 to A24, to the remainder commercially available compounds were used. All intermediates and final products with $X^2$=cyclohexyl described in this experimental section exhibit a trans configuration at the cylohexyl ring.

The methods described in the examples can be easily adapted by a person skilled in the art to make other compounds of this invention, and intermediates thereof. For instance, a person skilled in the art could replace in the examples of sections B, C, D and E the exemplified starting compounds by other compounds of the formulae (II), (III), (IV) or (V) (e.g. commercially available compounds), perform routine adaptions of the reaction conditions, if any, and use them for the synthesis of further compounds of the formula (I) and salts thereof.

A: Synthesis of Intermediates

The methods described in examples A1 to A24 can routinely be adapted by a person skilled in the art to make other compounds that are useful as intermediates for preparing compounds of the formula (I) and salts thereof.

A1: Preparation of 4-(4-nitro-3-trifluoromethyl-phenoxy)-cyclohexanol

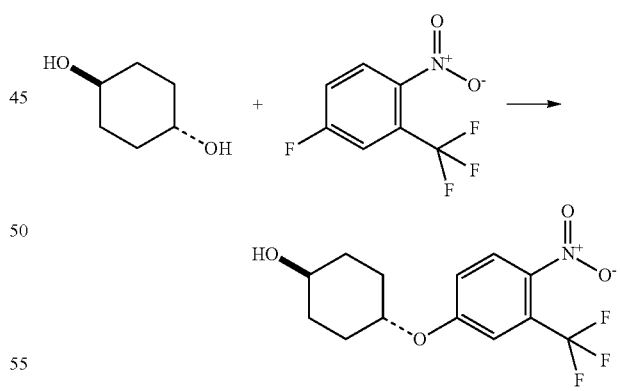

4-Fluoro-1-nitro-2-trifluoromethyl-benzene (11.5 mmol), trans-cyclohexane-1,4-diol (17.2 mmol), and sodium hydride (60% in oil, 11.5 mmol) are suspended in dry dimethylsulfoxide (20 mL) and the resulting mixture is reacted under stirring for 3 hours at 50° C. The reaction is allowed to reach room temperature and is then further reacted at this temperature overnight. The reaction is treated with water (20 mL), the precipitate formed is removed by filtration and the filtrate is extracted with dichloromethane (50 mL). The organic phase is washed with aqueous saturated ammonium chloride (10 mL), dried over magnesium sulfate, filtered and the filtrate is concentrated under reduced pressure. The precipitate is triturated with diethylether (20 mL), filtered and the filtrate concentrated under reduced pressure. Both fractions of crude product are combined, dissolved in dichloromethane and filtered trough a short pad of silica gel to afford the desired product (36% yield).

A2: Preparation of 4-(4-hydroxy-cyclohexyloxy)-2-trifluoromethyl-benzonitrile

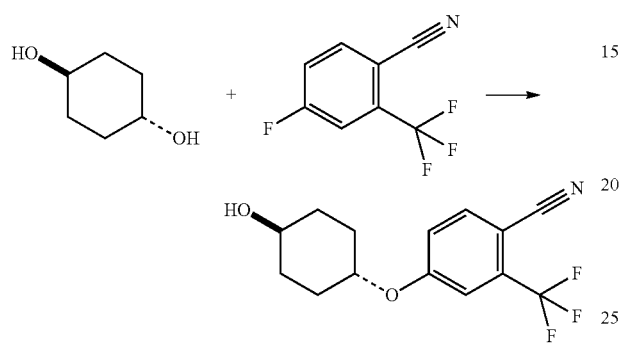

Trans-cyclohexane-1,4-diol (4.30 mmol) and sodium hydride (60% suspension in oil, 2.15 mmol) are suspended in dry dimethylsulfoxide (4 mL) and a solution of 4-fluoro-2-trifluoromethyl-benzonitrile (2.15 mmol) in dry dimethylsulfoxide (4 mL) is added dropwise. The resulting mixture is stirred at room temperature. After 1 hour reaction time, the reaction is treated with water (10 mL), the precipitate formed is separated by filtration and the filtrate is extracted with dichloromethane (25 mL). The organic phase is washed with aqueous saturated ammonium chloride (5 mL), dried over magnesium sulfate, filtered and the filtrate is concentrated under reduced pressure. The precipitate is triturated with diethylether (15 mL), filtered and the filtrate concentrated under reduced pressure. Both fractions of crude product are combined, dissolved in dichloromethane and purified by chromatography through a short pad of silica gel (dichloromethane and then diethylether as eluents) to afford the desired product (60% yield).

A3: Preparation of 4-(4-nitro-3-trifluoromethyl-phenylamino)-cyclohexanol

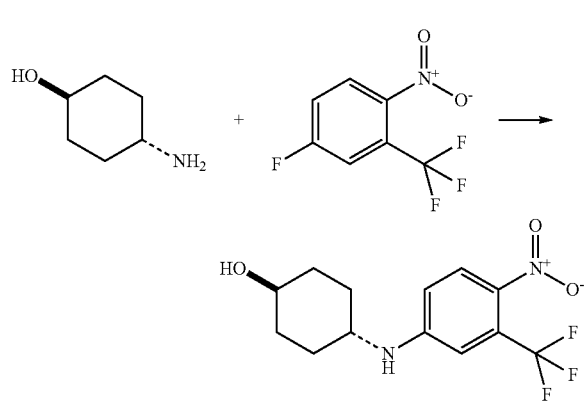

5-Fluoro-2-nitrobenzotrifluoride (400 mg, 1.91 mmol) and trans-4-aminocyclohexanol (220 mg, 1.91 mmol) are dissolved in dimethylsulfoxide (10 mL) and the reaction is then heated at 95° C. for 3.5 hours. After cooling to room temperature, the mixture is diluted with dichloromethane (15 mL) and washed with water (3×10 mL). The organic phase is collected and dried over sodium sulphate, filtered and concentrated under reduced pressure. The crude product is recrystallised from petrol ether. The desired product is finally isolated as a yellow solid (84% yield).

A4: Preparation of 4-(4-hydroxy-cyclohexylamino)-2-trifluoromethyl-benzonitrile

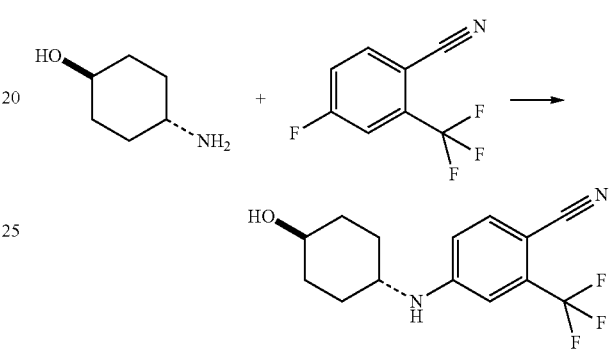

Potassium carbonate (304 mg, 2.2 mmol) is dissolved in a minimum amount of water and 4-fluoro-2-trifluoromethyl-benzonitrile (378 mg, 2.0 mmol) and trans-4-aminocyclohexanol (460 mg, 4.0 mmol) dissolved in acetonitrile (10 mL) are added. The reaction is then heated at 80° C. for 3 days. After cooling to room temperature, the mixture is concentrated under reduced pressure, is taken up in ethyl acetate (15 mL) and washed with saturated aqueous ammonium chloride (2×10 mL) followed by water (10 mL). The organic phase is collected and dried over sodium sulphate, filtered and concentrated under reduced pressure. The desired product is isolated as a colourless solid (80% yield).

A5: Preparation of [4-(3-difluoromethyl-4-nitro-phenylamino)-cyclohexyloxy]-acetic acid Step 1

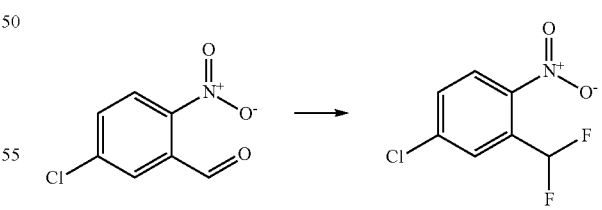

A solution of 5-chloro-2-nitro-benzaldehyde (2.0 mmol) in dry chloroform (4 mL) is cooled to 0° C. and N,N-diethylaminosulfur trifluoride (4.0 mmol) is slowly added under vigorous stirring. The reaction mixture is allowed to reach room temperature and is reacted 2 hours at this temperature. The reaction is diluted by the addition of chloroform (12 mL), an aqueous saturated sodium carbonate solution (10 mL) is added dropwise and the resulting mixture is stirred for 10 minutes. The organic phase is collected and washed with water (10 mL), brine (10 mL), is dried over magnesium sulphate, filtered and concentrated under reduced pressure to afford the desired product (78% yield).

Step 2

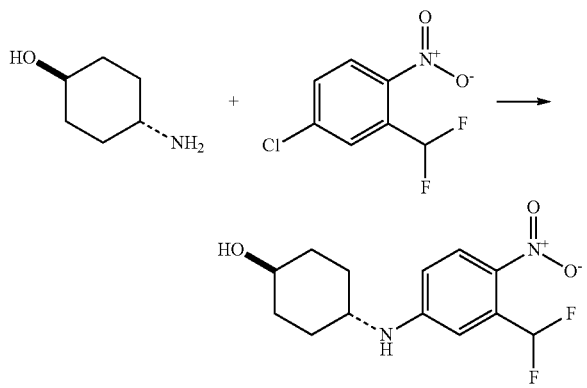

4-Chloro-2-difluoromethyl-1-nitro-benzene (1.55 mmol), trans-4-aminocyclohexanol (2.0 mmol) and triethylamine (2.0 mmol) are dissolved in N-methylpyrrolidone (6 mL) and the resulting mixture is irradiated in a monomode microwave oven for 11 hours at 130° C. After cooling down to room temperature, the reaction is diluted by the addition of ethyl acetate (15 mL) and the organic phase is washed with water (10 mL), an aqueous saturated solution of sodium hydrogencarbonate (10 mL), and brine (10 mL). The organic layer is then dried over magnesium sulphate, filtered and concentrated under reduced pressure. The residue obtained is taken up in a minimum volume of dichloromethane and is purified by chromatography over a short silica gel pad (dichloromethane and then diethylether as eluents) to afford the desired product in the presence of some impurities.

Step 3

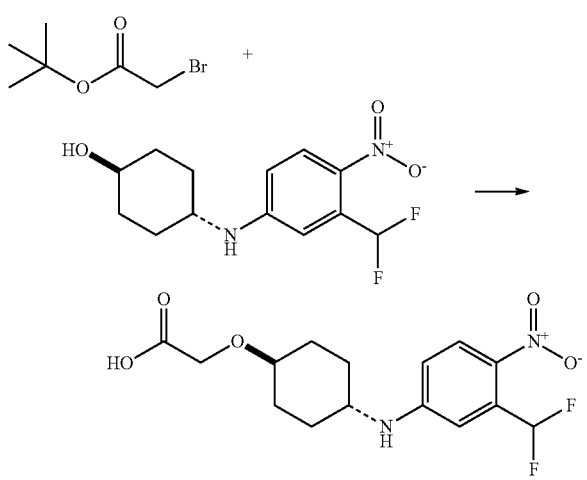

4-(3-Difluoromethyl-4-nitro-phenylamino)-cyclohexanol (0.57 mmol) is dissolved in dry tetrahydrofuran (6 mL) and sodium hydride (60% suspension in oil, 1.0 mmol) is added. The resulting mixture is stirred for 15 min and is cooled down to 5° C. prior to the addition of acetic acid tert-butyl ester (0.70 mmol). After 1.5 hours reaction time, an aqueous solution of hydrochloric acid is slowly added until pH 5 is reached and the mixture is then diluted with ethyl acetate (20 mL). The organic phase is collected and is concentrated under reduced pressure. The residue obtained is then treated with a 1 to 1 mixture of dichloromethane and trifluoroacetic acid (7 mL). After complete conversion of the intermediate ester into the desired acid, the reaction mixture is again concentrated under reduced pressure. The residue obtained is taken up in dichloromethane (20 mL) and the organic phase is extracted with aqueous 3N sodium hydroxide solution (10 mL). The organic phase is then washed with water (2×5 mL), and these aqueous phases are in turn extracted with dichloromethane (2×5 mL). The pH of all combined aqueous phases is then brought to 5 by the addition of aqueous hydrochloric acid. The acidic aqueous phase is extracted with dichloromethane (2×15 mL) and the combined organic layers are dried over magnesium sulphate, filtered and concentrated under reduced pressure to afford the desired acid in the presence of side products (21% overall yield).

A6: Preparation of [4-(4-nitro-3-trifluoromethyl-phenylamino)-cyclohexyloxy]-acetic acid

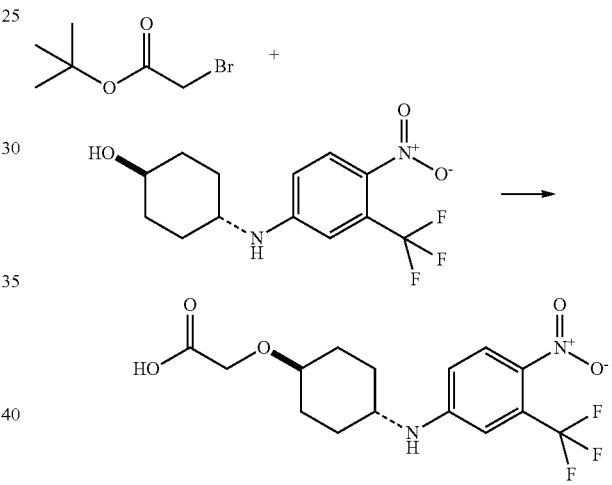

4-(4-Nitro-3-trifluoromethyl-phenylamino)-cyclohexanol (2.79 mmol) is dissolved in dry tetrahydrofuran (7 mL) and sodium hydride (60% suspension in oil, 7.0 mmol) is added. The resulting mixture is stirred for 15 min and is cooled down to 5° C. prior to the addition of acetic acid tert-butyl ester (2.79 mmol). After 1.5 hours reaction time, water (5 mL) is slowly added under vigorous stirring and the mixture is then diluted with ethyl acetate (20 mL). The organic phase is collected and is concentrated under reduced pressure. The residue obtained is then treated with a 1 to 1 mixture of dichloromethane and trifluoroacetic acid (7 mL). After complete conversion of the intermediate ester into the desired acid, the reaction mixture is again concentrated under reduced pressure. The residue obtained is taken up in dichloromethane (20 mL) and the organic phase is extracted with aqueous 3N sodium hydroxide solution (10 mL). The organic phase is then washed with water (2×7 mL), and these aqueous phases are in turn extracted with dichloromethane (2×7 mL). The pH of all combined aqueous phases is then brought to 5-6 by the addition of aqueous 5N hydrochloric acid. The acidic aqueous phase is extracted with dichloromethane (2×15 mL) and the combined organic layers are dried over magnesium sulphate, filtered and concentrated under reduced pressure to afford the desired acid (59% yield).

A7: Preparation of [4-(4-cyano-3-trifluoromethyl-phenylamino)-cyclohexyloxy]-acetic acid

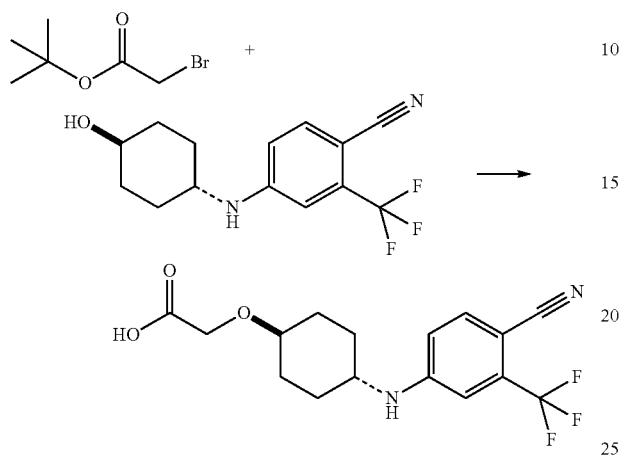

4-(4-Hydroxy-cyclohexylamino)-2-trifluoromethyl-benzonitrile (4.30 mmol) is dissolved in dry tetrahydrofuran (10 mL) and sodium hydride (60% suspension in oil, 13.0 mmol) is added. The resulting mixture is stirred for 15 minutes and is cooled down to 5° C. prior to the addition of acetic acid tert-butyl ester (4.30 mmol). After 1.5 hours reaction time, water (7 mL) is slowly added under vigorous stirring and the mixture is then diluted with ethyl acetate (25 mL). The organic phase is collected and is concentrated under reduced pressure. The residue obtained is then treated with a 1 to 1 mixture of dichloromethane and trifluoroacetic acid (10 mL). After 2 hours, the reaction mixture is concentrated under reduced pressure. The residue obtained is taken up in dichloromethane (20 mL) and the organic phase is extracted with aqueous 3N sodium hydroxide solution (3×7 mL) and washed with water (2×5 mL). The pH of all combined aqueous phases is then brought to 5-6 by the addition of aqueous 5N hydrochloric acid. The acidic aqueous phase is extracted with dichloromethane (4×15 mL) and the combined organic layers are dried over magnesium sulphate, filtered and concentrated under reduced pressure to afford the desired acid (39% yield).

A8: Preparation of 4-(6-difluoromethyl-pyridin-3-yl)-piperazin-1-ium chloride Step 1

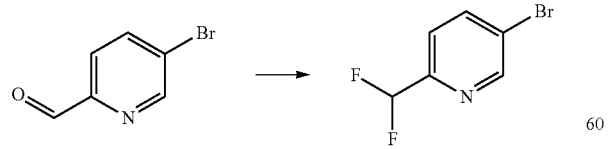

A solution of 5-bromo-pyridine-2-carbaldehyde (1.0 mmol) in dry chloroform (5 mL) is cooled to 0° C. and N,N-diethylaminosulfur trifluoride (2.0 mmol) is slowly added under vigorous stirring. The reaction mixture is reacted 5 minutes at 0° C. and is then allowed to reach room temperature and is further stirred at this temperature overnight. The reaction is diluted by the addition of chloroform (15 mL), an aqueous saturated sodium carbonate solution (10 mL) is added dropwise and the resulting mixture is stirred for 10 minutes. The organic phase is collected and washed with water (10 mL), brine (10 mL), is dried over magnesium sulphate, filtered and concentrated under reduced pressure to afford the desired product which is used in the next step without further purification.

Step 2

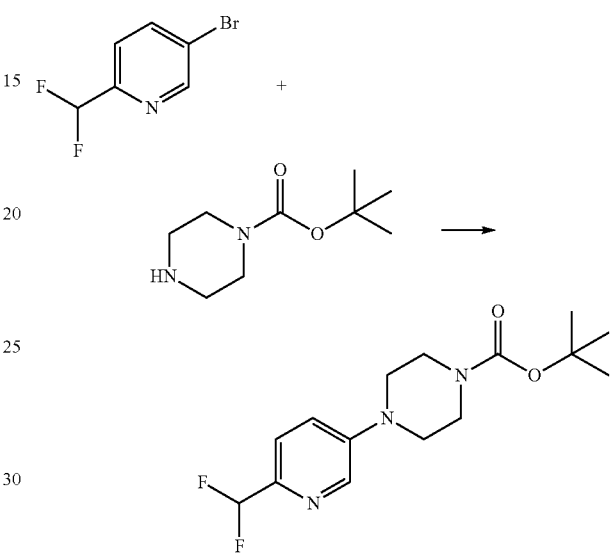

5-Bromo-2-difluoromethyl-pyridine (0.67 mmol), piperazine-1-carboxylic acid tert-butyl ester (0.61 mmol), sodium tert-butoxide (0.93 mmol), tris-(dibenzylideneacetone)-dipalladium (0.013 mmol) and 2-(dicyclohexylphosphino)-biphenyl (0.036 mmol) are dissolved in dry toluene (5 mL) and the resulting mixture is irradiated in a monomode microwave oven for 30 minutes at 100° C. The reaction is then cooled down to room temperature and diethyl ether is added (15 mL). The precipitate formed is filtered and the filtrate is concentrated under reduced pressure to afford the desired product which is used in the next step without further purification.

Step 3

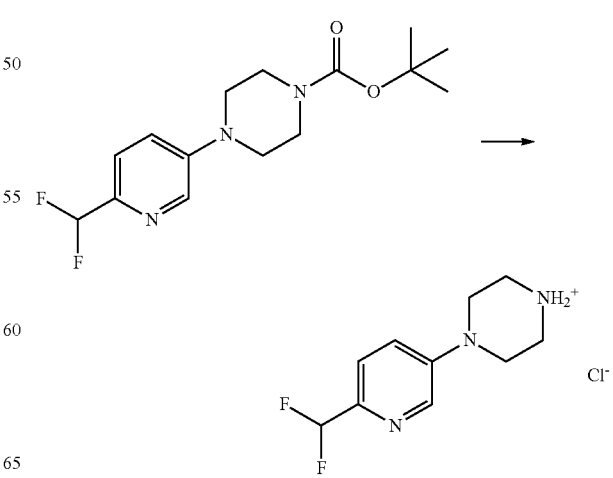

4-(6-Difluoromethyl-pyridin-3-yl)-piperazine-1-carboxylic acid tert-butyl ester (0.67 mmol) is dissolved in a 1 to 4 mixture of trifluoroacetic acid and dichloromethane (5 mL) and the resulting solution is stirred for 1 hour at room temperature. The reaction mixture is concentrated under reduced pressure, taken up in diethyl ether (5 mL) and a 4N hydrochloric acid solution in dioxane (3 mL) is added. After the formation of a precipitate is observed, the mixture is concentrated under reduced pressure to afford the desired product (67% overall yield).

A9: Preparation of 4-(5-difluoromethyl-pyridin-2-yl)-piperazin-1-ium chloride

Step 1

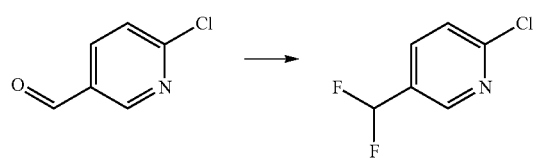 [SMILES: O=Cc1ccc(Cl)nc1 ; FC(F)c1ccc(Cl)nc1]

A solution of 6-chloro-pyridine-3-carbaldehyde (3.2 mmol) in dry chloroform (6 mL) is cooled to 0° C. and N,N-diethylaminosulfur trifluoride (6.4 mmol) is slowly added under vigorous stirring. The reaction mixture is reacted 2 hours at 0° C. and is then allowed to reach room temperature and is further stirred at this temperature overnight. The reaction is diluted by the addition of chloroform (18 mL), an aqueous saturated sodium carbonate solution (15 mL) is added dropwise and the resulting mixture is stirred for 10 minutes. The organic phase is collected and washed with water (10 mL), brine (10 mL), is dried over magnesium sulphate, filtered and concentrated under reduced pressure to afford the desired product which is used in the next step without further purification Step 2

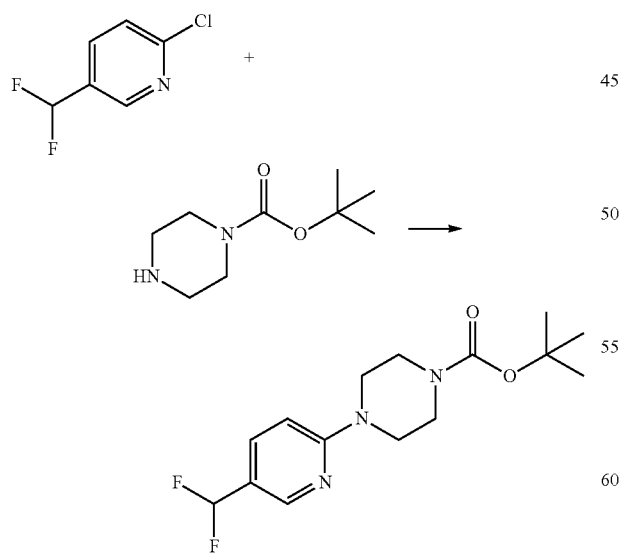

2-Chloro-5-difluoromethyl-pyridine (3.6 mmol), piperazine-1-carboxylic acid tert-butyl ester (3.6 mmol), and triethylamine (4.3 mmol) are dissolved in N,N-dimethylformamide (6 mL) and the resulting mixture is irradiated in a monomode microwave oven for 90 minutes at 130° C. After cooling down to room temperature, the reaction is diluted by the addition of ethyl acetate (15 mL) and the organic phase is washed with an aqueous saturated solution of sodium hydrogencarbonate (10 mL), water (10 mL) and brine (10 mL). The organic layer is then dried over magnesium sulphate, filtered and concentrated under reduced pressure to afford the desired product which is engaged in the next step without further purification.

Step 3

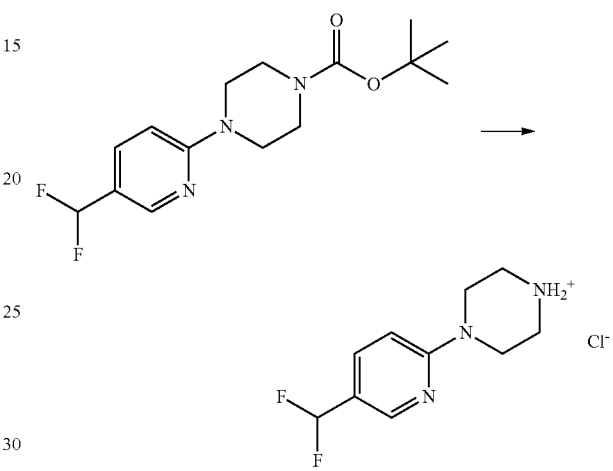

4-(5-Difluoromethyl-pyridin-2-yl)-piperazine-1-carboxylic acid tert-butyl ester (1.0 mmol) is dissolved in a 1 to 3 mixture of trifluoroacetic acid and dichloromethane (8 mL) and the resulting solution is stirred for 1 hour at room temperature. The reaction mixture is concentrated under reduced pressure, taken up in diethyl ether (5 mL) and a 4N hydrochloric acid solution in dioxane (3 mL) is added. The precipitate formed is filtered and dried under high vacuum to afford the desired product (83% overall yield).

A10: Preparation of 4-(2-trifluoromethyl-pyridin-4-ylamino)-piperidin-1-ium chloride Step 1

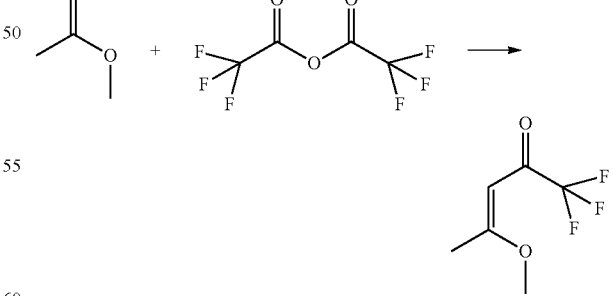

To an ice-cooled solution of 2-methoxy-propene (30 mmol) in dichloromethane (20 mL) and pyridine (0.8 mL) is added trifluoroacetic acid anhydride (43 mmol). The resulting mixture is allowed to attain room temperature and stirred overnight. The pH of the reaction mixture is then adjusted to 7 with 1 N sodium hydroxide solution upon ice-cooling and the layers formed are then separated. The aqueous layer is extracted with dichloromethane (2×10 mL) and the combined organic layers are dried over magnesium sulfate and concentrated under reduced pressure to afford the desired product which is used in the next step without further purification.

Step 2:

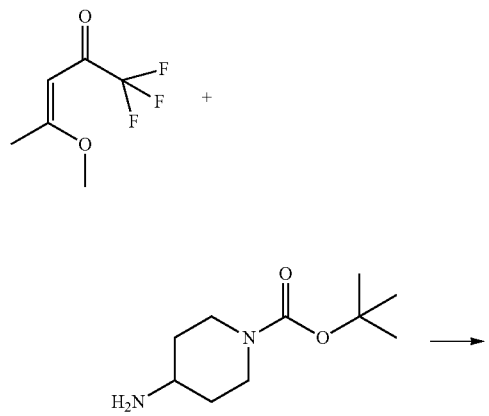

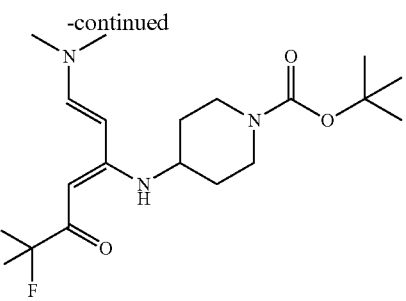

To a solution of 4-((Z)-4,4,4-trifluoro-1-methyl-3-oxo-but-1-enylamino)-piperidine-1-carboxylic acid tert-butyl ester (17.8 mmol) in toluene (20 mL) is added dimethoxymethyl-dimethyl-amine (53.4 mmol) and the reaction mixture is heated under reflux for 3 hours. After cooling to room temperature, all volatiles are removed under reduced pressure to afford the desired product which is used in the next step without further purification.

Step 4:

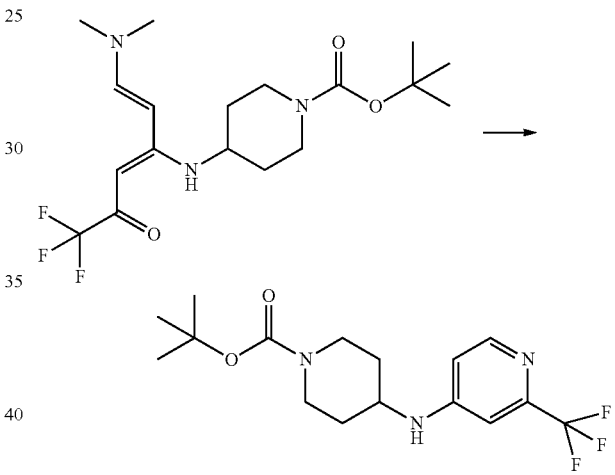

A mixture of (Z)-1,1,1-trifluoro-4-methoxy-pent-3-en-2-one (17.9 mmol) and 4-amino-piperidine-1-carboxylic acid tert-butyl ester (17.8 mmol) in acetonitrile (10 mL) is stirred under reflux for 3 hours. After cooling to room temperature, all volatiles are removed under reduced pressure to afford the desired product which is used in the next step without further purification.

Step 3:

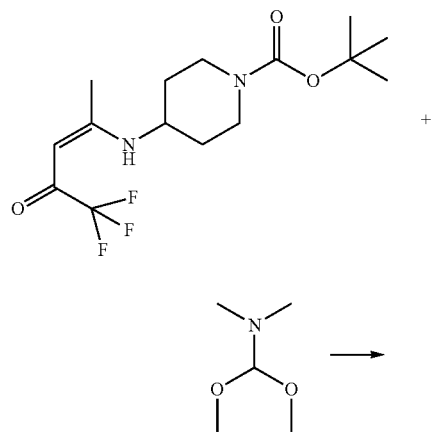

To product from step 3, 4-[(Z)-1-((E)-2-dimethylamino-vinyl)-4,4,4-trifluoro-3-oxo-but-1-enylamino]-piperidine-1-carboxylic acid tert-butyl ester, is added ammonium acetate (65.8 mmol) and dimethylformamide (30 mL) and the resulting mixture is heated under reflux for 2 hours. The reaction mixture is then allowed to attain room temperature, diluted with ethyl acetate and washed with sodium bicarbonate solution (5% in water). The organic layer is separated, dried over magnesium sulfate and concentrated under reduced pressure. Purification of the crude material by flash column chromatography on silica gel (dichloromethane/methanol 100 to 9:1 v/v) yields the desired product.

Step 5:

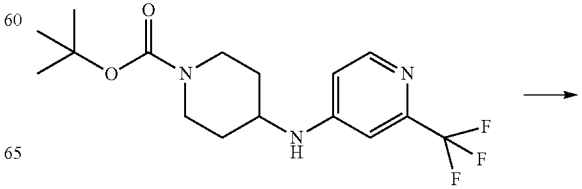

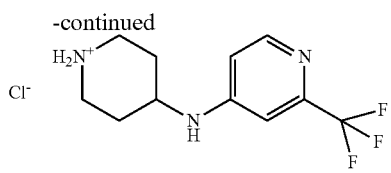

To a solution of 4-(2-trifluoromethyl-pyridin-4-ylamino)-piperidine-1-carboxylic acid tert-butyl ester (4.09 g (11.8 mmol) in dichloromethane (20 mL) is added trifluoroacetic acid (10 mL) and the reaction mixture is stirred at room temperature for one hour. More trifluoroacetic acid (2 mL) is added and stirring is continued for 30 minutes. All volatiles are then removed under high vacuum and to the residue is then added a 4 N solution of HCl in dioxane. All volatiles are then removed again and the residue triturated with diethyl ether. The solid is sucked to dryness and taken up with methanol. After evaporation of all volatiles, the residue is again triturated with diethyl ether and after drying under high vacuum, the desired compound is obtained (26% overall yield).

A11: Preparation of 1-(5-trifluoromethyl-pyridin-2-yl)-[1,4]diazepam-1-ium hydrochloride

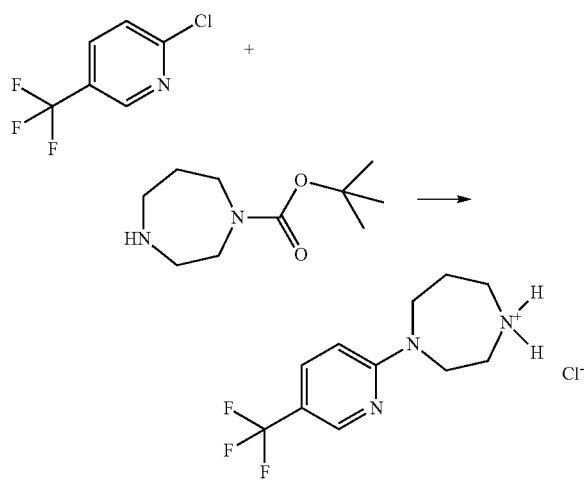

[1,4]-Diazepane-1-carboxylic acid tert-butyl ester (3.0 mmol), 2-chloro-5-trifluoromethyl-pyridine (3.0 mmol) and potassium carbonate (8.0 mmol) are dissolved in dimethylsulfoxide (10 mL), and the resulting mixture is stirred at 100° C. for 5 hours. After cooling to room temperature, the mixture is diluted with ethyl acetate (30 mL), the precipitate removed by filtration and the filtrate is washed with aqueous saturated sodium hydrogencarbonate solution (2×10 mL). The organic phase is dried over magnesium sulphate, filtered and concentrated under reduced pressure. The residue obtained is purified by column chromatography on silica gel (dichloromethane/methanol:9/1 as eluent). The pure intermediate is then dissolved in a 2 to 1 mixture of dichloromethane and trifluoroacetic acid (8 mL) and the reaction mixture is stirred for 1 hour at room temperature. The reaction is then concentrated under reduced pressure, the residue obtained is triturated with a 4N solution of hydrogen hydrochloride in dioxane (5 mL) and the precipitate formed is filtered and dried reduced pressure to afford the desired product (42% yield).

A12: Preparation of 1-(6-methoxy-pyridin-3-yl)-piperazin-1-ium trifluoroacetate Step 1

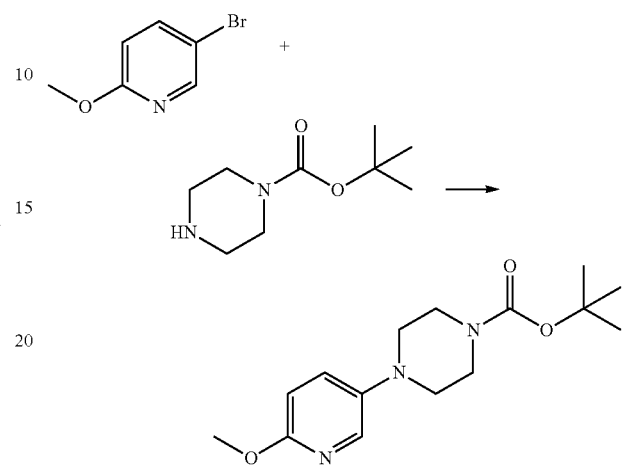

5-Bromo-2-methoxy-pyridine (1.0 mmol), piperazine-1-carboxylic acid tert-butyl ester (1.2 mmol), sodium tert-butoxide (1.65 mmol), tris-(dibenzylideneacetone)-dipalladium (0.022 mmol) and 2-(dicyclohexylphosphino)-biphenyl (0.064 mmol) are dissolved in dry toluene (5 mL) and the resulting mixture is irradiated in a monomode microwave oven for 30 minutes at 100° C. The reaction is then cooled down to room temperature and ethyl acetate is added (15 mL). The precipitate formed is filtered and the filtrate is concentrated under reduced pressure. The crude product thus obtained is taken up in a minimum volume of dichloromethane (2 mL) and is purified by chromatography over a short silica gel pad (diethyl ether as eluent) to afford the desired product.

Step 2

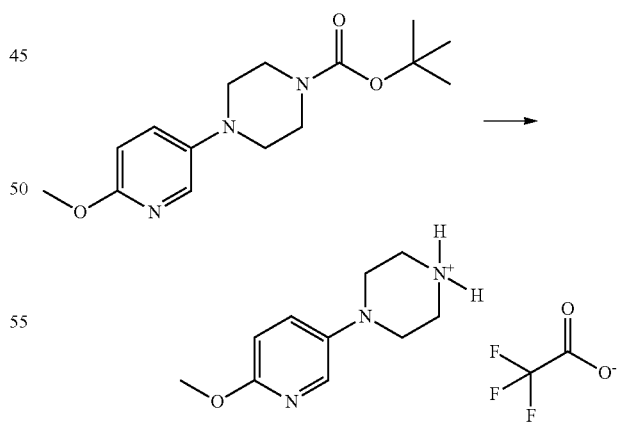

Product from step 1,4-(6-methoxy-pyridin-3-yl)-piperazine-1-carboxylic acid tert-butyl ester (0.44 mmol), is dissolved in a mixture of trifluoroacetic acid (1.2 mL) and dichloromethane (3 mL). The mixture is stirred for 2 hours at room temperature and is then concentrated under reduced pressure to afford the desired product as the trifluoroacetate salt (71% overall yield).

A13: Preparation of 1-(6-trifluoromethyl-pyridin-3-yl)-piperazin-1-ium trifluoroacetate Step 1

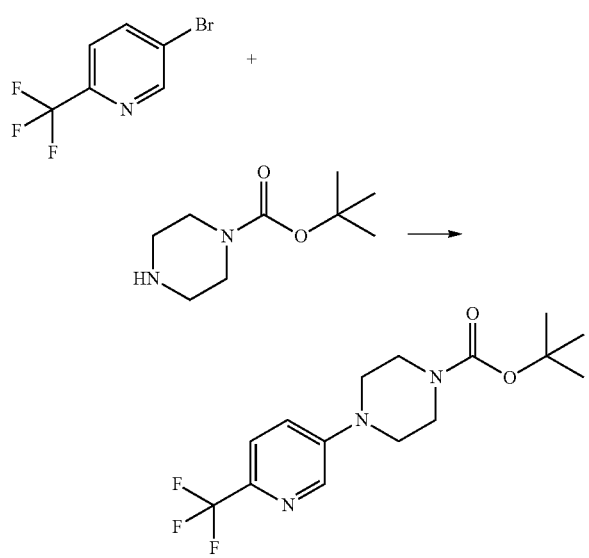

5-Bromo-2-trifluoromethyl-pyridine (1.0 mmol), piperazine-1-carboxylic acid tert-butyl ester (1.2 mmol), sodium tert-butoxide (1.65 mmol), tris-(dibenzylideneacetone)-dipalladium (0.022 mmol) and 2-(dicyclohexylphosphino)-biphenyl (0.064 mmol) are dissolved in dry toluene (5 mL) and the resulting mixture is irradiated in a monomode microwave oven for 30 minutes at 100° C. The reaction is then cooled down to room temperature and ethyl acetate is added (15 mL). The precipitate formed is filtered and the filtrate is concentrated under reduced pressure. The crude product thus obtained is taken up in a minimum volume of dichloromethane (2 mL) and is purified by chromatography over a short silica gel pad (diethyl ether as eluent) to afford the desired product.

Step 2

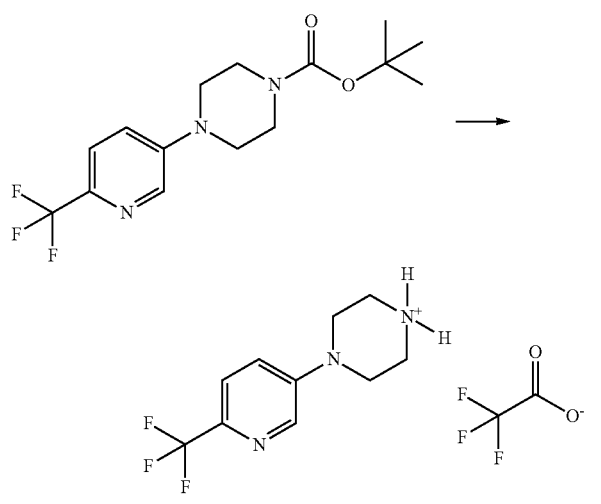

Product from step 1,4-(6-trifluoromethyl-pyridin-3-yl)-piperazine-1-carboxylic acid tert-butyl ester (0.77 mmol), is dissolved in a mixture of trifluoroacetic acid (1.2 mL) and dichloromethane (3 mL). The mixture is stirred for 2 hours at room temperature and is then concentrated under reduced pressure to afford the desired product as the trifluoroacetate salt (82% overall yield).

A14: Preparation of 4-(6-cyano-pyridin-3-yl)-piperazin-1-ium trifluoroacetate Step 1

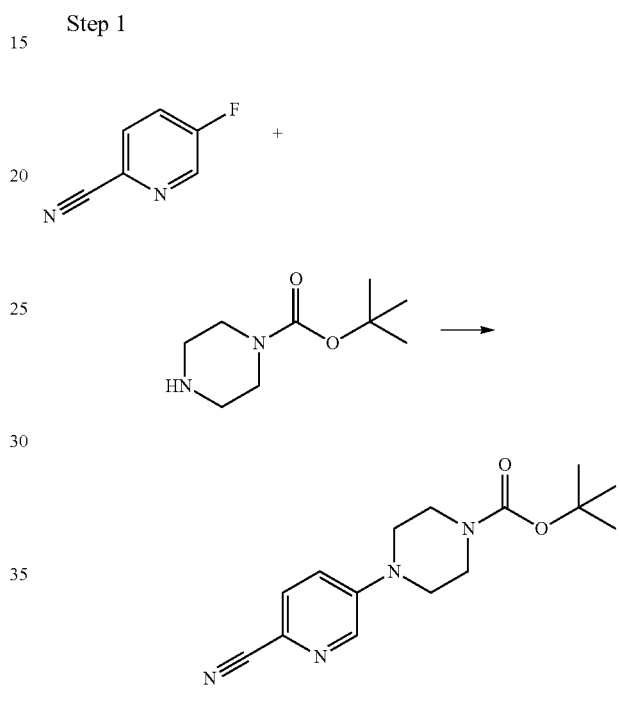

5-Fluoro-pyridine-2-carbonitrile (1.5 mmol), piperazine-1-carboxylic acid tert-butyl ester (1.5 mmol) and potassium carbonate are dissolved in dry dimethylsulfoxide (7 mL) and the resulting mixture is reacted for 5 hours at 100° C. under stirring. The reaction is then cooled down to room temperature and is diluted with ethyl acetate (15 mL). The organic layer is then washed with aqueous saturated ammonium chloride solution (2×10 mL) and with aqueous saturated sodium chloride solution (10 mL). The organic layer is then dried over magnesium sulphate, filtered and concentrated under reduced pressure to afford the desired product.

Step 2

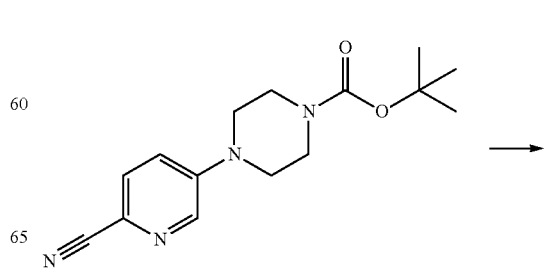

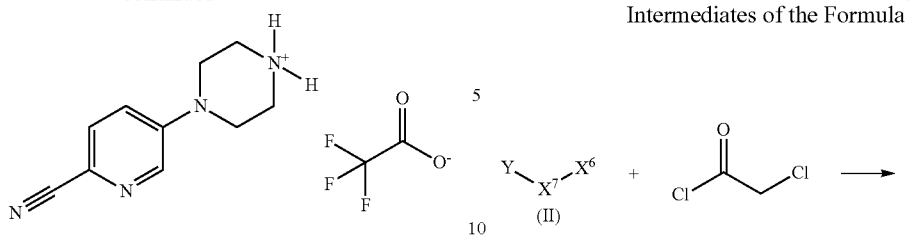

Product from step 1,4-(6-cyano-pyridin-3-yl)-piperazine-1-carboxylic acid tert-butyl ester (1.24 mmol), is dissolved in a mixture of trifluoroacetic acid (1.2 mL) and dichloromethane (3 mL). The mixture is stirred for 2 hours at room temperature and is then concentrated under reduced pressure to afford the desired product as the trifluoroacetate salt (83% overall yield).

A15: Preparation of 5'-trifluoromethyl-3,4,5,6-tetrahydro-2H-[1,2]bipyridinyl-4-yl-ammonium chloride

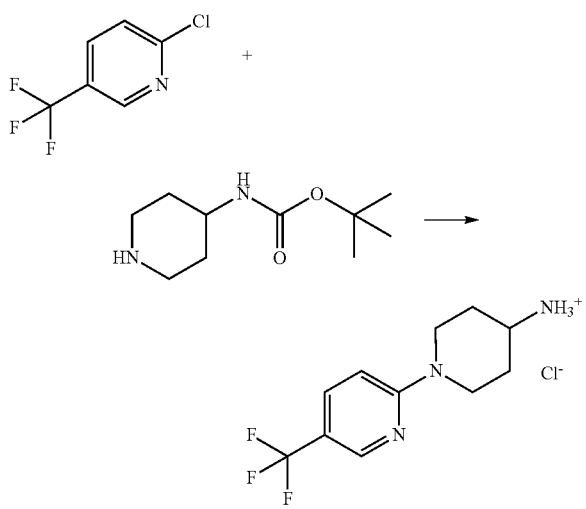

Piperidin-4-yl-carbamic acid tert-butyl ester (3.0 mmol), 2-chloro-5-trifluoromethyl-pyridine (3.0 mmol) and potassium carbonate (8.0 mmol) are dissolved in dimethylsulfoxide (10 mL), and the resulting mixture is stirred at 100° C. for 7 hours. After cooling to room temperature, the mixture is diluted with diethyl ether (30 mL), the precipitate removed by filtration and the filtrate is washed with aqueous saturated sodium hydrogencarbonate solution (2×10 mL). The organic phase is dried over magnesium sulphate, filtered and concentrated under reduced pressure. The residue obtained is dissolved in a 1 to 1 mixture of dichloromethane and trifluoroacetic acid (4 mL) and the reaction mixture is stirred for 1 hour at room temperature. The reaction is then concentrated under reduced pressure, the residue obtained is triturated with a 4N solution of hydrogen hydrochloride in dioxane (5 mL). The suspension is concentrated under reduced pressure and the residue obtained is triturated with diethylether. The solid obtained is filtered and dried reduced pressure to afford the desired product (62% yield).

A16: General Procedure for the Preparation of Intermediates of the Formula (III)

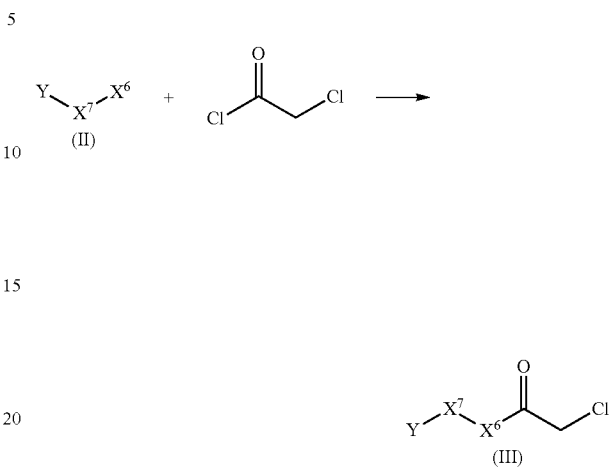

In the compounds of the above reaction scheme Y, $X^6$ and $X^7$ have the same meaning as in formula (I), including their preferred embodiments.

An amine of the formula (II) or a salt thereof (2.0 mmol) (commercially available or prepared according to any of examples A8 to A15) and triethyl amine (3 mmol) are dissolved in dry dichloromethane (4 mL) and chloroacetyl chloride (2.0 mmol) is added. The resulting mixture is stirred at room temperature for 40 minutes and is then diluted with dichloromethane (20 mL). The organic layer is washed with water (15 mL) and aqueous saturated sodium hydrogencarbonate solution (10 mL). The organic layer is then dried over magnesium sulfate, filtered and the filtrate is concentrated under reduced pressure to afford the desired product. In cases traces of unreacted amine are detected, the crude product is dissolved in a minimum volume of dichloromethane and purified by filtration trough a short pad of silica gel, with dichloromethane as the eluent.

The above procedure A16 was used to synthesize compounds A11 to A24, the yield is given for each compound. Procedure A16 and the methods for preparing compounds A11 to A24 can routinely be adapted by a person skilled in the art to make other compounds of the formula (III).

A17: Preparation of 2-chloro-1-[4-(6-methoxy-pyridin-3-yl)-piperazin-1-yl]-ethanone (Yield: 73%)

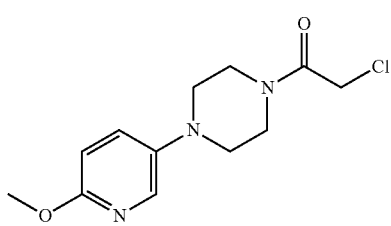 [SMILES: COc1ccc(N2CCN(C(=O)CCl)CC2)cn1]

A18: Preparation of 2-chloro-1-[4-(6-trifluoromethyl-pyridin-3-yl)-piperazin-1-yl]-ethanone (Yield: 78%)

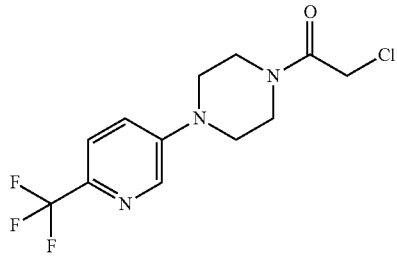 [SMILES: O=C(CCl)N1CCN(c2ccc(C(F)(F)F)nc2)CC1]

A19: Preparation of 6-[4-(2-chloro-acetyl)-piperazin-1-yl]-nicotinonitrile (Yield: 91%)

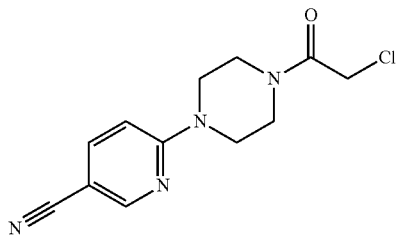 [SMILES: N#Cc1ccc(N2CCN(C(=O)CCl)CC2)nc1]

A20: Preparation of 2-chloro-1-[4-(5-trifluoromethyl-pyridin-2-yl)-piperazin-1-yl]-ethanone (Yield: 96%)

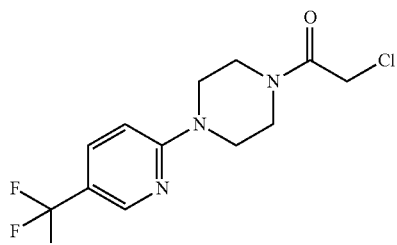

A21: Preparation of 2-chloro-1-[4-(5-chloro-pyridin-2-yl)-piperazin-1-yl]-ethanone (Yield: 55%)

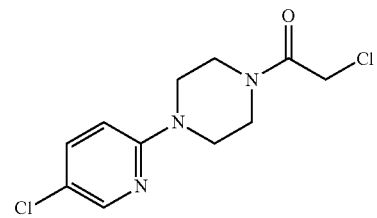 [SMILES: O=C(CCl)N1CCN(c2ccc(Cl)cn2)CC1]

A22: Preparation of 2-chloro-1-[4-(3-chloro-5-trifluoromethyl-pyridin-2-yl)-piperazin-1-yl]-ethanone (Yield: 45%)

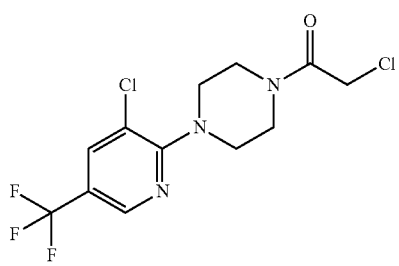 [SMILES: O=C(CCl)N1CCN(c2ncc(C(F)(F)F)cc2Cl)CC1]

A23: Preparation of 2-chloro-1-[4-(5-trifluoromethyl-[1,3,4]thiadiazol-2-yl)-piperazin-1-yl]-ethanone (Yield: 49%)

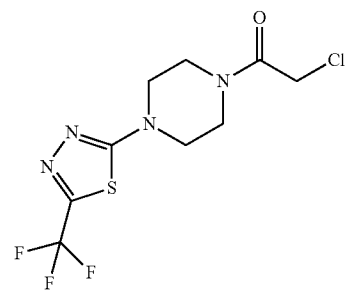 [SMILES: O=C(CCl)N1CCN(c2nnc(C(F)(F)F)s2)CC1]

A24: Preparation of 5-[4-(2-Chloro-acetyl)-piperazin-1-yl]pyridine-2-carbonitrile (Yield: 12%)

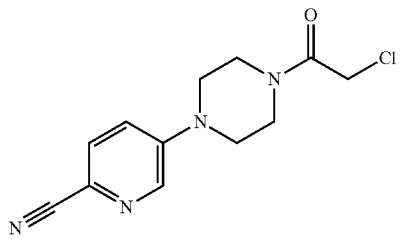 [SMILES: N#Cc1ccc(N2CCN(C(=O)CCl)CC2)cn1]

B) General Procedure for Preparation of Final Products of the Formula (I-B)

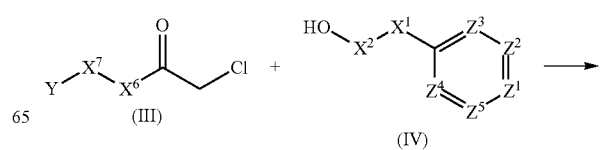

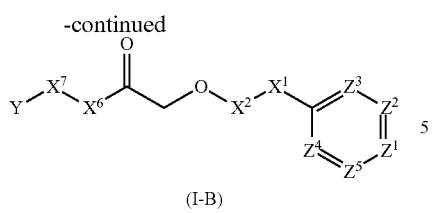

(I-B)

In the compounds (II), (IV) and (I-B) of the above reaction scheme Y, $X^2$ $X^6$, $X^7$, $Z^1$, $Z^2$, $Z^3$, $Z^4$ and $Z^5$ have the same meaning as in formula (I), including their preferred embodiments, and $X^1$ is —O—.

A chloracetyl compound of the formula (III) (0.22 mmol) (commercially available or prepared according to any of examples A16 to A24), a compound of the formula (IV) such as 4-(4-nitro-3-trifluoromethyl-phenoxy)-cyclohexanol (0.20 mmol), and sodium hydride (60% suspension in oil, 0.33 mmol) are suspended at room temperature in a mixture of dry tetrahydrofurane (1 mL) and N,N-dimethylformamide (900 μL). After complete conversion of the starting alcohol as ensured by HPLC monitoring, the reaction mixture is diluted with dichloromethane (10 mL) and is then sequentially washed with water (5 mL), aqueous saturated sodium hydrogencarbonate solution (5 mL) and aqueous saturated sodium chloride solution (5 mL). The organic layer is dried over sodium sulfate, filtered and concentrated under reduced pressure. The crude product obtained is then purified by preparative HPLC.

The above procedure B was used to synthesize compounds B1 to B8, the yield is given for each compound. Procedure B and the methods for preparing compounds B1 to B8 can routinely be adapted by a person skilled in the art to make other compounds of the formula (I) and salts thereof.

B1: Preparation of 1-[4-(6-methoxy-pyridin-3-yl)-piperazin-1-yl]-2-[4-(4-nitro-3-trifluoromethyl-phenoxy)-cyclohexyloxy]-ethanone (Yield: 34%)

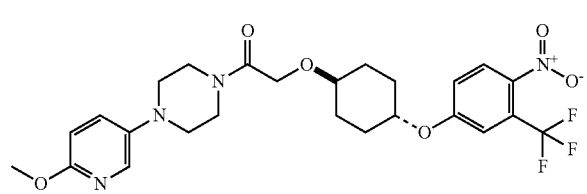

B2: Preparation of 2-[4-(4-nitro-3-trifluoromethyl-phenoxy)-cyclohexyloxy]-1-[4-(6-trifluoromethyl-pyridin-3-yl)-piperazin-1-yl]-ethanone (Yield: 41%)

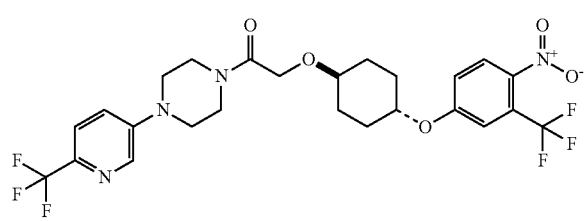

B3: Preparation of 6-(4-{2-[4-(4-nitro-3-trifluoromethyl-phenoxy)-cyclohexyloxy]-acetyl}-piperazin-1-yl)-nicotinonitrile (Yield: 27%)

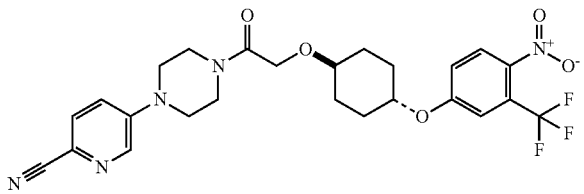

B4: Preparation of 2-[4-(4-nitro-3-trifluoromethyl-phenoxy)-cyclohexyloxy]-1-[4-(5-trifluoromethyl-pyridin-2-yl)-piperazin-1-yl]ethanone (Yield: 36%)

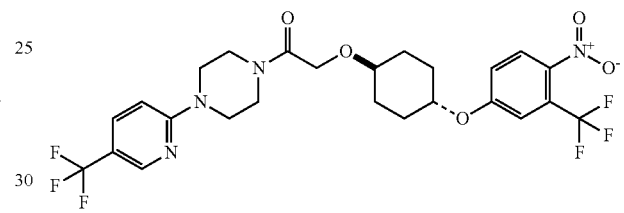

B5: Preparation of 1-[4-(5-chloro-pyridin-2-yl)-piperazin-1-yl]-2-[4-(4-nitro-3-trifluoromethyl-phenoxy)-cyclohexyloxy]-ethanone (Yield: 38%)

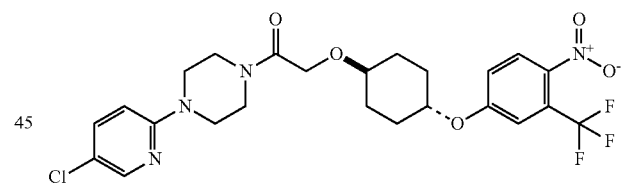

B6: Preparation of 1-[4-(3-chloro-5-trifluoromethyl-pyridin-2-yl)-piperazin-1-yl]-2-[4-(4-nitro-3-trifluoromethyl-phenoxy)-cyclohexyloxy]-ethanone (Yield: 34%)

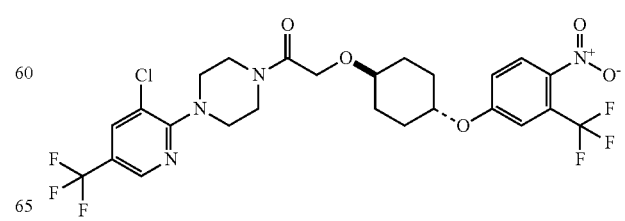

B7: Preparation of 2-[4-(4-nitro-3-trifluoromethyl-phenoxy)-cyclohexyloxy]-1-[4-(5-trifluoromethyl-[1,3,4]thiadiazol-2-yl)-piperazin-1-yl]-ethanone (Yield: 20%)

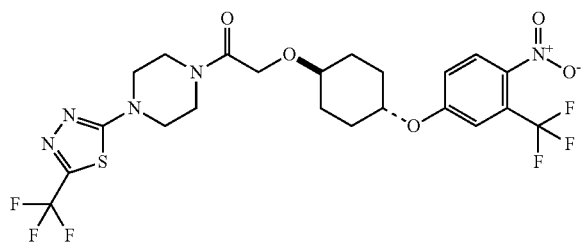

B8: Preparation of 5-(4-{2-[4-(4-nitro-3-trifluoromethyl-phenoxy)-cyclohexyloxy]-acetyl}-piperazin-1-yl)-pyridine-2-carbonitrile (Yield: 78%)

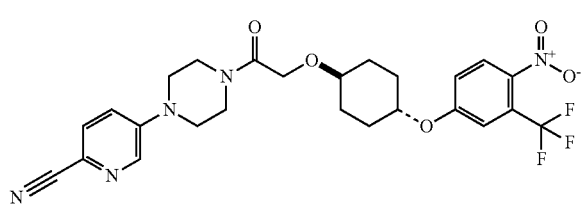

C) General Procedure for Preparation of Final Products of the Formula (I-C)

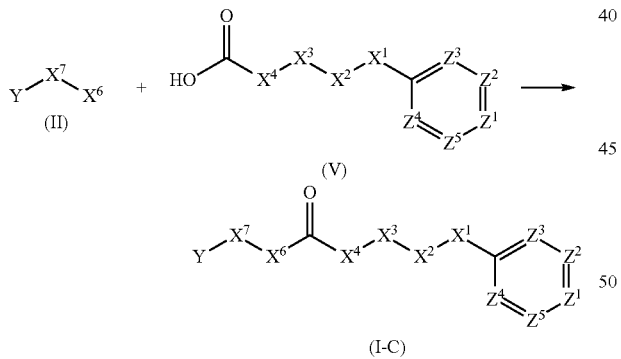

In the compounds (II), (V) and (I-C) of the above reaction scheme Y, $X^2$, $X^3$, $X^4$, $X^6$, $X^7$, $Z^1$, $Z^2$, $Z^3$, $Z^4$ and $Z^5$ have the same meaning as in formula (I), including their preferred embodiments, and $X^1$ is —NH—.

A solution of 2-(1H-benzotriazol-1-yl)-1,1,3,3-tetramethyluronoium hexafluorophosphate (0.22 mmol) in dry N,N-dimethylformamide (1 mL) is added to a solution of a compound of the formula (V) such as [4-(4-nitro-3-trifluoromethyl-phenylamino)-cyclohexyloxy]-acetic acid or [4-(4-nitro-3-difluoromethyl-phenylamino)-cyclohexyloxy]-acetic acid (0.22 mmol) in dry tetrahydrofuran (1 mL). Ethyl-diisopropylamine (1 mmol) is then added, followed by the addition of an amine of the formula (II) or a salt thereof (0.22 mmol) (commercially available or prepared in accordance with any of examples A8 to A15). After 4 hours reaction time, aluminum oxide is added to the reaction mixture and stirring is continued for 1 hour. All solids are removed by filtration and the filtrate is concentrated under reduced pressure to afford the crude product which is then purified by preparative HPLC.

The above procedure C was used to synthesize compounds C1 to C14, the yield is given for each compound. Procedure C and the methods for preparing compounds C1 to C14 can routinely be adapted by a person skilled in the art to make other compounds of the formula (I) and salts thereof.

C1: Preparation of 1-[4-(6-methoxy-pyridin-3-yl)-piperazin-1-yl]-2-[4-(4-nitro-3-trifluoromethyl-phenylamino)-cyclohexyloxy]-ethanone (Yield: 30%)

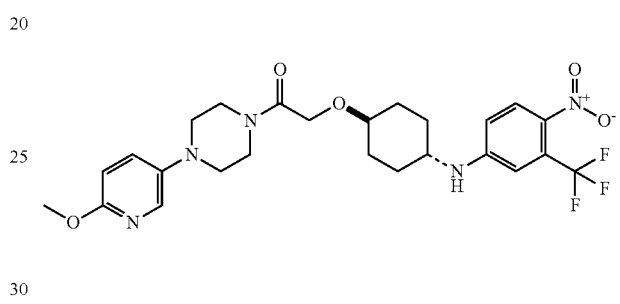

C2: Preparation of 2-[4-(4-nitro-3-trifluoromethyl-phenylamino)-cyclohexyloxy]-1-[4-(6-trifluoromethyl-pyridin-3-yl)-piperazin-1-yl]-ethanone (Yield: 59%)

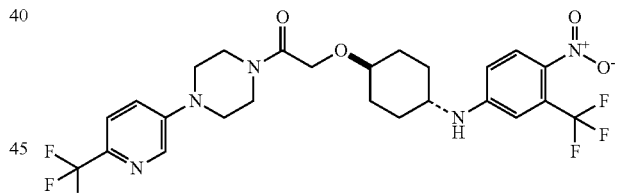

C3: Preparation of 6-(4-{2-[4-(4-nitro-3-trifluoromethyl-phenylamino)-cyclohexyloxy]-acetyl}-piperazin-1-yl)-nicotinonitrile (Yield: 46%)

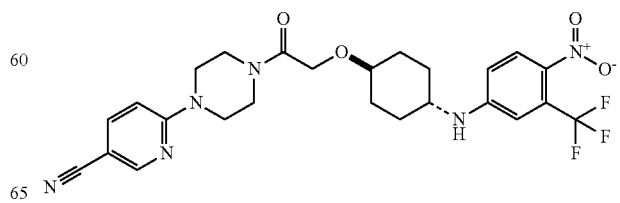

C4: Preparation of 2-[4-(4-nitro-3-trifluoromethyl-phenylamino)-cyclohexyloxy]-1-[4-(5-trifluoromethyl-pyridin-2-yl)-piperazin-1-yl]-ethanone (Yield: 66%)

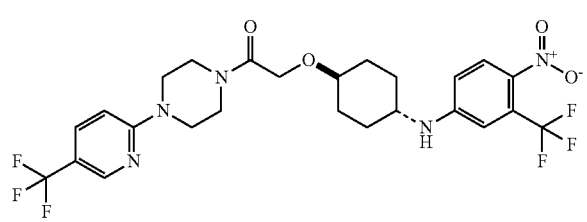

C5: Preparation of 1-[4-(5-chloro-pyridin-2-yl)-piperazin-1-yl]-2-[4-(4-nitro-3-trifluoromethyl-phenylamino)-cyclohexyloxy]-ethanone (Yield: 64%)

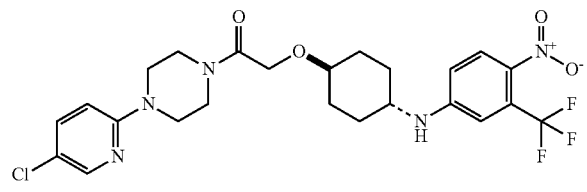

C6: Preparation of 1-[4-(3-chloro-5-trifluoromethyl-pyridin-2-yl)-piperazin-1-yl]-2-[4-(4-nitro-3-trifluoromethyl-phenylamino)-cyclohexyloxy]-ethanone (Yield: 5%)

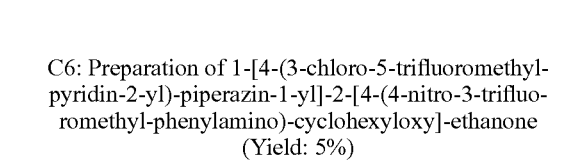

C7: Preparation of 2-[4-(4-nitro-3-trifluoromethyl-phenylamino)-cyclohexyloxy]-1-[4-(5-trifluoromethyl-[1,3,4]thiadiazol-2-yl)-piperazin-1-yl]-ethanone (Yield: 41%)

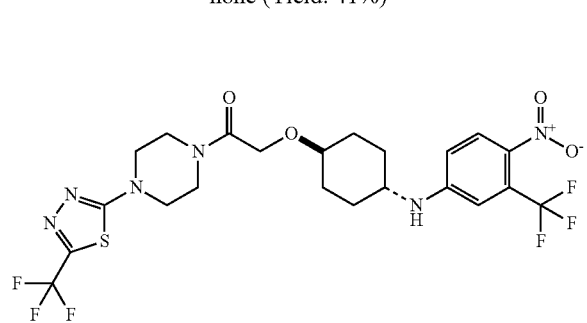

C8: Preparation of 5-(4-{2-[4-(4-nitro-3-trifluoromethyl-phenylamino)-cyclohexyloxy]-acetyl}-piperazin-1-yl)-pyridine-2-carbonitrile (Yield: 55%)

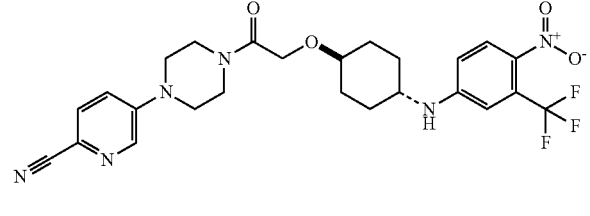

C9: Preparation of 2-[4-(4-nitro-3-trifluoromethyl-phenylamino)-cyclohexyloxy]-N-(5'-trifluoromethyl-3,4,5,6-tetrahydro-2H-[1,2]bipyridinyl-4-yl)-acetamide (Yield: 81%)

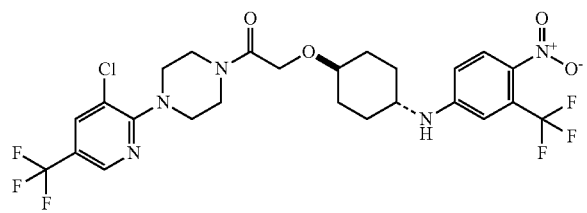

C10: Preparation of 2-[4-(4-nitro-3-trifluoromethyl-phenylamino)-cyclohexyloxy]-1-[4-(2-trifluoromethyl-pyridin-4-ylamino)-piperidin-1-yl]-ethanone (Yield: 51%)

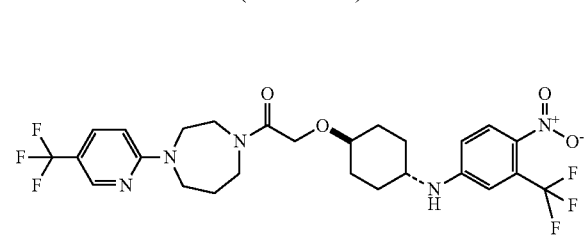

C11: Preparation of 2-[4-(4-nitro-3-trifluoromethyl-phenylamino)-cyclohexyloxy]-1-[4-(5-trifluoromethyl-pyridin-2-yl)-[1,4]diazepan-1-yl]-ethanone (Yield: 75%)

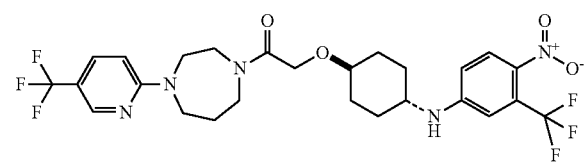

C12: Preparation of 1-[4-(6-difluoromethyl-pyridin-3-yl)-piperazin-1-yl]-2-[4-(4-nitro-3-trifluoromethyl phenylamino)-cyclohexyloxy]-ethanone (Yield: 38%)

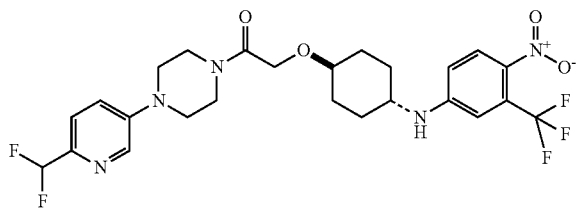

C13: Preparation of 1-[4-(5-difluoromethyl-pyridin-2-yl)-piperazin-1-yl]-2-[4-(4-nitro-3-trifluoromethyl-phenylamino)-cyclohexyloxy]-ethanone (Yield: 36%)

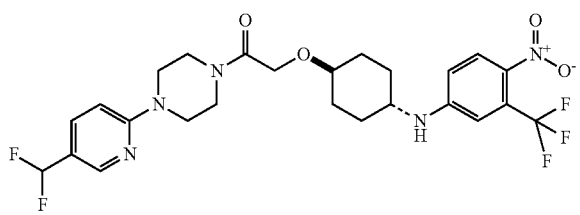

C14: Preparation of 2-[4-(3-difluoromethyl-4-nitro-phenylamino)-cyclohexyloxy]-1-[4-(5-difluoromethyl-pyridin-2-yl)-piperazin-1-yl]-ethanone (Yield: 38%)

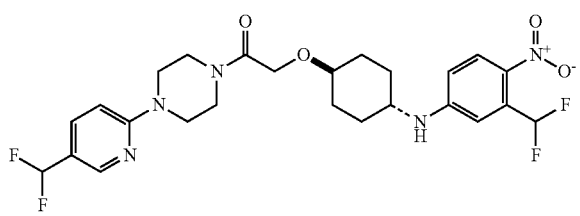

D) General Procedure for Preparation of Final Products of the Formula (I-D)

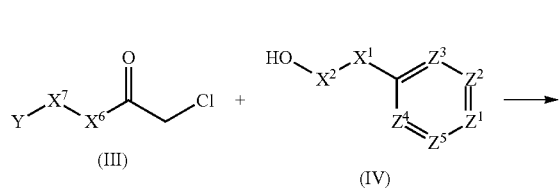

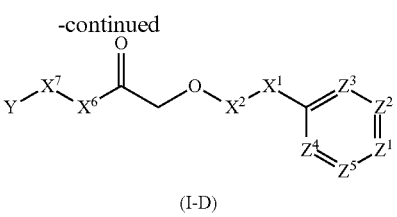

(I-D)

In the compounds (III), (IV) and (I-D) of the above reaction scheme Y, $X^2$, $X^6$, $X^7$, $Z^1$, $Z^2$, $Z^3$, $Z^4$ and $Z^5$ have the same meaning as in formula (I), including their preferred embodiments, and $X^1$ is —O—.

A chloracetyl compound of the formula (III) (0.14 mmol) (commercially available or prepared according to any of examples A16 to A24), a compound of the formula (IV) such as 4-(4-hydroxy-cyclohexyloxy)-2-trifluoromethyl-benzonitrile (0.12 mmol), and sodium hydride (60% suspension in oil, 0.33 mmol) are suspended at room temperature in a mixture of dry tetrahydrofurane (1 mL) and N,N-dimethylformamide (900 µL) and allowed to stir at room temperature overnight. The reaction mixture is then diluted with dichloromethane (10 mL) and is sequentially washed with water (5 mL), aqueous saturated sodium hydrogencarbonate solution (5 mL) and aqueous saturated sodium chloride solution (5 mL). The organic layer is dried over sodium sulfate, filtered and concentrated under reduced pressure to afford the crude product which is then purified by preparative HPLC.

The above procedure D was used to synthesize compounds D1 to D8, the yield is given for each compound. Procedure D and the methods described for preparing compounds D1 to D8 can routinely be adapted by a person skilled in the art to make other compounds of the formula (I) and salts thereof.

D1: Preparation of 4-(4-{2-[4-(6-methoxy-pyridin-3-yl)-piperazin-1-yl]-2-oxo-ethoxy}-cyclohexyloxy)-2-trifluoromethyl-benzonitrile (Yield: 25%)

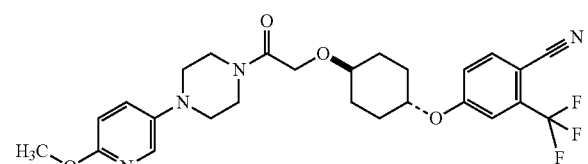

D2: Preparation of 4-(4-{2-oxo-2-[4-(6-trifluoromethyl-pyridin-3-yl)-piperazin-1-yl]-ethoxy}-cyclohexyloxy)-2-trifluoromethyl-benzonitrile (Yield: 49%)

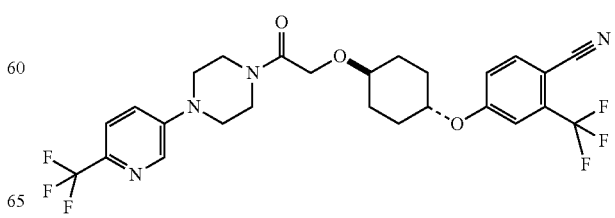

D3: Preparation of 6-(4-{2-[4-(4-cyano-3-trifluoromethyl-phenoxy)-cyclohexyloxy]-acetyl}-piperazin-1-yl)-nicotinonitrile (Yield: 31%)

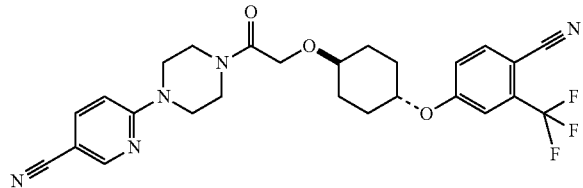

D4: Preparation of 4-(4-{2-oxo-2-[4-(5-trifluoromethyl-pyridin-2-yl)-piperazin-1-yl]-ethoxy}-cyclohexyloxy)-2-trifluoromethyl-benzonitrile (Yield: 43%)

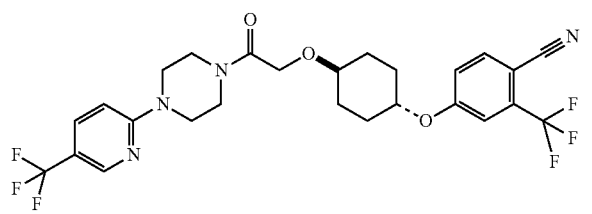

D5: Preparation of 4-(4-{2-[4-(5-chloro-pyridin-2-yl)-piperazin-1-yl]-2-oxo-ethoxy}-cyclohexyloxy)-2-trifluoromethyl-benzonitrile (Yield: 29%)

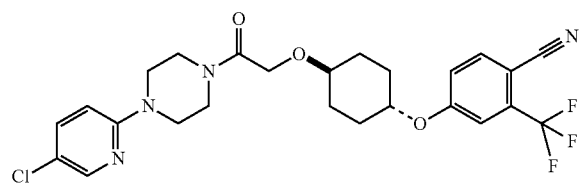

D6: Preparation of 4-(4-{2-[4-(3-chloro-5-trifluoromethyl-pyridin-2-yl)-piperazin-1-yl]-2-oxo-ethoxy}-cyclohexyloxy)-2-trifluoromethyl-benzonitrile (Yield: 19%)

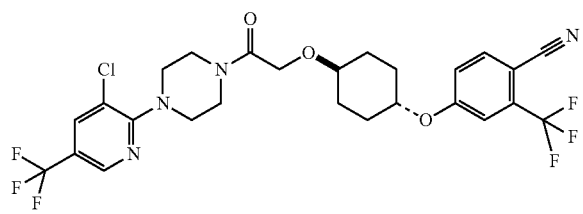

D7: Preparation of 4-(4-{2-oxo-2-[4-(5-trifluoromethyl-[1,3,4]thiadiazol-2-yl)-piperazin-1-yl]-ethoxy}-cyclohexyloxy)-2-trifluoromethyl-benzonitrile (Yield: 24%)

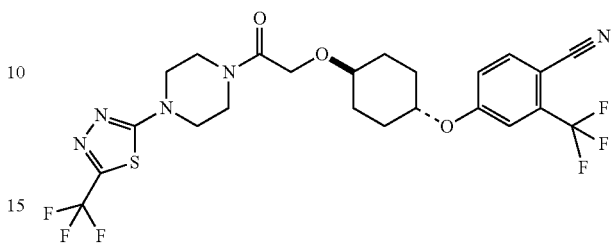

D8: Preparation of 5-(4-{2-[4-(4-cyano-3-trifluoromethyl-phenoxy)-cyclohexyloxy]-acetyl}-piperazin-1-yl)-pyridine-2-carbonitrile (Yield: 8%)

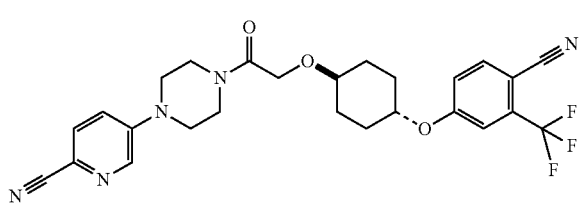

E) General Procedure for Preparation of Final Products of the Formula (I-E)

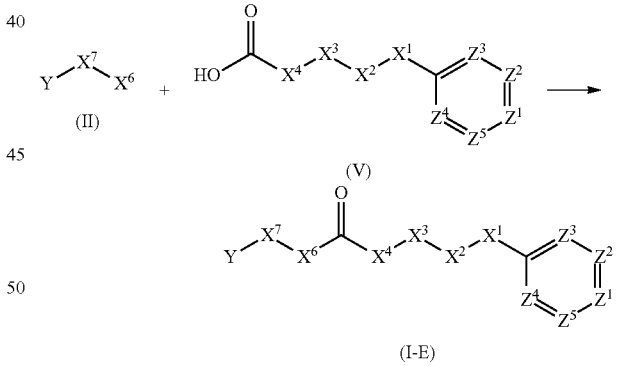

In the compounds (II), (V) and (I-E) of the above reaction scheme Y, $X^2$, $X^3$, $X^4$, $X^6$, $X^7$, $Z^1$, $Z^2$, $Z^3$, $Z^4$ and $Z^5$ have the same meaning as in formula (I), including their preferred embodiments, and $X^1$ is —NH—.

A solution of 2-(1H-benzotriazol-1-yl)-1,1,3,3-tetramethyluronium hexafluorophosphate (0.22 mmol) in dry N,N-dimethylformamide (1 mL) is added to a solution of a compound of the formula (V) such as [4-(4-cyano-3-trifluoromethyl-phenylamino)-cyclohexyloxy]-acetic acid (0.22 mmol) in dry tetrahydrofuran (1 mL). Ethyl-diisopropylamine (1 mmol) is then added, followed by the addition of an amine of the formula (II) or a salt thereof (0.22 mmol) (commercially available or prepared in accordance with any of examples A8 to A15). After 4 hours of reaction time, aluminium oxide is added to the reaction mixture and stirring is continued for 1 hour. All solids are then removed by filtration and the filtrate is concentrated under reduced pressure to afford the crude product which is finally purified by preparative HPLC.

The above procedure E was used to synthesize compounds E1 to E11, the yield is given for each compound. Procedure E and the methods for preparing compounds E1 to E11 can routinely be adapted by a person skilled in the art to make other compounds of the formula (I) and salts thereof.

E1: Preparation of 4-(4-{2-[4-(6-methoxy-pyridin-3-yl)-piperazin-1-yl]-2-oxo-ethoxy}-cyclohexylamino)-2-trifluoromethyl-benzonitrile (Yield: 43%)

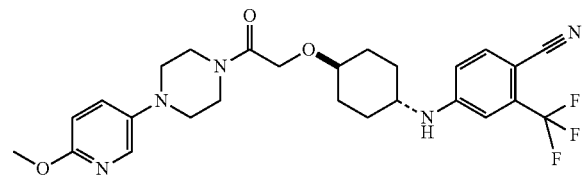

E2: Preparation of 4-(4-{2-oxo-2-[4-(6-trifluoromethyl-pyridin-3-yl)-piperazin-1-yl]-ethoxy}-cyclohexylamino)-2-trifluoromethyl-benzonitrile (Yield: 68%)

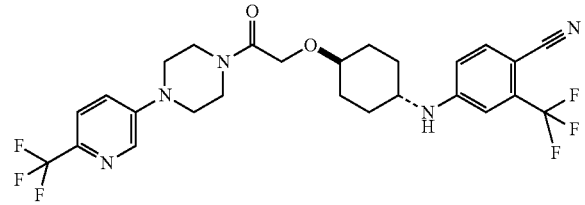

E3: Preparation of 6-(4-{2-[4-(4-cyano-3-trifluoromethyl-phenylamino)-cyclohexyloxy]-acetyl}-piperazin-1-yl)-nicotinonitrile (Yield: 76%)

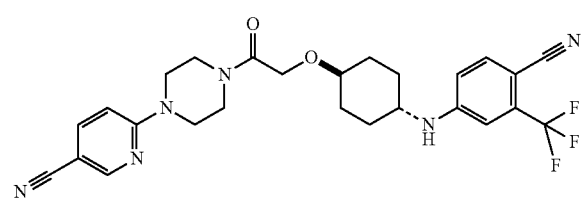

E4: Preparation of 4-(4-{2-oxo-2-[4-(5-trifluoromethyl-pyridin-2-yl)-piperazin-1-yl]-ethoxy}-cyclohexylamino)-2-trifluoromethyl-benzonitrile (Yield: 62%)

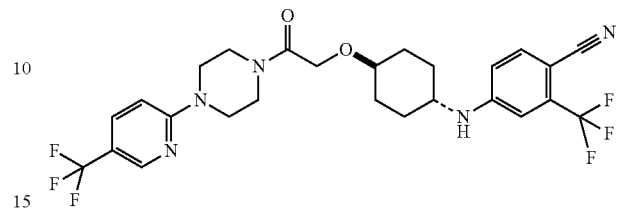

E5: Preparation of 4-(4-{2-[4-(5-chloro-pyridin-2-yl)-piperazin-1-yl]-2-oxo-ethoxy}-cyclohexylamino)-2-trifluoromethyl-benzonitrile (Yield: 70%)

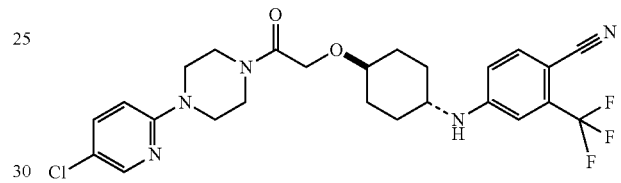

E6: Preparation of 4-(4-{2-[4-(3-chloro-5-trifluoromethyl-pyridin-2-yl)-piperazin-1-yl]-2-oxo-ethoxy}-cyclohexylamino)-2-trifluoromethyl-benzonitrile (Yield: 77%)

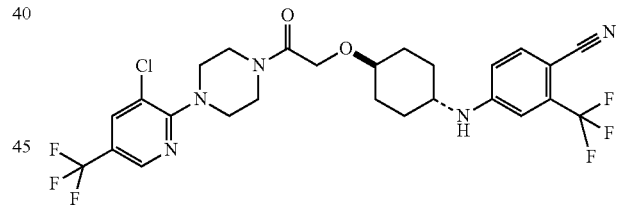

E7: Preparation of 4-(4-{2-oxo-2-[4-(5-trifluoromethyl-[1,3,4]thiadiazol-2-yl)-piperazin-1-yl]-ethoxy}-cyclohexylamino)-2-trifluoromethyl-benzonitrile (Yield: 60%)

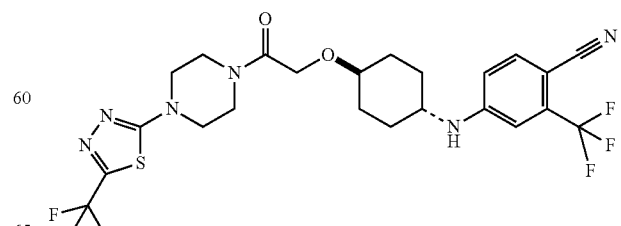

E8: Preparation of 5-(4-{2-[4-(4-cyano-3-trifluoromethyl-phenylamino)-cyclohexyloxy]-acetyl}-piperazin-1-yl)-pyridine-2-carbonitrile (Yield: 55%)

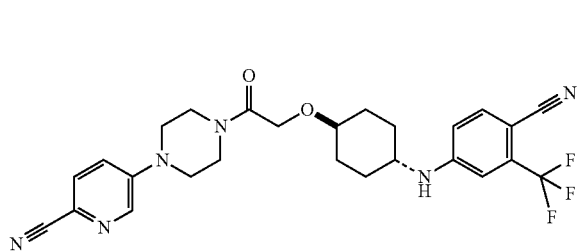

E9: Preparation of 2-[4-(4-cyano-3-trifluoromethyl-phenylamino)-cyclohexyloxy]-N-(5'-trifluoromethyl-3,4,5,6-tetrahydro-2H-[1,2]bipyridinyl-4-yl)-acetamide (Yield: 81%)

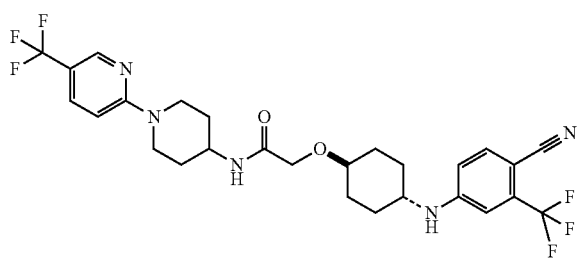

E10: Preparation of 4-(4-{2-oxo-2-[4-(2-trifluoromethyl-pyridin-4-ylamino)-piperidin-1-yl]-ethoxy}-cyclohexylamino)-2-trifluoromethyl-benzonitrile (Yield: 70%)

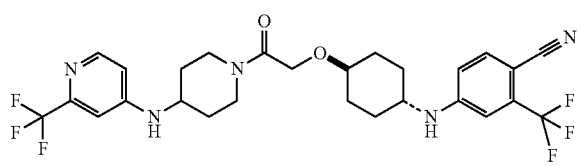

E11: Preparation of 4-(4-{2-oxo-2-[4-(5-trifluoromethyl-pyridin-2-yl)-[1,4]diazepan-1-yl]-ethoxy}-cyclohexylamino)-2-trifluoromethyl-benzonitrile (Yield: 84%)

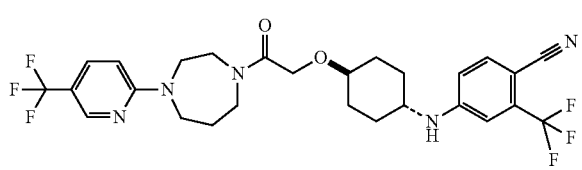

F) General Procedure for Preparation of Final Products of the Formula (I-F)

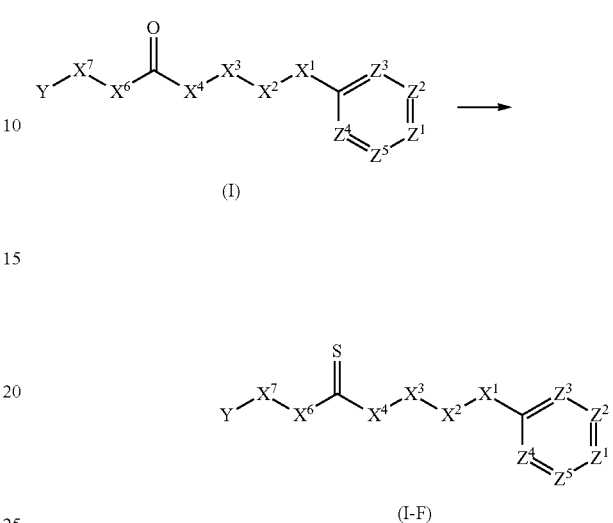

In the compounds of the above reaction scheme Y, $X^1$, $X^2$, $X^3$, $X^4$, $X^6$, $X^7$, $Z^1$, $Z^2$, $Z^3$, $Z^4$ and $Z^5$ have the same meaning as in formula (I), including their preferred embodiments.

A compound of the formula (I) wherein $X^5$=CO (0.014 to 0.046 mmol) (prepared according to any of the examples in sections B, C, D, or E), was dissolved in toluene (1 mL) and Lawesson's reagent is added (0.5 equivalent). The resulting mixture is heated to 120° C. and for 2 hours and is then allowed to reach room temperature overnight. The reaction mixture is then concentrated under reduced pressure and the crude product obtained is purified by preparative HPLC.

The above procedure F was used to synthesize compounds F1 to F30 of the formula (I-F) wherein $X^5$=CS, the yield is given for each compound. Procedure F and the methods for preparing compounds F1 to F30 can routinely be adapted by a person skilled in the art to make other compounds of the formula (I) and salts thereof.

F1: Preparation of 1-[4-(6-methoxy-pyridin-3-yl)-piperazin-1-yl]-2-[4-(4-nitro-3-trifluoromethyl-phenoxy)-cyclohexyloxy]-ethanethione (Yield: 49%)

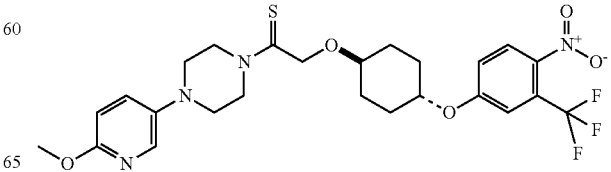

F2: Preparation of 2-[4-(4-nitro-3-trifluoromethyl-phenoxy)-cyclohexyloxy]-1-[4-(6-trifluoromethyl-pyridin-3-yl)-piperazin-1-yl]-ethanethione (Yield: 52%)

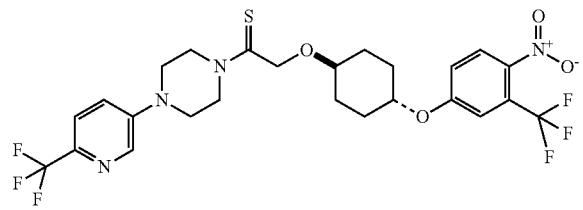

F3: Preparation of 6-(4-{2-[4-(4-nitro-3-trifluoromethyl-phenoxy)-cyclohexyloxy]-thioacetyl}-piperazin-1-yl)-nicotinonitrile (Yield: 63%)

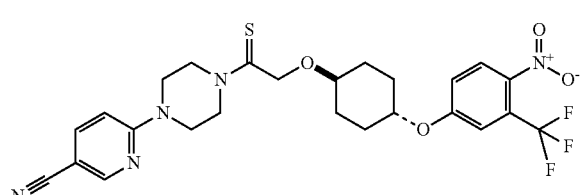

F4: Preparation of 2-[4-(4-nitro-3-trifluoromethyl-phenoxy)-cyclohexyloxy]-1-[4-(5-trifluoromethyl-pyridin-2-yl)-piperazin-1-yl]-ethanethione (Yield: 68%)

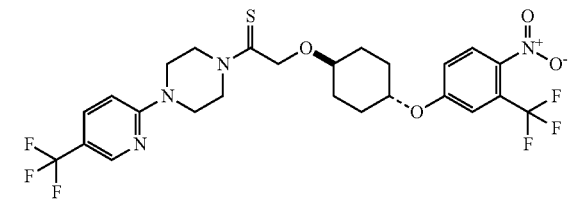

F5: Preparation of 1-[4-(5-chloro-pyridin-2-yl)-piperazin-1-yl]-2-[4-(4-nitro-3-trifluoromethyl-phenoxy)-cyclohexyloxy]-ethanethione (Yield: 67%)

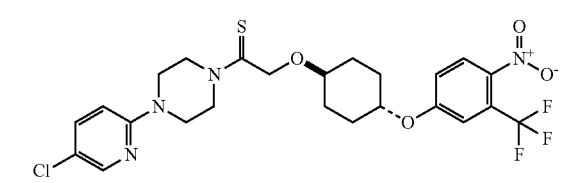

F6: Preparation of 1-[4-(3-chloro-5-trifluoromethyl-pyridin-2-yl)-piperazin-1-yl]-2-[4-(4-nitro-3-trifluoromethyl-phenoxy)-cyclohexyloxy]-ethanethione (Yield: 68%)

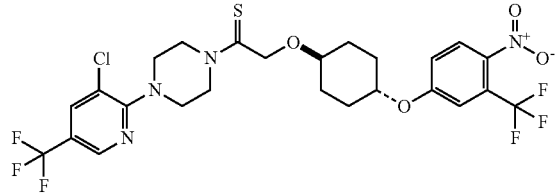

F7: Preparation of 2-[4-(4-nitro-3-trifluoromethyl-phenoxy)-cyclohexyloxy]-1-[4-(5-trifluoromethyl-[1,3,4]thiadiazol-2-yl)-piperazin-1-yl]-ethanethione (Yield: 68%)

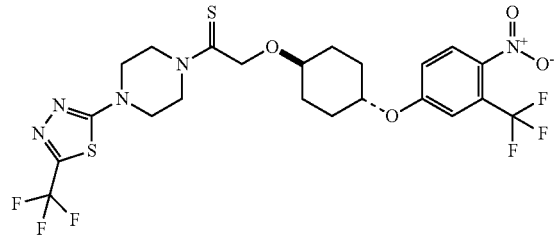

F8: Preparation of 4-(4-{2-[4-(6-methoxy-pyridin-3-yl)-piperazin-1-yl]-2-thioxo-ethoxy}-cyclohexyloxy)-2-trifluoromethyl-benzonitrile (Yield: 28%)

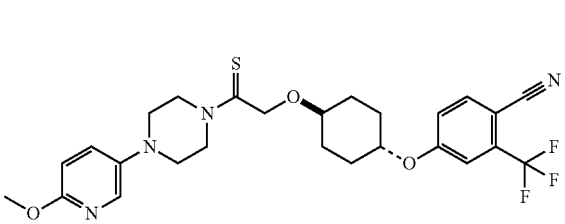

F9: Preparation of 4-(4-{2-thioxo-2-[4-(6-trifluoromethyl-pyridin-3-yl)-piperazin-1-yl]-ethoxy}-cyclohexyloxy)-2-trifluoromethyl-benzonitrile (Yield: 79%)

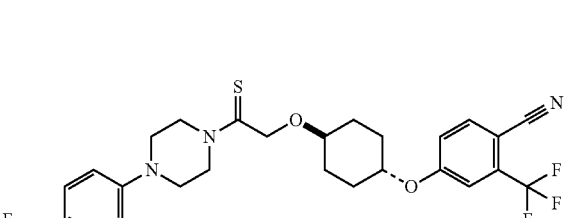

F10: Preparation of 6-(4-{2-[4-(4-cyano-3-trifluoromethyl-phenoxy)-cyclohexyloxy]-thioacetyl}-piperazin-1-yl)-nicotinonitrile (Yield: 73%)

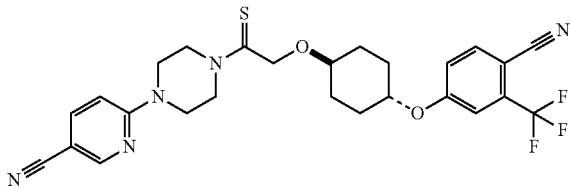

F11: Preparation of 4-(4-{2-thioxo-2-[4-(5-trifluoromethyl-pyridin-2-yl)-piperazin-1-yl]-ethoxy}-cyclohexyloxy)-2-trifluoromethyl-benzonitrile (Yield: 73%)

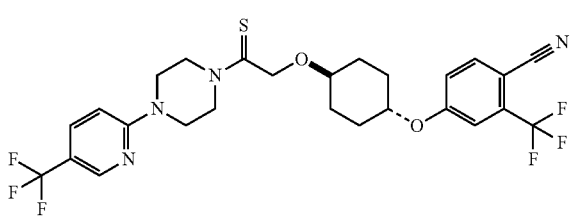

F12: Preparation of 4-(4-{2-[4-(5-chloro-pyridin-2-yl)-piperazin-1-yl]-2-thioxo-ethoxy}-cyclohexyloxy)-2-trifluoromethyl-benzonitrile (Yield: 80%)

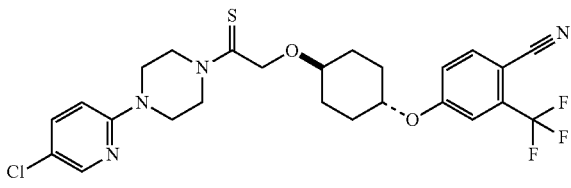

F13: Preparation of 4-(4-{2-[4-(3-chloro-5-trifluoromethyl-pyridin-2-yl)-piperazin-1-yl]-2-thioxo-ethoxy}-cyclohexyloxy)-2-trifluoromethyl-benzonitrile (Yield: 57%)

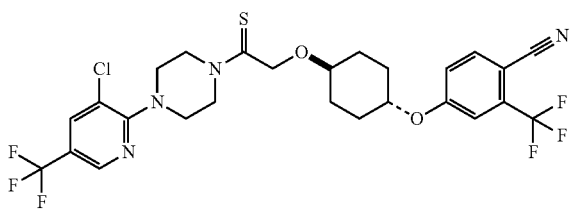

F14: Preparation of 4-(4-{2-thioxo-2-[4-(5-trifluoromethyl-[1,3,4]thiadiazol-2-yl)-piperazin-1-yl]-ethoxy}-cyclohexyloxy)-2-trifluoromethyl-benzonitrile (Yield: 50%)

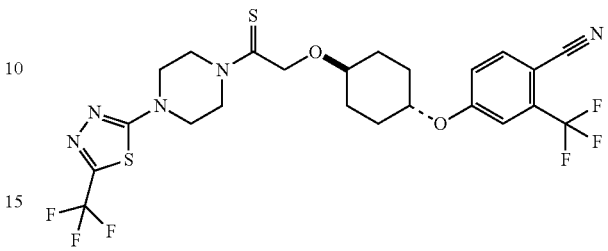

F15: Preparation of 1-[4-(6-methoxy-pyridin-3-yl)-piperazin-1-yl]-2-[4-(4-nitro-3-trifluoromethyl-phenylamino)-cyclohexyloxy]-ethanethione (Yield: 72%)

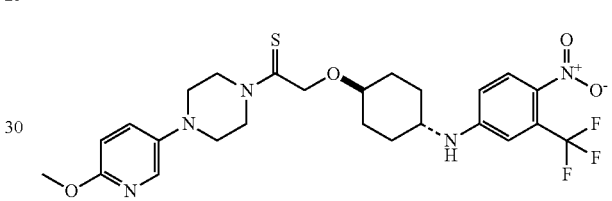

F16: Preparation of 2-[4-(4-nitro-3-trifluoromethyl-phenylamino)-cyclohexyloxy]-1-[4-(6-trifluoromethyl-pyridin-3-yl)-piperazin-1-yl]-ethanethione (Yield: 93%)

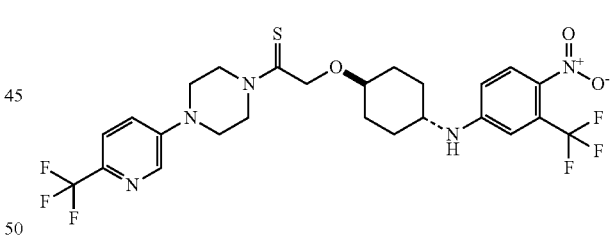

F17: Preparation of 6-(4-{2-[4-(4-nitro-3-trifluoromethyl-phenylamino)-cyclohexyloxy]-thioacetyl}-piperazin-1-yl)-nicotinonitrile (Yield: 48%)

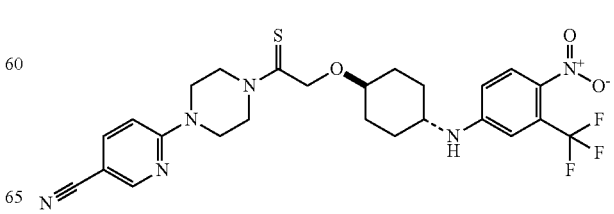

F18: Preparation of 2-[4-(4-nitro-3-trifluoromethyl-phenylamino)-cyclohexyloxy]-1-[4-(5-trifluoromethyl-pyridin-2-yl)-piperazin-1-yl]-ethanethione (Yield: 88%)

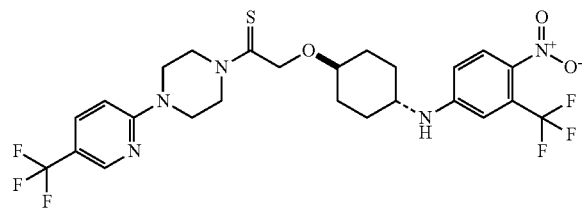

F19: Preparation of 1-[4-(5-chloro-pyridin-2-yl)-piperazin-1-yl]-2-[4-(4-nitro-3-trifluoromethyl-phenylamino)-cyclohexyloxy]-ethanethione (Yield: 82%)

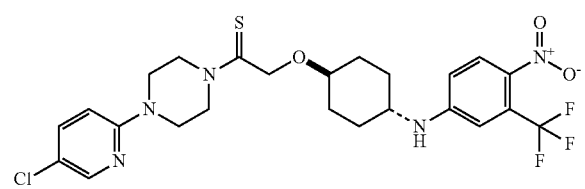

F20: Preparation of 2-[4-(4-nitro-3-trifluoromethyl-phenylamino)-cyclohexyloxy]-1-[4-(5-trifluoromethyl-[1,3,4]thiadiazol-2-yl)-piperazin-1-yl]-ethanethione (Yield: 79%)

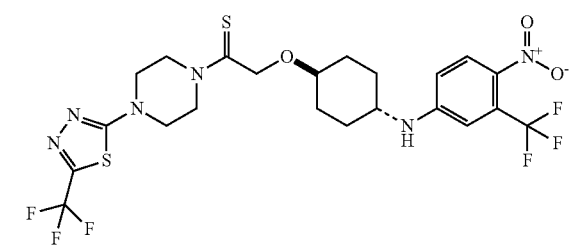

F21: Preparation of 5-(4-{2-[4-(4-nitro-3-trifluoromethyl-phenylamino)-cyclohexyloxy]-thioacetyl}-piperazin-1-yl)-pyridine-2-carbonitrile (Yield: 75%)

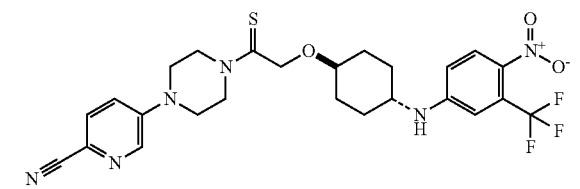

F22: Preparation of 1-[4-(3-chloro-5-trifluoromethyl-pyridin-2-yl)-piperazin-1-yl]-2-[4-(4-nitro-3-trifluoromethyl-phenylamino)-cyclohexyloxy]-ethanethione (Yield: 80%)

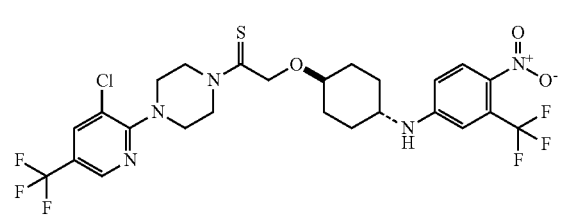

F23: Preparation of 4-(4-{2-[4-(6-methoxy-pyridin-3-yl)-piperazin-1-yl]-2-thioxo-ethoxy}-cyclohexylamino)-2-trifluoromethyl-benzonitrile (Yield: 58%)

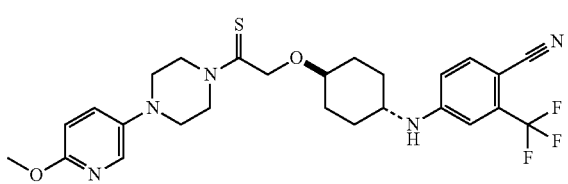

F24: Preparation of 4-(4-{2-thioxo-2-[4-(6-trifluoromethyl-pyridin-3-yl)-piperazin-1-yl]-ethoxy}-cyclohexylamino)-2-trifluoromethyl-benzonitrile (Yield: 92%)

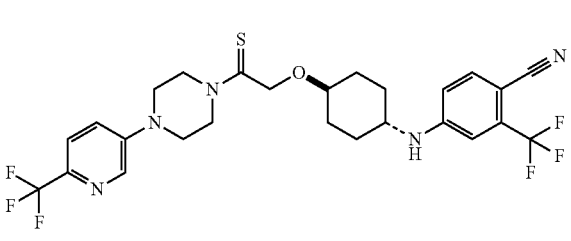

F25: Preparation of 6-(4-{2-[4-(4-cyano-3-trifluoromethyl-phenylamino)-cyclohexyloxy]-thioacetyl}-piperazin-1-yl)-nicotinonitrile (Yield: 69%)

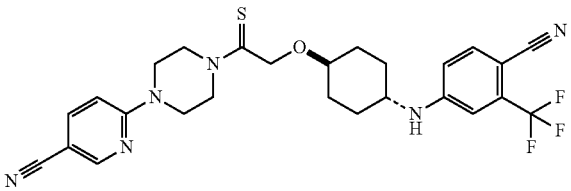

F26: Preparation of 4-(4-{2-thioxo-2-[4-(5-trifluoromethyl-pyridin-2-yl)-piperazin-1-yl]-ethoxy}-cyclohexylamino)-2-trifluoromethyl-benzonitrile (Yield: 84%)

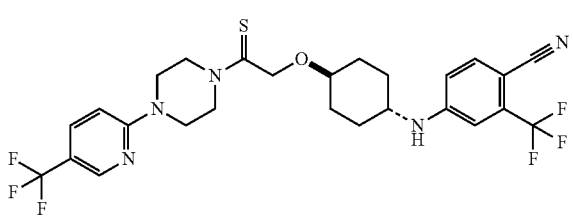

F27: Preparation of 4-(4-{2-[4-(5-chloro-pyridin-2-yl)-piperazin-1-yl]-2-thioxo-ethoxy}-cyclohexylamino)-2-trifluoromethyl-benzonitrile (Yield: 86%)

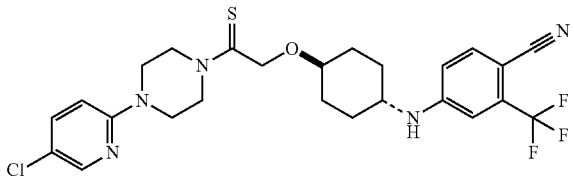

F28: Preparation of 4-(4-{2-[4-(3-chloro-5-trifluoromethyl-pyridin-2-yl)-piperazin-1-yl]-2-thioxo-ethoxy}-cyclohexylamino)-2-trifluoromethyl-benzonitrile (Yield: 84%)

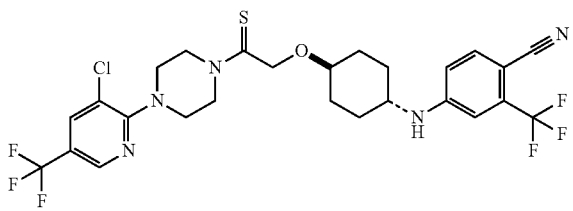

F29: Preparation of 4-(4-{2-thioxo-2-[4-(5-trifluoromethyl-[1,3,4]thiadiazol-2-yl)-piperazin-1-yl]-ethoxy}-cyclohexylamino)-2-trifluoromethyl-benzonitrile (Yield: 66%)

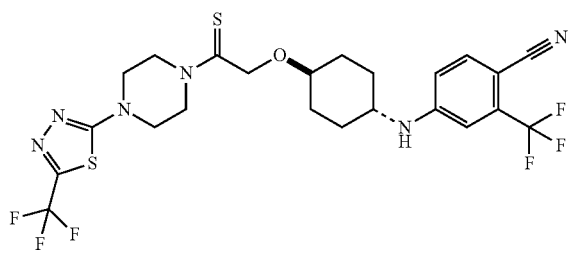

F30: Preparation of 5-(4-{2-[4-(4-cyano-3-trifluoromethyl-phenylamino)-cyclohexyloxy]-thioacetyl}-piperazin-1-yl)-pyridine-2-carbonitrile (Yield: 68%)

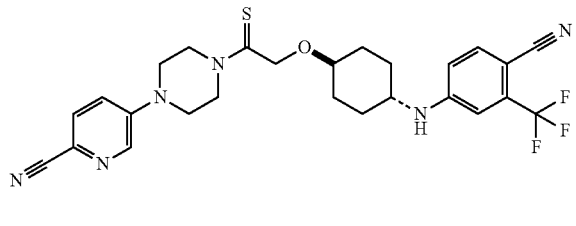

G) Analytics a) HPLC Methods

System I

In some instances, the compound analysis was conducted using an HPLC/MSD 1100 (Agilent, Santa Clara, Calif., USA) having a binary pump (G1312A) with a degasser (G1379A), a well plate sampler (G1367A), a column oven (G1316A), a diode array detector (G1315B), a mass detector (G1946D SL) with an ESI-source, and an evaporating light detector (Sedex 75).

Protocol I-A

The column used for this protocol was an Atlantis dC18 (Waters, Milford, Mass., USA), having a 4.6 mm diameter, a 50 mm length, and 3 μm packing. The column was operated at 30° C. (ambient temperature). The injection volume was 2.0 μL, the flow rate was 1.0 ml/min, and the run time was 10 min (equilibration included). Two eluents were used with the following gradients:

| Time (min) | Solvent A (%) water/formic acid, 99.9/0.1 (v/v) | Solvent B (%) acetonitrile/formic acid, 99.9/0.1 (v/v) |
|---|---|---|
| 0.0 | 95 | 5 |
| 1.0 | 95 | 5 |
| 5.0 | 2 | 98 |
| 7.0 | 2 | 98 |

The samples were diluted in a 1:1 mixture of solvents A and B before analysis. The detection methods were UV at 210 and 254 nm; ESI/MS (100-1000 m/z), positive ions; and ELSD (Sedex 75).

Protocol I-B

The column used for this protocol was a Zorbax SB-C18 (Agilent), having a 4.6 mm diameter, a 30 mm length, and 3.5 μm packing. The column was operated at 30° C. (ambient temperature). The injection volume was 5.0 μL, the flow rate was 1.0 ml/min, and the run time was 8 min (equilibration included). Two eluents were used with the following gradients:

| Time (min) | Solvent A (%) water/formic acid, 99.9/0.1 (v/v) | Solvent B (%) acetonitrile/formic acid, 99.9/0.1 (v/v) |
|---|---|---|
| 0.0 | 90 | 10 |
| 0.2 | 90 | 10 |
| 4.2 | 2 | 98 |
| 5.5 | 2 | 98 |

The samples were diluted in a 1:1 mixture of solvents A and B before analysis. The detection methods were UV at 210 and 254 nm; ESI/MS (100-1000 m/z), positive ions; and ELSD (Sedex 75).

Protocol I-C

The column used for this protocol was a Chromolith Fast Gradient, RP-18e (VWR int.), having a 2.0 mm diameter, and a 50 mm length. The column was operated at 35° C. temperature. The injection volume was 1.0 µL, the flow rate was 1.2 ml/min, and the run time was 3.5 min (equilibration included). Two eluents were used with the following gradients:

| Time (min) | Solvent A (%) water/formic acid, 99.9/0.1 (v/v) | Solvent B (%) acetonitrile/formic acid, 99.9/0.1 (v/v) |
|---|---|---|
| 0.0 | 90 | 10 |
| 2.0 | 0 | 100 |
| 2.7 | 0 | 100 |
| 3.0 | 90 | 10 |

The samples were diluted in a 1:1 mixture of solvents A and B before analysis. The detection methods were UV at 210 and 254 nm; ESI/MS (100-1000 m/z), positive ions; and ELSD (Sedex 75).

System II

In some other instances, the compound analysis was conducted using an HPLC/MSD Trap 1100 (Agilent, Santa Clara, Calif., USA) having a binary pump (G1312A) with a degasser (G1379A), a well plate sampler (G1367A), a column oven (G1316A), a diode array detector (G1315B), a mass detector (G2445D) with either an ESI- or an APCI-source.

Protocol II-A

The column used for this protocol was a XBridge C18 (Waters, Milford, Mass., USA), having a 4.6 mm diameter, a 50 mm length, and 2.5 µm packing. The column was operated at 40° C. temperature. The injection volume was 2.0 µL, the flow rate was 1.0 ml/min, and the run time was 10 min (equilibration included). Two eluents were used with the following gradients:

| Time (min) | Solvent A (%) water/ammonia, 99.9/0.1 (v/v) | Solvent B (%) acetonitrile |
|---|---|---|
| 0.0 | 90 | 10 |
| 4.0 | 0 | 100 |
| 5.0 | 0 | 100 |
| 5.5 | 90 | 10 |

The samples were diluted in a 1:1 mixture of solvents A and B before analysis. The detection methods were UV at 210 and 254 nm; APCI/MS (100-1500 m/z), positive ions.

Protocol II-B

The column used for this protocol was a Zorbax SB-C18 (Agilent), having a 4.6 mm diameter, a 30 mm length, and 3.5 µm packing. The column was operated at 30° C. (ambient temperature). The injection volume was 5.0 µL, the flow rate was 1.0 ml/min, and the run time was 8 min (equilibration included). Two eluents were used with the following gradients:

| Time (min) | Solvent A (%) water/formic acid, 99.9/0.1 (v/v) | Solvent B (%) acetonitrile/formic acid, 99.9/0.1 (v/v) |
|---|---|---|
| 0.0 | 90 | 10 |
| 0.2 | 90 | 10 |
| 4.2 | 2 | 98 |
| 5.5 | 2 | 98 |

The samples were diluted in a 1:1 mixture of solvents A and B before analysis. The detection methods were UV at 210 and 254 nm; APCI/MS (80-1000 m/z), positive ions.

b) Analytical Data

Tables II and III provide for each compound the structure, the HPLC-method used for analysis, the HPLC retention time (RT) in minutes (min), the observed MS signal (m/z), and calculated molecular weight MW (gram/mol).

TABLE II

| Compound | Structure | HPLC Method | RT (min) | m/z | MW calculated (g/mol) |
|---|---|---|---|---|---|
| A1 | 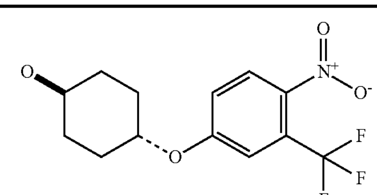 | I-B | 3.765 | none | 305.3 |

TABLE II-continued

| Compound | Structure | HPLC Method | RT (min) | m/z | MW calculated (g/mol) |
|---|---|---|---|---|---|
| A2 | 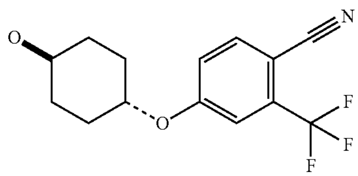 [SMILES: N#Cc1ccc(O[C@H]2CC[C@H](O)CC2)cc1C(F)(F)F] | I-B | 3.144 | none | 285.3 |
| A5 | 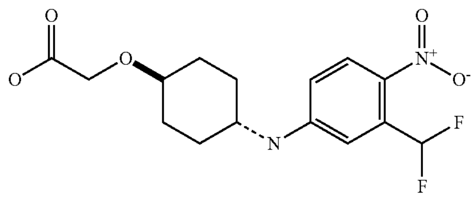 | I-C | 1.632 | 345.1 | 344.3 |
| A6 | 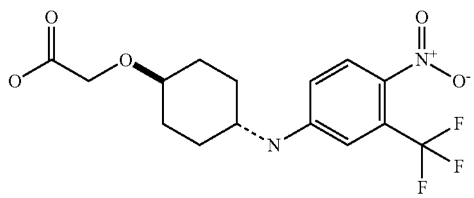 | I-B | 3.514 | 363.1 | 362.3 |
| A7 | 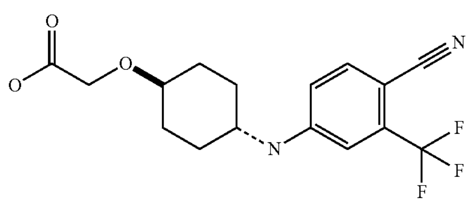 | I-B | 3.405 | 343.1 | 342.3 |
| A17 | 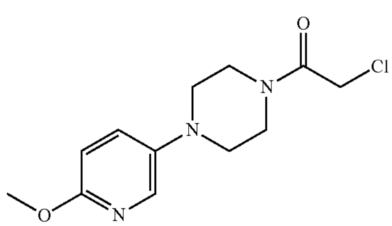 [SMILES: COc1ccc(N2CCN(C(=O)CCl)CC2)cn1] | I-B | 2.543 | 270.1 | 269.7 |
| A18 | 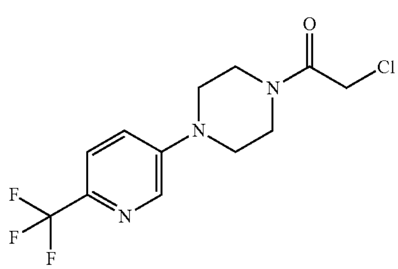 [SMILES: O=C(CCl)N1CCN(c2ccc(C(F)(F)F)nc2)CC1] | I-B | 3.178 | 308.0 | 307.7 |
| A19 | 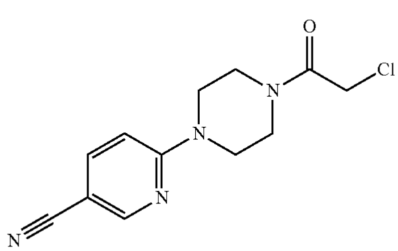 [SMILES: N#Cc1ccc(N2CCN(C(=O)CCl)CC2)nc1] | I-B | 2.817 | 265.1 | 264.7 |

TABLE II-continued

| Compound | Structure | HPLC Method | RT (min) | m/z | MW calculated (g/mol) |
| --- | --- | --- | --- | --- | --- |
| A20 | [1-(chloroacetyl)-4-(5-(trifluoromethyl)pyridin-2-yl)piperazine] | I-B | 3.497 | 308.0 | 307.7 |
| A21 | [1-(chloroacetyl)-4-(5-chloropyridin-2-yl)piperazine] | I-B | 3.202 | 274.0 | 274.2 |
| A22 | [1-(chloroacetyl)-4-(3-chloro-5-(trifluoromethyl)pyridin-2-yl)piperazine] | I-B | 3.919 | 342.0 | 342.2 |
| A23 | [1-(chloroacetyl)-4-(5-(trifluoromethyl)-1,3,4-thiadiazol-2-yl)piperazine] | I-B | 3.181 | 315.0 | 314.7 |
| A24 | [1-(chloroacetyl)-4-(6-cyanopyridin-3-yl)piperazine] | II-B | 2.529 | 264.8 | 264.7 |

TABLE III

| Compound | Structure | HPLC Method | RT (min) | (m/z) | MW calculated (g/mol) |
|---|---|---|---|---|---|
| B1 | 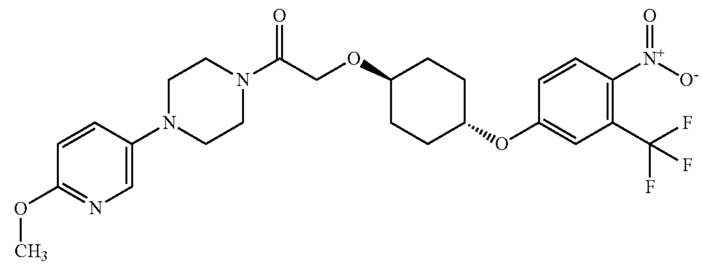 [SMILES: COc1ccc(N2CCN(C(=O)CO[C@H]3CC[C@H](Oc4ccc([N+](=O)[O-])c(C(F)(F)F)c4)CC3)CC2)cn1] | I-A | 5.659 | 539.0 | 538.5 |
| B2 | 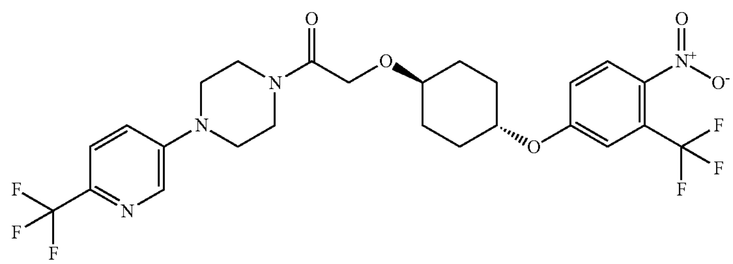 [SMILES: O=C(CO[C@H]1CC[C@H](Oc2ccc([N+](=O)[O-])c(C(F)(F)F)c2)CC1)N1CCN(c2ccc(C(F)(F)F)nc2)CC1] | I-A | 5.789 | 577.2 | 576.5 |
| B3 | 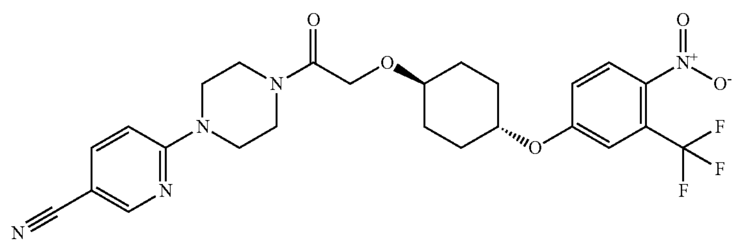 [SMILES: N#Cc1ccc(N2CCN(C(=O)CO[C@H]3CC[C@H](Oc4ccc([N+](=O)[O-])c(C(F)(F)F)c4)CC3)CC2)nc1] | I-A | 5.659 | 534.2 | 533.5 |
| B4 | 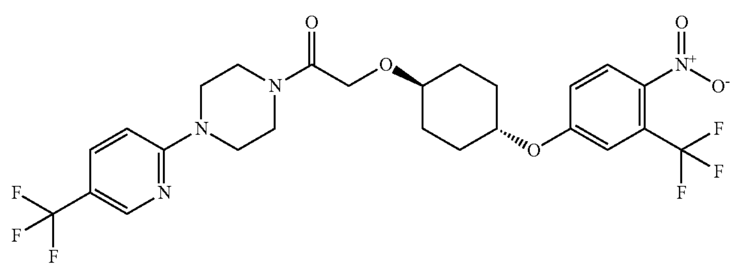 [SMILES: O=C(CO[C@H]1CC[C@H](Oc2ccc([N+](=O)[O-])c(C(F)(F)F)c2)CC1)N1CCN(c2ccc(C(F)(F)F)cn2)CC1] | I-A | 5.982 | 577.2 | 576.5 |
| B5 | 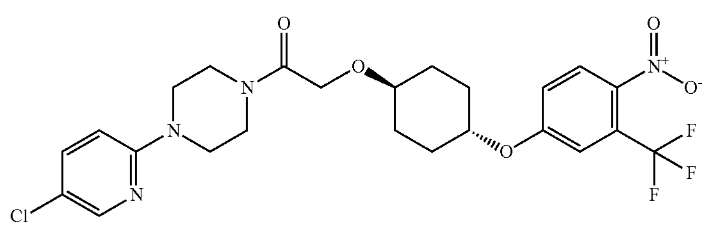 [SMILES: O=C(CO[C@H]1CC[C@H](Oc2ccc([N+](=O)[O-])c(C(F)(F)F)c2)CC1)N1CCN(c2ccc(Cl)cn2)CC1] | I-A | 5.951 | 343.1 | 542.9 |
| B6 | 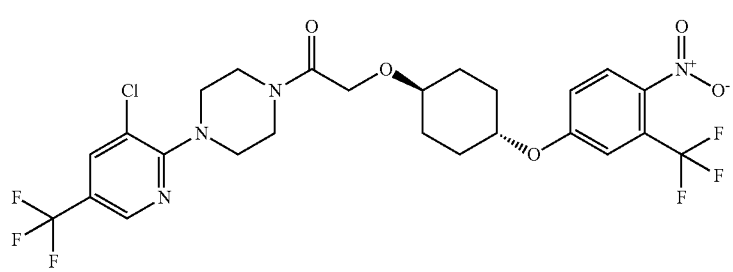 [SMILES: O=C(CO[C@H]1CC[C@H](Oc2ccc([N+](=O)[O-])c(C(F)(F)F)c2)CC1)N1CCN(c2ncc(C(F)(F)F)cc2Cl)CC1] | I-A | 6.206 | 611.1 | 610.9 |

TABLE III-continued

| Compound | Structure | HPLC Method | RT (min) | (m/z) | MW calculated (g/mol) |
|---|---|---|---|---|---|
| B7 | 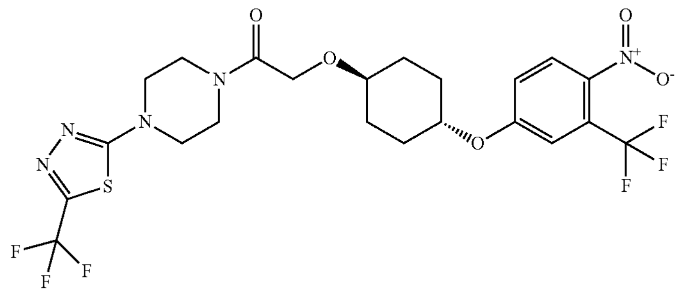 [SMILES: O=C(CO[C@H]1CC[C@H](Oc2ccc([N+](=O)[O-])c(C(F)(F)F)c2)CC1)N1CCN(c2nnc(C(F)(F)F)s2)CC1] | I-A | 5.755 | 584.1 | 583.5 |
| D1 | 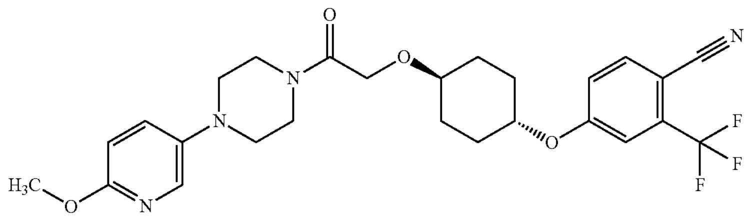 [SMILES: COc1ccc(N2CCN(C(=O)CO[C@H]3CC[C@H](Oc4ccc(C#N)c(C(F)(F)F)c4)CC3)CC2)cn1] | I-A | 5.564 | 519.2 | 518.5 |
| D2 | 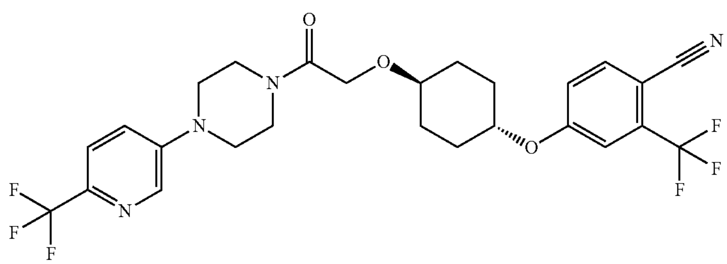 [SMILES: N#Cc1ccc(O[C@H]2CC[C@H](OCC(=O)N3CCN(c4ccc(C(F)(F)F)nc4)CC3)CC2)cc1C(F)(F)F] | I-A | 5.717 | 557.2 | 556.5 |
| D3 | 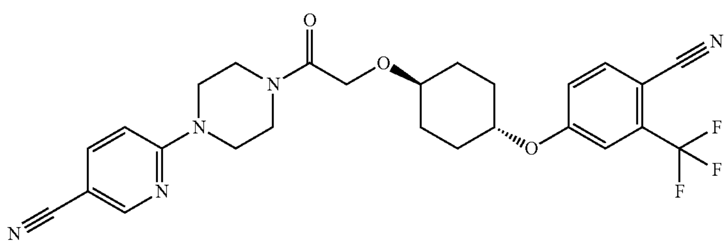 | I-A | 5.580 | 514.2 | 513.5 |
| D4 | 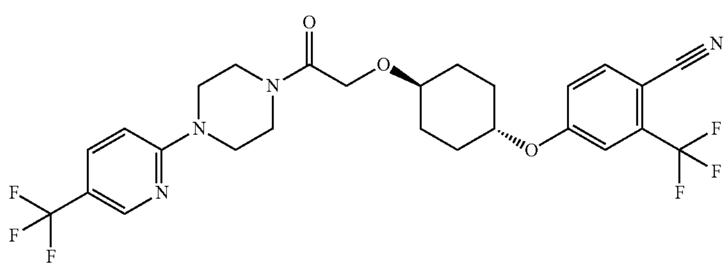 | I-A | 5.916 | 557.2 | 556.5 |
| D5 | 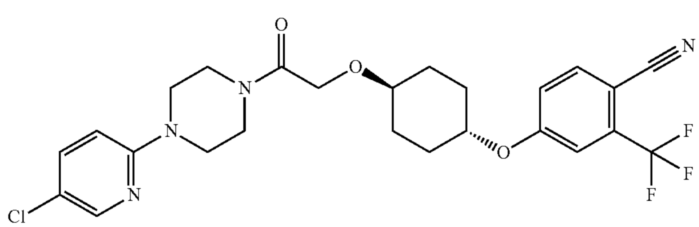 [SMILES: N#Cc1ccc(O[C@H]2CC[C@H](OCC(=O)N3CCN(c4ccc(Cl)cn4)CC3)CC2)cc1C(F)(F)F] | I-A | 5.877 | 523.2 | 523.0 |

TABLE III-continued

| Compound | Structure | HPLC Method | RT (min) | (m/z) | MW calculated (g/mol) |
|---|---|---|---|---|---|
| D6 | 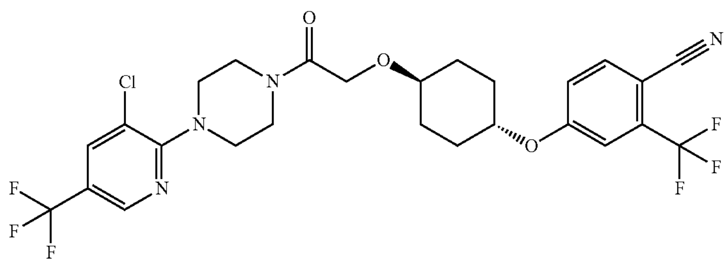 [SMILES: N#Cc1ccc(O[C@H]2CC[C@H](OCC(=O)N3CCN(c4ncc(C(F)(F)F)cc4Cl)CC3)CC2)cc1C(F)(F)F] | I-A | 6.150 | 591.1 | 590.9 |
| D7 | 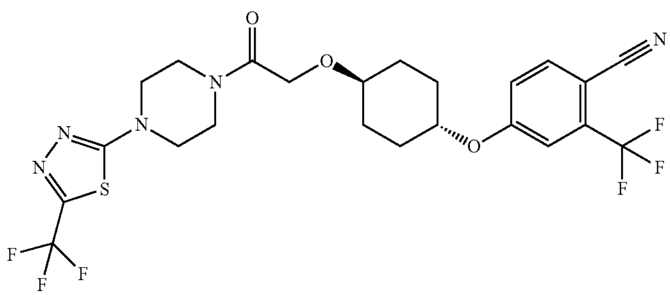 | I-A | 5.679 | 564.1 | 563.5 |
| C1 | 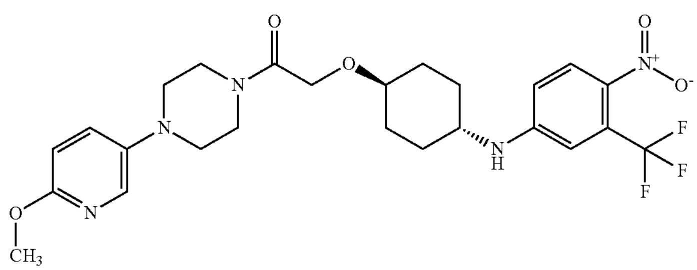 [SMILES: COc1ccc(N2CCN(C(=O)CO[C@H]3CC[C@H](Nc4ccc([N+](=O)[O-])c(C(F)(F)F)c4)CC3)CC2)cn1] | I-A | 5.443 | 538.2 | 537.5 |
| C2 | 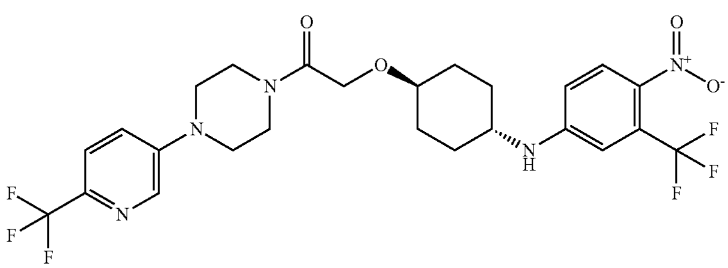 [SMILES: O=C(CO[C@H]1CC[C@H](Nc2ccc([N+](=O)[O-])c(C(F)(F)F)c2)CC1)N1CCN(c2ccc(C(F)(F)F)nc2)CC1] | I-A | 5.611 | 576.2 | 575.5 |
| C3 | 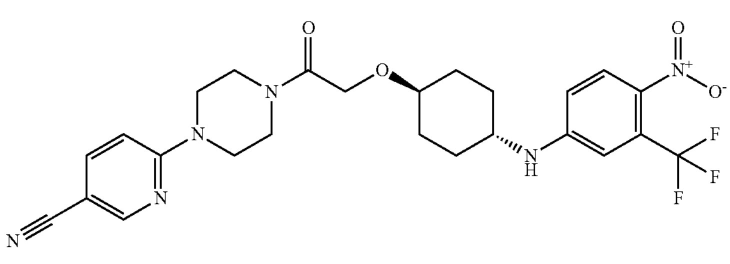 | I-A | 5.472 | 533.2 | 532.5 |

TABLE III-continued

| Compound | Structure | HPLC Method | RT (min) | (m/z) | MW calculated (g/mol) |
|---|---|---|---|---|---|
| C4 | 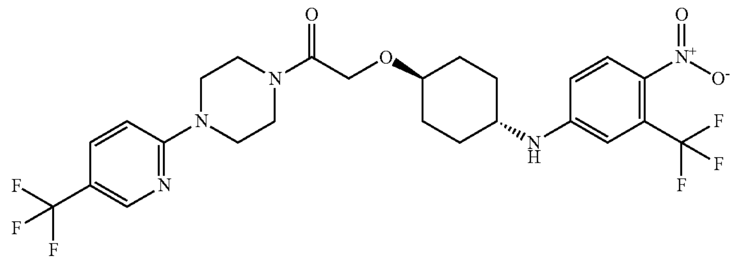 [SMILES: O=C(CO[C@H]1CC[C@H](Nc2ccc([N+](=O)[O-])c(C(F)(F)F)c2)CC1)N1CCN(c2ccc(C(F)(F)F)cn2)CC1] | I-A | 5.799 | 576.0 | 575.5 |
| C5 | 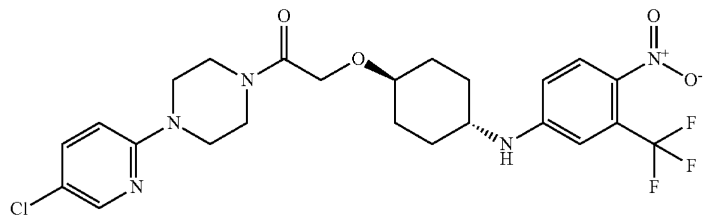 [SMILES: O=C(CO[C@H]1CC[C@H](Nc2ccc([N+](=O)[O-])c(C(F)(F)F)c2)CC1)N1CCN(c2ccc(Cl)cn2)CC1] | I-A | 5.750 | 542.1 | 542.0 |
| C6 | 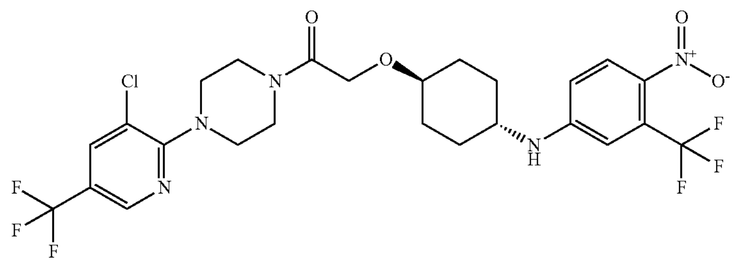 | I-A | 6.021 | 610.2 | 610.0 |
| C7 | 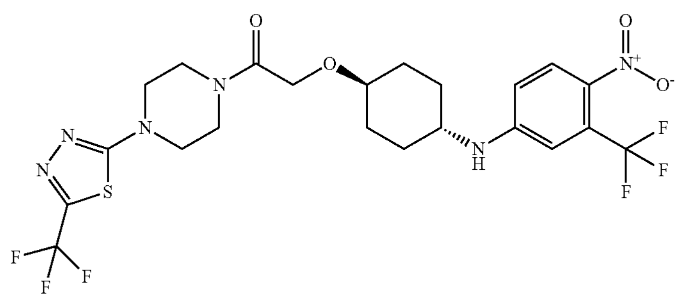 [SMILES: O=C(CO[C@H]1CC[C@H](Nc2ccc([N+](=O)[O-])c(C(F)(F)F)c2)CC1)N1CCN(c2nnc(C(F)(F)F)s2)CC1] | I-A | 5.578 | 583.2 | 582.5 |
| C8 | 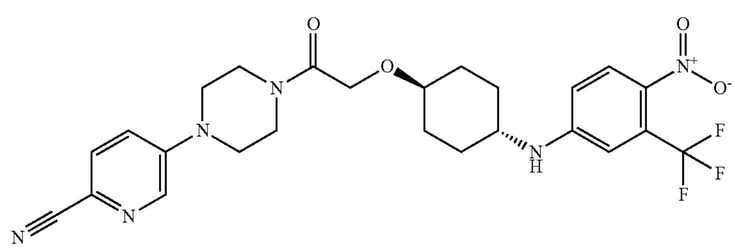 [SMILES: N#Cc1ccc(N2CCN(C(=O)CO[C@H]3CC[C@H](Nc4ccc([N+](=O)[O-])c(C(F)(F)F)c4)CC3)CC2)cn1] | I-A | 5.360 | 533.2 | 532.5 |
| E1 | 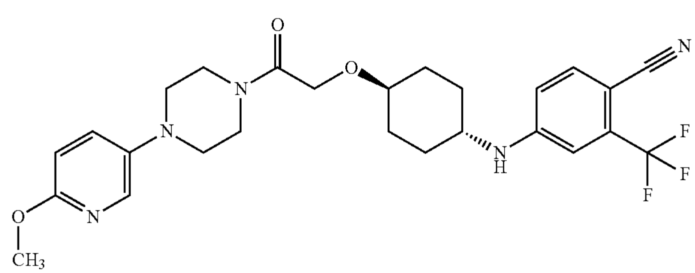 [SMILES: COc1ccc(N2CCN(C(=O)CO[C@H]3CC[C@H](Nc4ccc(C#N)c(C(F)(F)F)c4)CC3)CC2)cn1] | I-A | 5.359 | 518.2 | 517.5 |

TABLE III-continued

| Compound | Structure | HPLC Method | RT (min) | (m/z) | MW calculated (g/mol) |
|---|---|---|---|---|---|
| E2 | 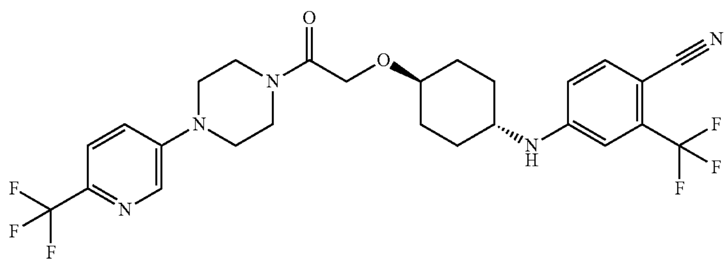 | I-A | 5.546 | 556.2 | 555.5 |
| E3 | 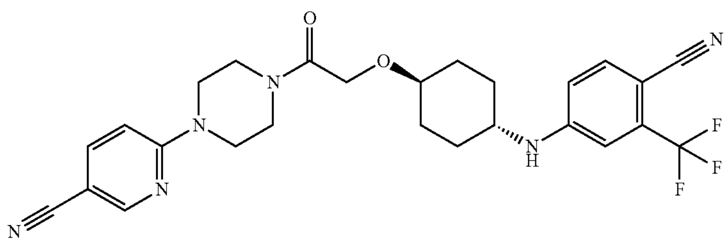 [SMILES: N#Cc1ccc(N2CCN(C(=O)CO[C@H]3CC[C@H](Nc4ccc(C#N)c(C(F)(F)F)c4)CC3)CC2)nc1] | I-A | 5.400 | 513.2 | 512.5 |
| E4 | 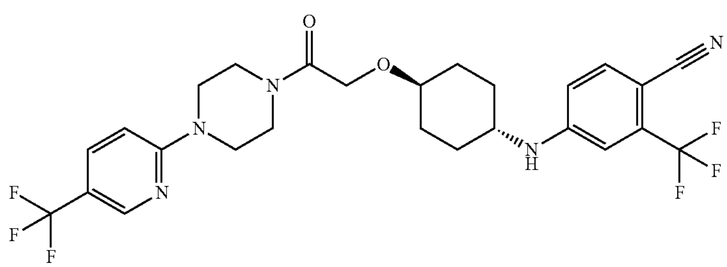 | I-A | 5.739 | 556.2 | 555.5 |
| E5 | 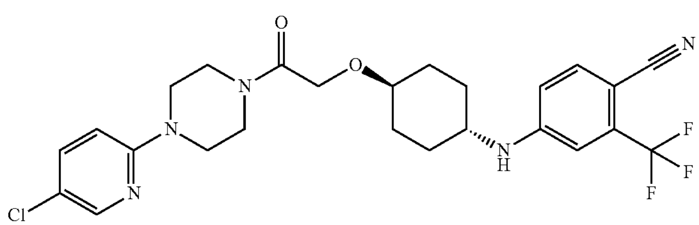 | I-A | 5.681 | 522.2 | 522.0 |
| E6 | 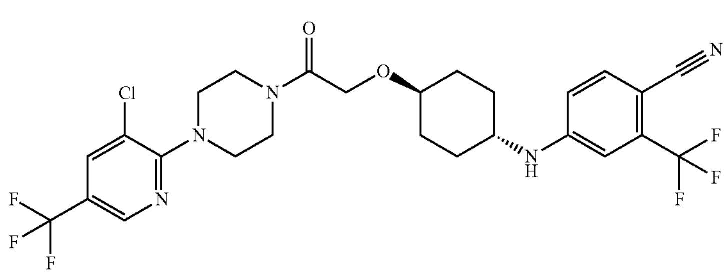 | I-A | 5.971 | 590.2 | 590.0 |

TABLE III-continued
| Compound | Structure | HPLC Method | RT (min) | (m/z) | MW calculated (g/mol) |
|---|---|---|---|---|---|
| E7 | 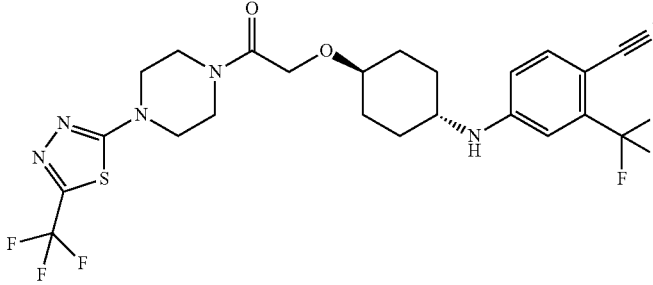 | I-A | 5.509 | 563.2 | 562.5 |
| E8 | 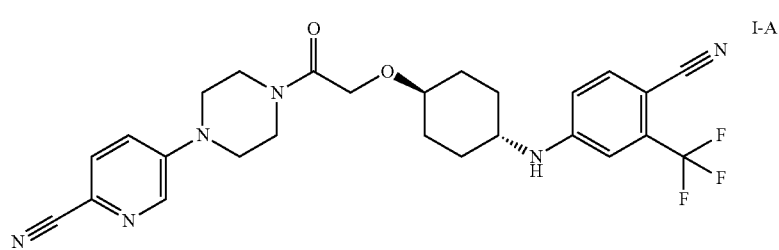 | I-A | 5.283 | 513.2 | 512.5 |
| F1 | 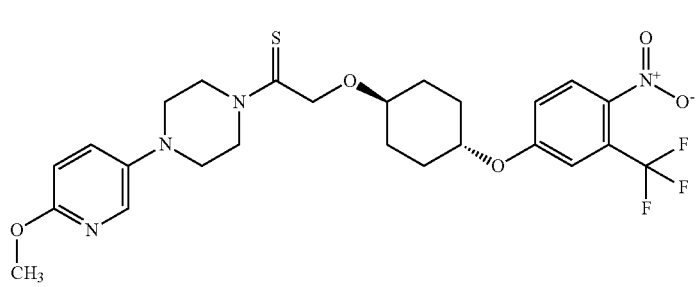 | I-A | 6.081 | 555.2 | 554.6 |
| F2 | 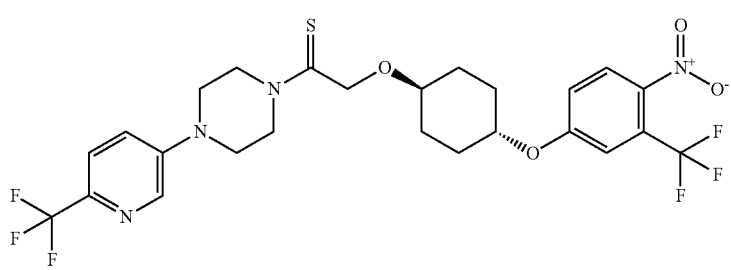 [SMILES: O=[N+]([O-])c1ccc(O[C@H]2CC[C@H](OCC(=S)N3CCN(c4ccc(C(F)(F)F)nc4)CC3)CC2)cc1C(F)(F)F] | I-A | 6.082 | 593.2 | 592.6 |
| F3 | 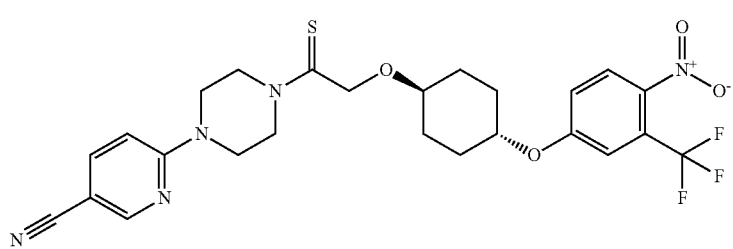 | I-A | 5.992 | 550.2 | 549.6 |

TABLE III-continued

| Compound | Structure | HPLC Method | RT (min) | (m/z) | MW calculated (g/mol) |
|---|---|---|---|---|---|
| F4 | 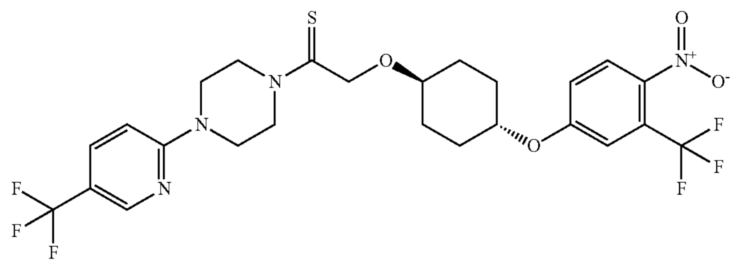 | I-A | 6.262 | 593.2 | 592.6 |
| F5 | 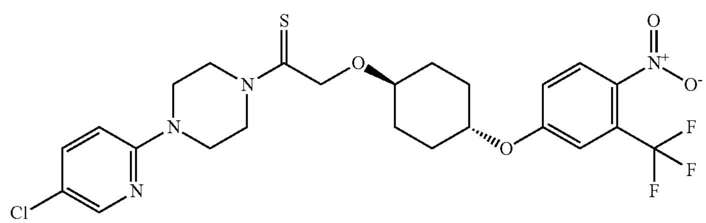 | I-A | 6.273 | 559.1 | 559.0 |
| F6 | 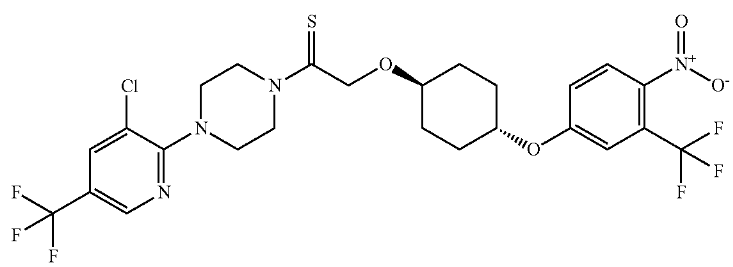 | I-A | 6.464 | 627.1 | 627.0 |
| F7 | 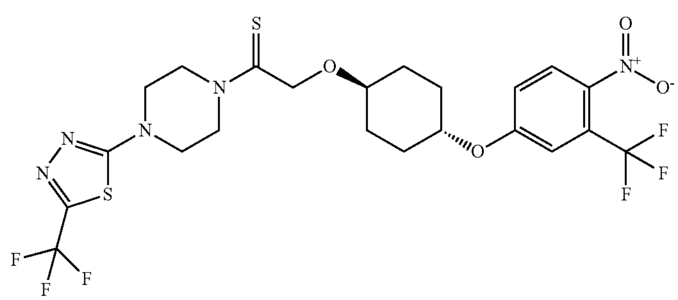 | I-A | 6.066 | 600.1 | 599.6 |
| F8 | 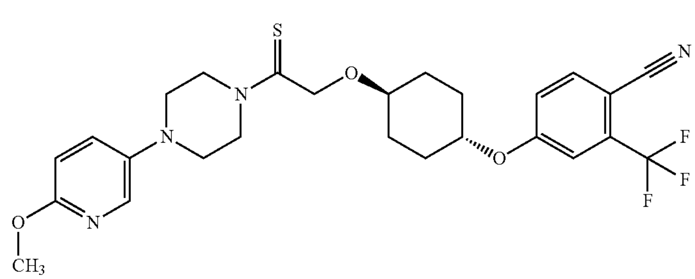 [SMILES: COc1ccc(N2CCN(C(=S)CO[C@H]3CC[C@H](Oc4ccc(C#N)c(C(F)(F)F)c4)CC3)CC2)cn1] | I-A | 5.987 | 535.2 | 534.6 |

TABLE III-continued

| Compound | Structure | HPLC Method | RT (min) | (m/z) | MW calculated (g/mol) |
|---|---|---|---|---|---|
| F9 | 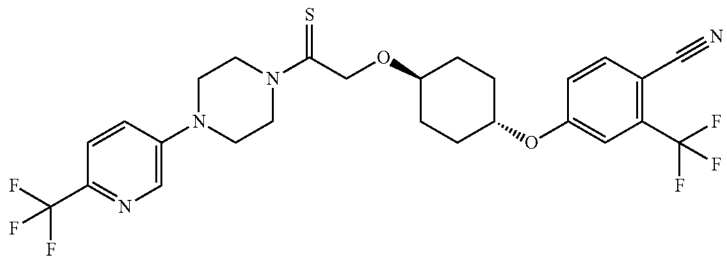 [SMILES: N#Cc1ccc(O[C@H]2CC[C@H](OCC(=S)N3CCN(c4ccc(C(F)(F)F)nc4)CC3)CC2)cc1C(F)(F)F] | I-A | 6.028 | 573.2 | 572.6 |
| F10 | 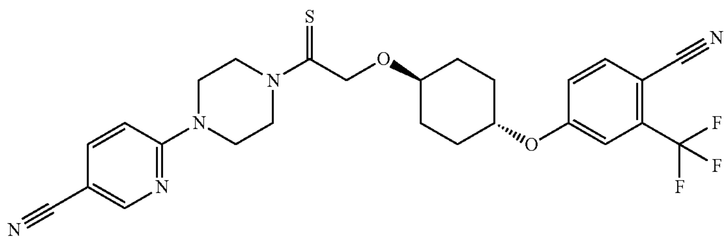 [SMILES: N#Cc1ccc(N2CCN(C(=S)CO[C@H]3CC[C@H](Oc4ccc(C#N)c(C(F)(F)F)c4)CC3)CC2)nc1] | I-A | 5.932 | 530.2 | 529.6 |
| F11 | 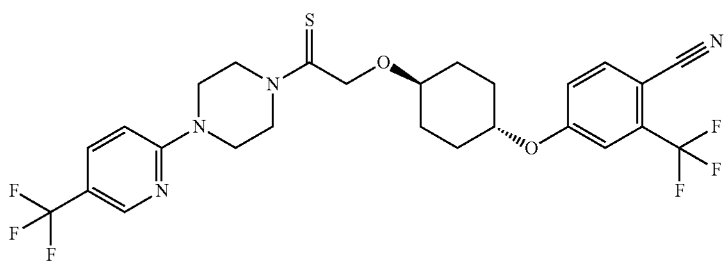 [SMILES: N#Cc1ccc(O[C@H]2CC[C@H](OCC(=S)N3CCN(c4ccc(C(F)(F)F)cn4)CC3)CC2)cc1C(F)(F)F] | I-A | 6.219 | 573.2 | 572.6 |
| F12 | 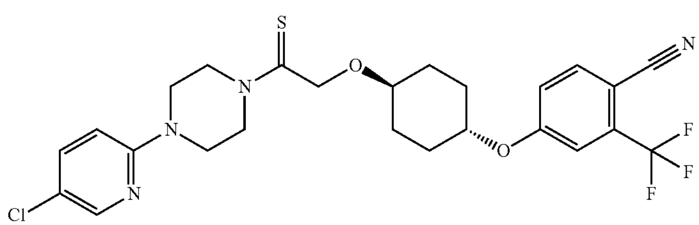 [SMILES: N#Cc1ccc(O[C@H]2CC[C@H](OCC(=S)N3CCN(c4ccc(Cl)cn4)CC3)CC2)cc1C(F)(F)F] | I-A | 6.224 | 539.1 | 539.0 |
| F13 | 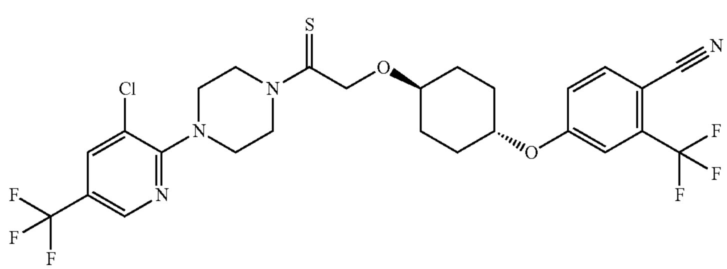 | I-A | 6.429 | 607.1 | 607.0 |
| F14 | 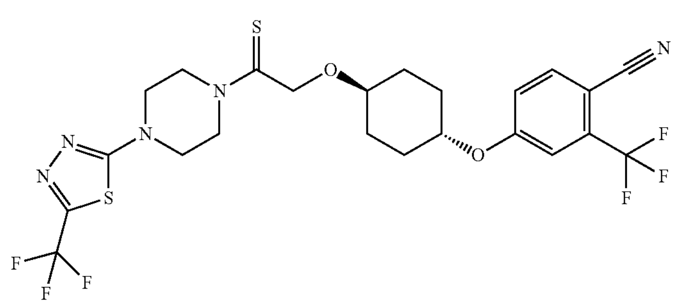 [SMILES: N#Cc1ccc(O[C@H]2CC[C@H](OCC(=S)N3CCN(c4nnc(C(F)(F)F)s4)CC3)CC2)cc1C(F)(F)F] | I-A | 6.010 | 580.1 | 579.6 |

TABLE III-continued

| Compound | Structure | HPLC Method | RT (min) | (m/z) | MW calculated (g/mol) |
|---|---|---|---|---|---|
| F15 | 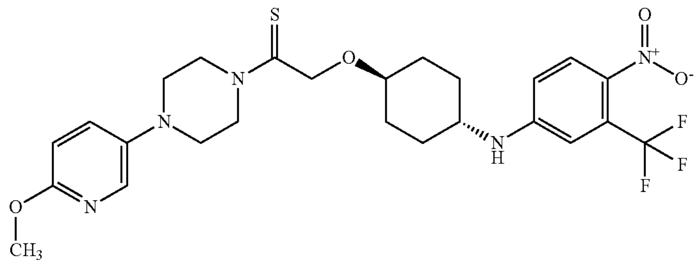 | I-A | 5.837 | 554.2 | 553.6 |
| F16 | 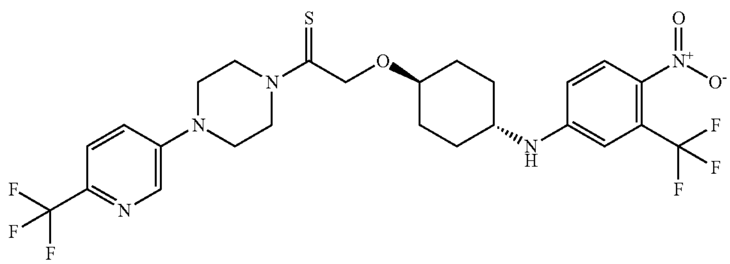 | I-A | 5.902 | 592.2 | 591.6 |
| F17 | 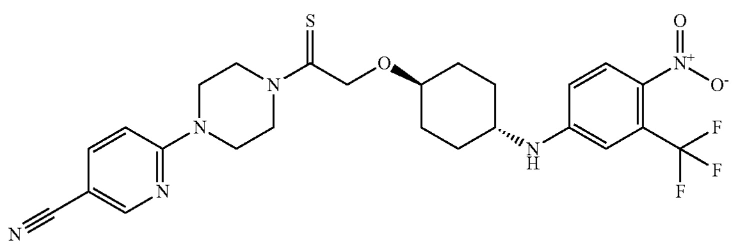 [SMILES: N#Cc1ccc(N2CCN(C(=S)CO[C@H]3CC[C@H](Nc4ccc([N+](=O)[O-])c(C(F)(F)F)c4)CC3)CC2)nc1] | I-A | 5.799 | 549.2 | 548.6 |
| F18 | 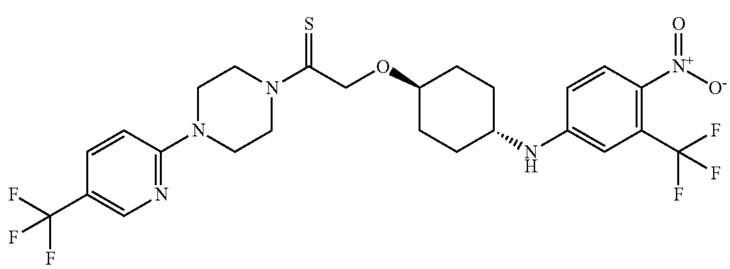 [SMILES: O=[N+]([O-])c1ccc(N[C@H]2CC[C@H](OCC(=S)N3CCN(c4ccc(C(F)(F)F)cn4)CC3)CC2)cc1C(F)(F)F] | I-A | 6.091 | 592.2 | 591.6 |
| F19 | 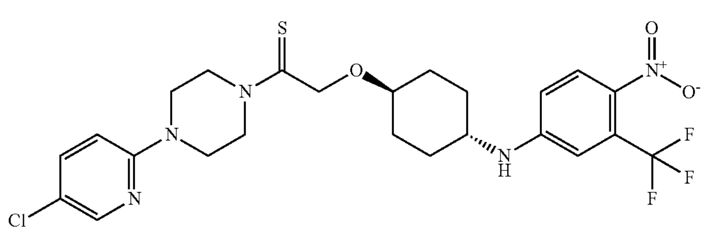 | I-A | 6.088 | 558.1 | 558.0 |
| F20 | 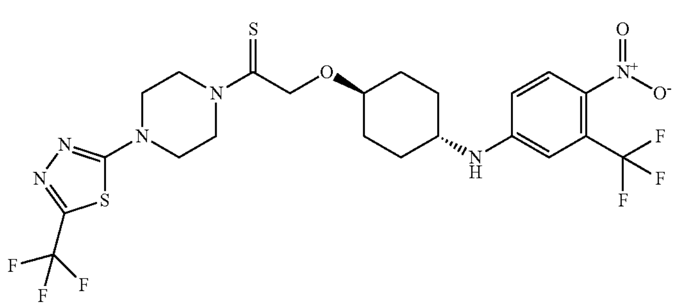 | I-A | 5.887 | 599.1 | 598.6 |

TABLE III-continued

| Compound | Structure | HPLC Method | RT (min) | (m/z) | MW calculated (g/mol) |
|---|---|---|---|---|---|
| F21 | 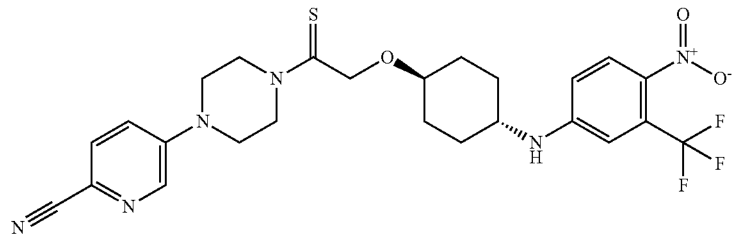 | I-A | 5.682 | 549.2 | 548.6 |
| F23 | 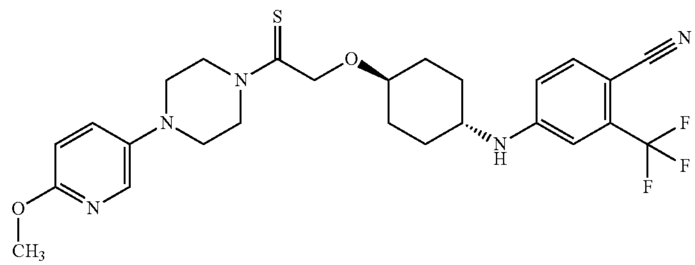 | I-A | 5.774 | 534.2 | 533.6 |
| F24 | 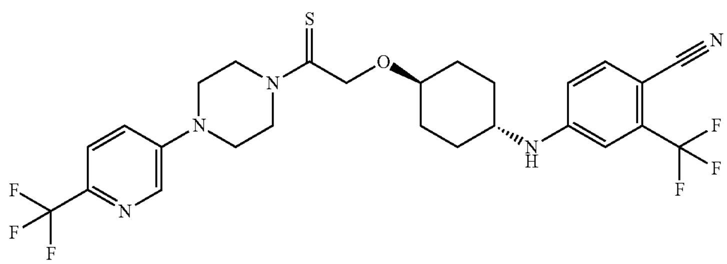 [SMILES: N#Cc1ccc(N[C@H]2CC[C@H](OCC(=S)N3CCN(c4ccc(C(F)(F)F)nc4)CC3)CC2)cc1C(F)(F)F] | I-A | 5.850 | 572.2 | 571.6 |
| F25 | 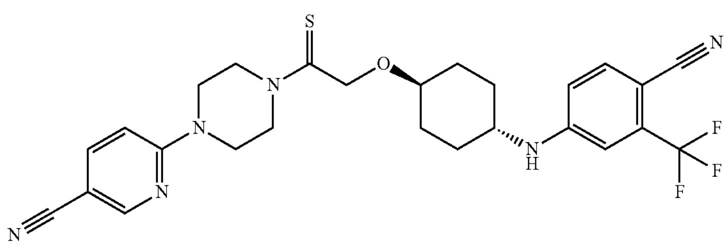 [SMILES: N#Cc1ccc(N2CCN(C(=S)CO[C@H]3CC[C@H](Nc4ccc(C#N)c(C(F)(F)F)c4)CC3)CC2)nc1] | I-A | 5.742 | 529.2 | 528.6 |
| F26 | 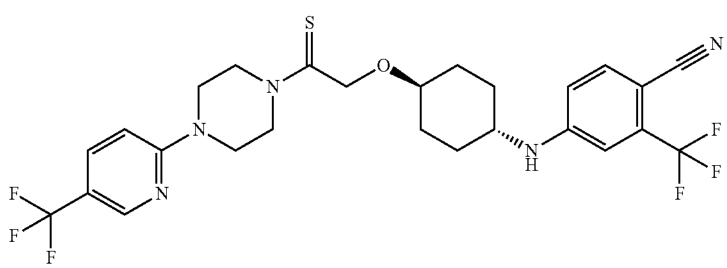 [SMILES: N#Cc1ccc(N[C@H]2CC[C@H](OCC(=S)N3CCN(c4ccc(C(F)(F)F)cn4)CC3)CC2)cc1C(F)(F)F] | I-A | 6.045 | 572.2 | 571.6 |
| F27 | 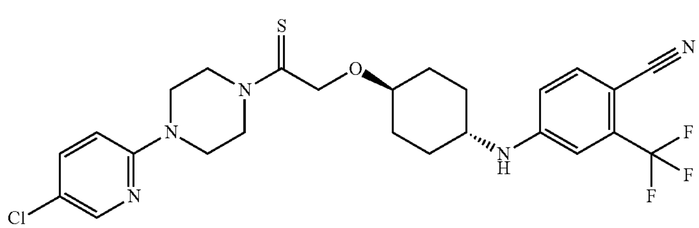 | I-A | 6.038 | 539.1 | 538.0 |

TABLE III-continued

| Compound | Structure | HPLC Method | RT (min) | (m/z) | MW calculated (g/mol) |
|---|---|---|---|---|---|
| F28 | 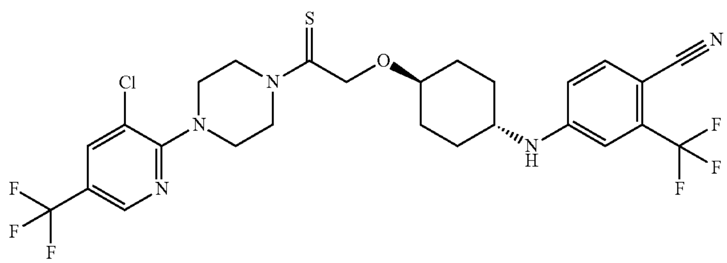 [SMILES: N#Cc1ccc(N[C@H]2CC[C@H](OCC(=S)N3CCN(c4ncc(C(F)(F)F)cc4Cl)CC3)CC2)cc1C(F)(F)F] | I-A | 6.269 | 606.1 | 606.0 |
| F29 | 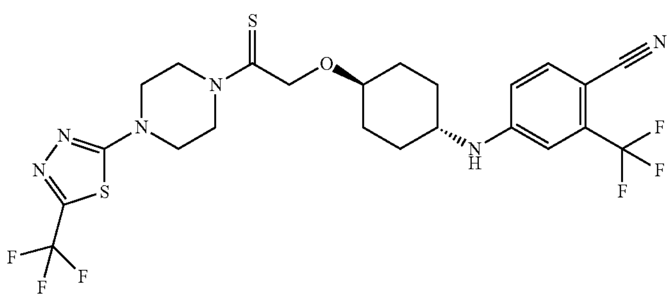 [SMILES: N#Cc1ccc(N[C@H]2CC[C@H](OCC(=S)N3CCN(c4nnc(C(F)(F)F)s4)CC3)CC2)cc1C(F)(F)F] | I-A | 5.834 | 579.1 | 578.6 |
| B8 | 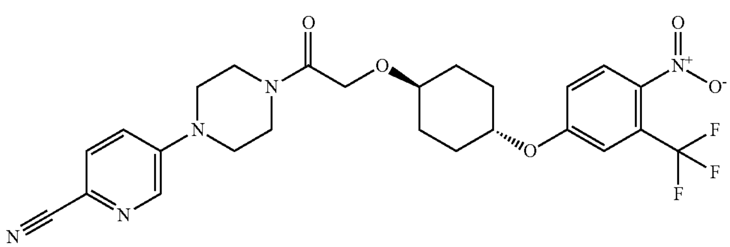 [SMILES: N#Cc1ccc(N2CCN(C(=O)CO[C@H]3CC[C@H](Oc4ccc([N+](=O)[O-])c(C(F)(F)F)c4)CC3)CC2)cn1] | I-A | 5.539 | 534.2 | 533.5 |
| F22 | 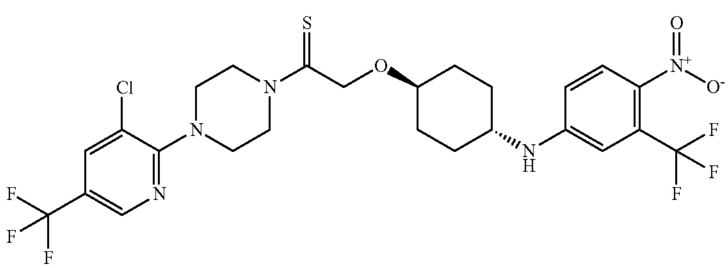 [SMILES: O=[N+]([O-])c1ccc(N[C@H]2CC[C@H](OCC(=S)N3CCN(c4ncc(C(F)(F)F)cc4Cl)CC3)CC2)cc1C(F)(F)F] | I-A | 6.314 | 626.1 | 626.0 |
| C11 | 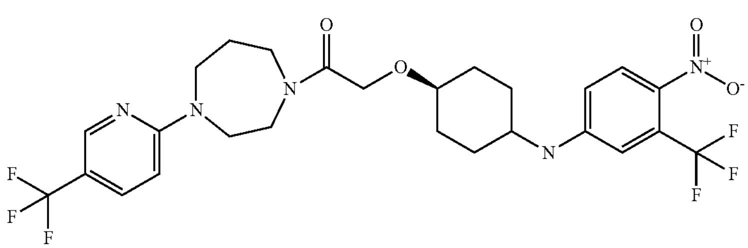 | I-A | 5.859 | 590.2 | 589.5 |

TABLE III-continued

| Compound | Structure | HPLC Method | RT (min) | (m/z) | MW calculated (g/mol) |
|---|---|---|---|---|---|
| C9 | 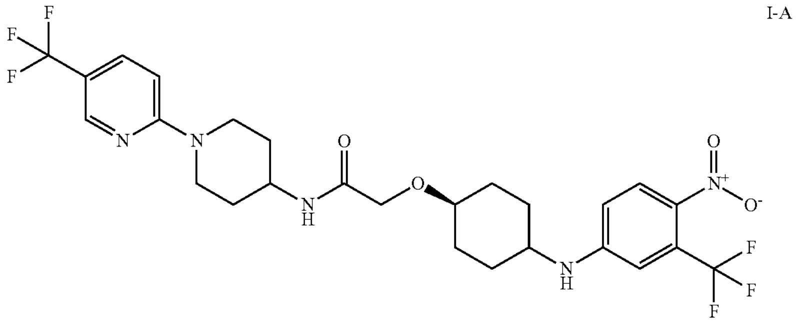 | I-A | 5.943 | 590.2 | 589.5 |
| C10 | 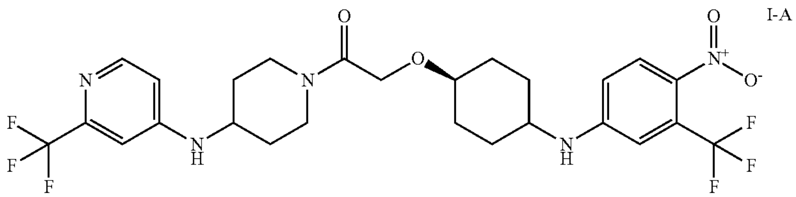 | I-A | 5.217 | 590.2 | 589.5 |
| E10 | 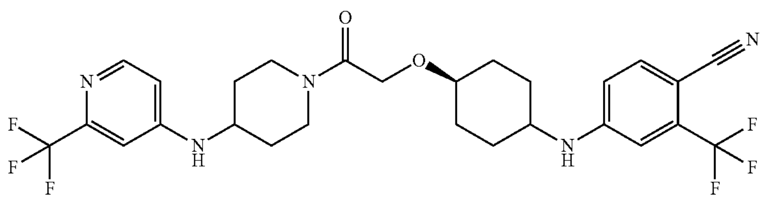 | I-A | 5.110 | 570.2 | 569.5 |
| E9 | 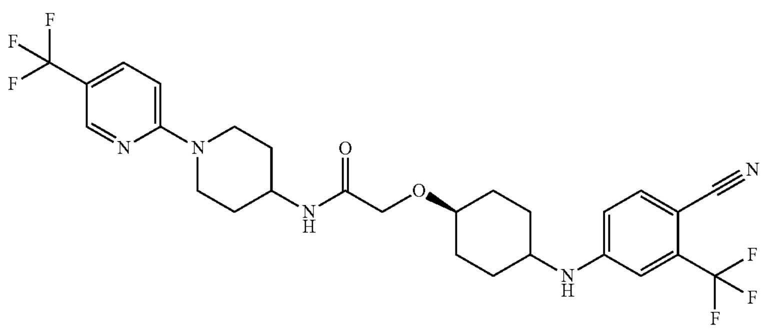 | I-A | 5.879 | 570.2 | 569.5 |
| E11 | 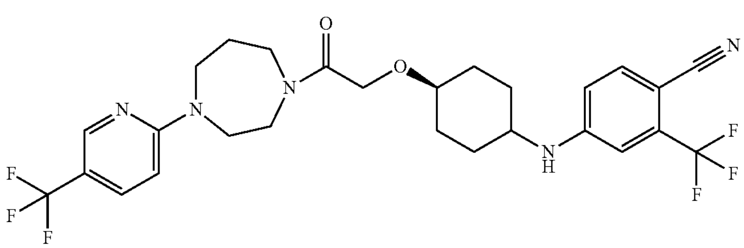 | I-A | 5.785 | 570.2 | 569.5 |
| C13 | 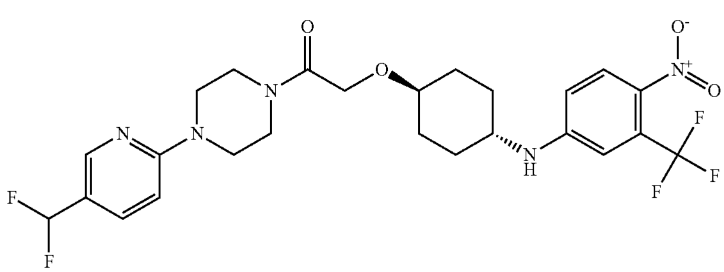 [SMILES: O=C(CO[C@H]1CC[C@H](Nc2ccc([N+](=O)[O-])c(C(F)(F)F)c2)CC1)N1CCN(c2ccc(C(F)F)cn2)CC1] | II-A | 4 | 557.7 | 557.5 |

TABLE III-continued

| Compound | Structure | HPLC Method | RT (min) | (m/z) | MW calculated (g/mol) |
|---|---|---|---|---|---|
| C14 | 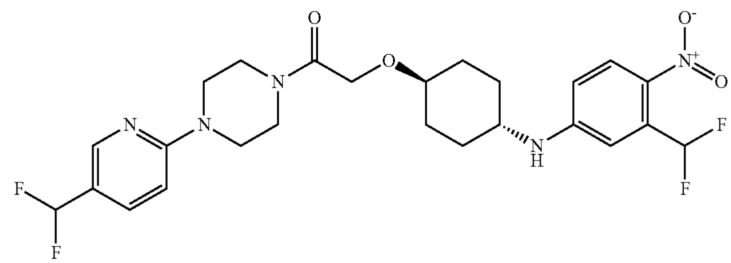 [SMILES: O=C(CO[C@H]1CC[C@H](Nc2ccc([N+](=O)[O-])c(C(F)F)c2)CC1)N1CCN(c2ccc(C(F)F)cn2)CC1] | II-A | 4.169 | 539.8 | 539.5 |
| C12 | 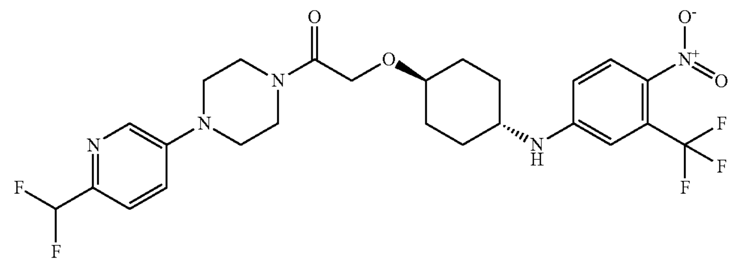 [SMILES: O=C(CO[C@H]1CC[C@H](Nc2ccc([N+](=O)[O-])c(C(F)(F)F)c2)CC1)N1CCN(c2ccc(C(F)F)nc2)CC1] | I-C | 1.894 | 558 | 557.5 |
| F30 | 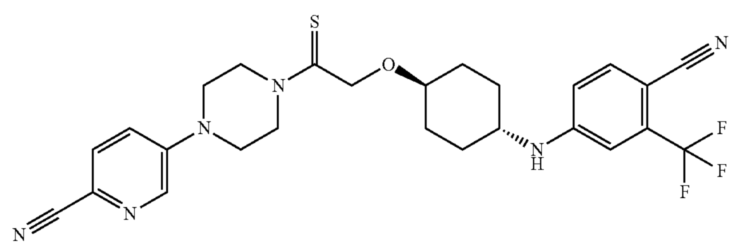 [SMILES: N#Cc1ccc(N2CCN(C(=S)CO[C@H]3CC[C@H](Nc4ccc(C#N)c(C(F)(F)F)c4)CC3)CC2)cn1] | I-A | 5.622 | 529 | 528.6 |

H) Biological Examples

Determining Activity Against *Ascaridia galli* and *Oesophagostomum dentatum*

Anthelmintic effects of compounds of this invention were tested in vitro using gut-welling larval stages of two parasitic nematode species: *Ascaridia galli* (intestinal roundworm of chicken), larval stage 3 ("L3"); and *Oesophagostumum dentatum* (nodular worm of swine), larval stages 3 and 4 (respectively "L3" and "L4"). When conducting these experiments, DMSO-solutions of various concentrations of compounds of this invention were prepared and incubated in 96-well microtiter plates. The parasites were then distributed at 20 larvae per well. The anthelmintic effects were classified by microscopic examination. The microscopic examination included assessing mortality, damage, motility, progression of development, and neutral red uptake by the larvae in comparison to a DMSO-control. The anthelmintic effects were defined by the minimum effective concentration ("MEC"), which is the concentration by which at least one of the larvae shows mortality, damage, change in motility, change in progression of development, or no neutral red uptake. Compounds B1-B7, C1-C14, D1-D8, E1-11 and F1-F30 showed at least some activity against one or more of the nematodes. Compounds B1-B7, $C_1$-$C_{14}$, D1-D8, E1-11 and F1-F30 exhibited an MEC of less than 7 μmol/l against *Ascaridia Galli*.

DEFINITIONS

The term "alkyl" (alone or in combination with another term(s)) means a straight- or branched-chain saturated hydrocarbyl substituent (i.e., a substituent containing only carbon and hydrogen) typically containing from 1 to about 20 carbon atoms, more typically from 1 to about 8 carbon atoms, and even more typically from 1 to about 6 carbon atoms. Examples of such substituents include methyl, ethyl, n-propyl, isopropyl, n-butyl, iso-butyl, sec-butyl, tert-butyl, pentyl, iso-amyl, hexyl, and octyl.

The term "alkenyl" (alone or in combination with another term(s)) means a straight- or branched-chain hydrocarbyl substituent containing one or more double bonds and typically from 2 to about 20 carbon atoms, more typically from about 2 to about 20 carbon atoms, even more typically from about 2 to about 8 carbon atoms, and still even more typically from about 2 to about 6 carbon atoms. Examples of such substituents include ethenyl (vinyl); 2-propenyl; 3-propenyl; 1,4-pentadienyl; 1,4-butadienyl; 1-butenyl; 2-butenyl; 3-butenyl; and decenyl.

The term "alkynyl" (alone or in combination with another term(s)) means a straight- or branched-chain hydrocarbyl substituent containing one or more triple bonds and typically from 2 to about 20 carbon atoms, more typically from about 2 to about 8 carbon atoms, and even more typically from about 2 to about 6 carbon atoms. Examples of such substituents include ethynyl, 2-propynyl, 3-propynyl, decynyl, 1-butynyl, 2-butynyl, and 3-butynyl.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent typically containing from 3 to 14 carbon ring atoms ("ring atoms" are the atoms bound together to form the ring or rings of a cyclic moiety). A carbocyclyl may be a single ring, which typically contains from 3 to 6 ring atoms. Examples of such single-ring carbocyclyls include cyclopropanyl, cyclobutanyl, cyclopentyl, cyclopentenyl, cyclopentadienyl, cyclohexyl, cyclohexenyl, cyclohexadienyl, and phenyl. A carbocyclyl alternatively may be multiple (typically 2 or 3) rings fused together, such as naphthalenyl, tetrahydronaphthalenyl (also known as "tetralinyl"), indenyl, isoindenyl, indanyl, bicyclodecanyl, anthracenyl, phenanthrene, benzonaphthenyl (also known as "phenalenyl"), fluoreneyl, decalinyl, and norpinanyl.

The term "cycloalkyl" (alone or in combination with another term(s)) means a saturated cyclic hydrocarbyl substituent typically containing from 3 to 14 carbon ring atoms. A cycloalkyl may be a single carbon ring, which typically contains from 3 to 6 carbon ring atoms. Examples of single-ring cycloalkyls include cyclopropyl (or "cyclopropanyl"), cyclobutyl (or "cyclobutanyl"), cyclopentyl (or "cyclopentanyl"), and cyclohexyl (or "cyclohexanyl"). A cycloalkyl alternatively may be multiple (typically 2 or 3) carbon rings fused together, such as, decalinyl or norpinanyl.

The term "aryl" (alone or in combination with another term(s)) means an aromatic carbocyclyl typically containing from 6 to 14 carbon ring atoms. Examples of aryls include phenyl, naphthalenyl, and indenyl.

In some instances, the number of carbon atoms in a hydrocarbyl group (e.g., alkyl, alkenyl, alkynyl, or cycloalkyl) is indicated by the prefix "$C_x$-$C_y$-", wherein x is the minimum and y is the maximum number of carbon atoms in the group. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

The term "hydrogen" (alone or in combination with another term(s)) means a hydrogen radical (or "hydrido"), and may be depicted as —H.

The term "hydroxy" (alone or in combination with another term(s)) means —OH.

The term "nitro" (alone or in combination with another term(s)) means —NO$_2$.

The term "cyano" (alone or in combination with another term(s)) means —CN, which also may be depicted:

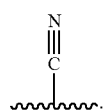

The term "oxo" (alone or in combination with another term(s)) means an oxo radical, and may be depicted as:

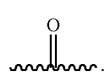

The term "carboxy" (alone or in combination with another term(s)) means —C(O)—OH, which also may be depicted as:

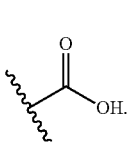 [SMILES: *C(=O)O]

The term "amino" (alone or in combination with another term(s)) means —NH$_2$.

The term "halogen" (alone or in combination with another term(s)) means a fluorine radical ("fluoro", which may be depicted as —F), chlorine radical ("chloro", which may be depicted as —Cl), bromine radical ("bromo", which may be depicted as —Br), or iodine radical ("iodo", which may be depicted as —I). Typically, fluoro or chloro is preferred, with fluoro often being particularly preferred.

If a substituent is described as being "substituted", a non-hydrogen substituent is in the place of a hydrogen on a carbon, nitrogen, oxygen, or sulfur of the substituent. Thus, for example, a substituted alkyl substituent is an alkyl substituent wherein at least one non-hydrogen substituent is in the place of a hydrogen on the alkyl substituent. To illustrate, monofluoroalkyl is alkyl substituted with a fluoro, and difluoroalkyl is alkyl substituted with two fluoros. It should be recognized that if there are more than one substitutions on a substituent, each non-hydrogen substituent may be identical or different (unless otherwise stated).

If a substituent is described as being "optionally substituted", the substituent may be either (1) not substituted or (2) substituted. If a substituent is described as being optionally substituted with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 substituents, then any heteroaryl with less than 3 substitutable positions would be optionally substituted by up to only as many non-hydrogen substituents as the heteroaryl has substitutable positions. To illustrate, tetrazolyl (which has only one substitutable position when it is bonded to a single non-hydrogen moiety by a single bond) would be optionally substituted with up to one non-hydrogen substituent. To illustrate further, if an amino nitrogen is described as being optionally substituted with up to 2 non-hydrogen substituents, then a primary amino nitrogen will be optionally substituted with up to 2 non-hydrogen substituents, whereas a secondary amino nitrogen will be optionally substituted with up to only one non-hydrogen substituent.

The prefix "halo" indicates that the substituent to which the prefix is attached is substituted with one or more independently selected halogens. For example, haloalkyl means an alkyl substituent having a halogen in the place of a hydrogen, or multiple halogens in the place of the same number of hydrogens. Examples of haloalkyls include chloromethyl, 1-bromoethyl, fluoromethyl, difluoromethyl, trifluoromethyl, and 1,1,1-trifluoroethyl. Illustrating further, "haloalkoxy" means an alkoxy substituent wherein a halogen is in the place of a hydrogen, or multiple halogens are in the place of the same number of hydrogens. Examples of haloalkoxy substituents include chloromethoxy, 1-bromoethoxy, fluoromethoxy, difluoromethoxy, trifluoromethoxy (also known as "perfluoromethyloxy"), and 1,1,1,-trifluoroethoxy. It should be recognized that if a substituent is substituted by more than one halogen, the halogens may be identical or different (unless otherwise stated).

The term "carbonyl" (alone or in combination with another term(s)) means —C(O)—, which also may be depicted as:

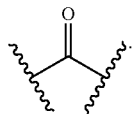 [SMILES: *C(*)=O]

This term also is intended to encompass a hydrated carbonyl substituent, i.e., —C(OH)$_2$—.

The term "aminocarbonyl" (alone or in combination with another term(s)) means —C(O)—NH$_2$, which also may be depicted as:

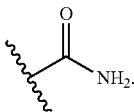

The term "oxy" (alone or in combination with another term(s)) means an ether substituent, and may be depicted as —O—.

The term "alkoxy" (alone or in combination with another term(s)) means an alkylether substituent, i.e., —O-alkyl. Examples of such a substituent include methoxy (—O—CH$_3$), ethoxy, n-propoxy, iso-propoxy, n-butoxy, iso-butoxy, sec-butoxy, and tert-butoxy.

The term "alkylcarbonyl" (alone or in combination with another term(s)) means —C(O)-alkyl. For example, "ethylcarbonyl" may be depicted as:

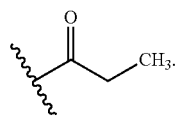 [SMILES: *C(=O)CC]

The term "alkoxycarbonyl" (alone or in combination with another term(s)) means —C(O)—O-alkyl. For example, "ethoxycarbonyl" may be depicted as:

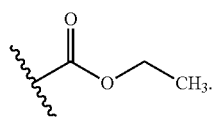 [SMILES: *C(=O)OCC]

The term "carbocyclylcarbonyl" (alone or in combination with another term(s)) means —C(O)-carbocyclyl. For example, "phenylcarbonyl" may be depicted as:

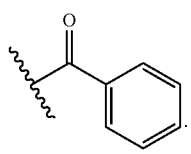 [SMILES: *C(=O)c1ccccc1]

Similarly, the term "heterocyclylcarbonyl" (alone or in combination with another term(s)) means —C(O)-heterocyclyl.

The term "sulfanyl" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-sulfanyl-alkyl" means alkyl-S-alkyl.

The term "thiol" or "mercapto" (alone or in combination with another term(s)) means a sulfhydryl substituent, and may be depicted as —SH.

The term "thiocarbonyl" (alone or in combination with another term(s)) means a carbonyl wherein a sulfur is in the place of the oxygen. Such a substituent may be depicted as —C(S)—, and also may be depicted as:

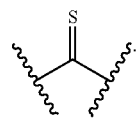

The term "sulfonyl" (alone or in combination with another term(s)) means —S(O)$_2$—, which also may be depicted as:

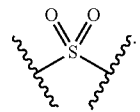

Thus, for example, "alkyl-sulfonyl-alkyl" means alkyl-S(O)$_2$-alkyl.

The term "aminosulfonyl" (alone or in combination with another term(s)) means —S(O)$_2$—NH$_2$, which also may be depicted as:

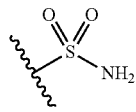

The term "sulfinyl" (alone or in combination with another term(s)) means —S(O)—, which also may be depicted as:

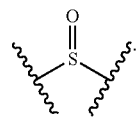

Thus, for example, "alkyl-sulfinyl-alkyl" means alkyl-S(O)-alkyl.

The term "heterocyclyl" (alone or in combination with another term(s)) means a saturated (i.e., "heterocycloalkyl"), non-aromatic partially-saturated (i.e., "heterocycloalkenyl"), or heterocyclic aromatic (i.e., "heteroaryl") ring structure typically containing a total of 3 to 14 ring atoms. At least one of the ring atoms is a heteroatom (typically oxygen, nitrogen, or sulfur), with the remaining ring atoms generally being independently selected from the group typically consisting of carbon, oxygen, nitrogen, and sulfur.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, thienyl (also known as "thiophenyl" and "thiofuranyl"), oxazolyl, isoxazolyl, thiazolyl, isothiazolyl, thiodiazolyl, oxadiazolyl (including 1,2,3-oxadiazolyl, 1,2,4-oxadiazolyl (also known as "azoximyl"), 1,2,5-oxadiazolyl (also known as "furazanyl"), and 1,3,4-oxadiazolyl), pyrrolyl, pyrazolyl, imidazolyl, triazolyl, tetrazolyl, oxathiazolyl, oxatriazolyl (including 1,2,3,4-oxatriazolyl and 1,2,3,5-oxatriazolyl), pyridinyl, diazinyl (including pyridazinyl (also known as "1,2-diazinyl"), pyrimidinyl (also known as "1,3-diazinyl"), and pyrazinyl (also known as "1,4-diazinyl")), triazinyl (including s-triazinyl (also known as "1,3,5-triazinyl"), as-triazinyl (also known 1,2,4-triazinyl), and v-triazinyl (also known as "1,2,3-triazinyl")), oxathiazinyl (including 1,2,5-oxathiazinyl and 1,2,6-oxathiazinyl), oxepinyl, thiepinyl, dihydrofuranyl, tetrahydrofuranyl, dihydrothienyl (also known as "dihydrothiophenyl"), tetrahydrothienyl (also known as "tetrahydrothiophenyl"), isopyrrolyl, pyrrolinyl, pyrrolidinyl, isoimidazolyl, imidazolinyl, imidazolidinyl, pyrazolinyl, pyrazolidinyl, dithiolyl, oxathiolyl, oxathiolanyl, oxazolidinyl, isoxazolidinyl, thiazolinyl, isothiazolinyl, thiazolidinyl, isothiazolidinyl, dioxazolyl (including 1,2,3-dioxazolyl, 1,2,4-dioxazolyl, 1,3,2-dioxazolyl, and 1,3,4-dioxazolyl), pyranyl (including 1,2-pyranyl and 1,4-pyranyl), dihydropyranyl, tetrahydropyranyl, piperidinyl, piperazinyl, oxazinyl (including 1,2,3-oxazinyl, 1,3,2-oxazinyl, 1,3,6-oxazinyl (also known as "pentoxazolyl"), 1,2,6-oxazinyl, and 1,4-oxazinyl), isoxazinyl (including o-isoxazinyl and p-isoxazinyl), oxadiazinyl (including 1,4,2-oxadiazinyl and 1,3,5,2-oxadiazinyl), morpholinyl, azepinyl, and diazepinyl.

A heterocyclyl alternatively may be 2 or 3 rings fused together, such as, for example, indolizinyl, pyranopyrrolyl, purinyl, imidazopyrazinyl, imidazolopyridazyl, pyridopyridinyl (including pyrido[3,4-b]-pyridinyl, pyrido[3,2-b]-pyridinyl, pyrido[4,3-b]-pyridinyl, and naphthyridinyl), pteridinyl, pyridazinotetrazinyl, pyrazinotetrazinyl, pyrimidinotetrazinyl, pyrindinyl, pyrazolopyrimidinyl, pyrazolopyrazinyl, pyrazolopyridazyl, or 4H-quinolizinyl. In some embodiments, the preferred multi-ring heterocyclyls are indolizinyl, pyranopyrrolyl, purinyl, pyridopyridinyl, pyrindinyl, and 4H-quinolizinyl.

Other examples of fused-ring heterocyclyls include benzo-fused heterocyclyls, such as, for example, benzofuranyl (also known as "coumaronyl"), isobenzofuranyl, benzoxazolyl, benzoisoxazolyl (also known as "indoxazinyl"), anthranilyl, benzothienyl (also known as "benzothiophenyl", "thionaphthenyl", and "benzothiofuranyl"), isobenzothienyl (also known as "isobenzothiophenyl", "isothionaphthenyl", and "isobenzothiofuranyl"), benzothiazolyl, benzoisothiazolyl, benzothiadiazolyl, benzoxadiazolyl, indolyl, isoindazolyl (also known as "benzpyrazolyl"), benzoimidazolyl, benzotriazolyl, benzazinyl (including quinolinyl (also known as "1-benzazinyl") and isoquinolinyl (also known as "2-benzazinyl")), phthalazinyl, quinoxalinyl, benzodiazinyl (including cinnolinyl (also known as "1,2-benzodiazinyl") and quinazolinyl (also known as "1,3-benzodiazinyl")), benzoimidazothiazolyl, carbazolyl, acridinyl, isoindolyl, indoleninyl (also known as "pseudoindolyl"), benzodioxolyl, chromanyl, isochromanyl, thiochromanyl, isothiochromanyl, chromenyl, isochromenyl, thiochromenyl, isothiochromenyl, benzodioxanyl, tetrahydroisoquinolinyl, benzoxazinyl (including 1,3,2-benzoxazinyl, 1,4,2-benzoxazinyl, 2,3,1-benzoxazinyl, and 3,1,4-benzoxazinyl), benzoisoxazinyl (including 1,2-benzisoxazinyl and 1,4-benzisoxazinyl), benzodiazinyl, and xanthenyl. In some embodiments, the preferred benzo-fused heterocyclyls are benzofuranyl, isobenzofuranyl, benzoxazolyl, benzoisoxazolyl, anthranilyl, benzothienyl, isobenzothienyl, benzothiazolyl, benzothiadiazolyl, benzoxadiazolyl, indolyl, isoindazolyl, benzoimidazolyl, benzotriazolyl, benzazinyl, phthalazinyl, quinoxalinyl, benzodiazinyl, carbazolyl, acridinyl, isoindolyl, indoleninyl, benzodioxolyl, chromanyl, isochromanyl, thiochromanyl, benzodioxanyl, tetrahydroisoquinolinyl, benzoxazinyl, benzoisoxazinyl, and xanthenyl.

The term "2-fused-ring" heterocyclyl (alone or in combination with another term(s)) means a saturated, non-aromatic partially-saturated, or heteroaryl containing two fused rings. Such heterocyclyls include, for example, benzofuranyl, isobenzofuranyl, benzoxazolyl, benzoisoxazolyl, anthranilyl, benzothienyl, isobenzothienyl, benzothiazolyl, benzoisothiazolyl, benzothiadiazolyl, indolizinyl, pyranopyrrolyl, benzoxadiazolyl, indolyl, isoindazolyl, benzoimidazolyl, benzotriazolyl, purinyl, imidazopyrazinyl, imidazolopyridazyl, quinolinyl, isoquinolinyl, pyridopyridinyl, phthalazinyl, quinoxalinyl, benzodiazinyl, pteridinyl, pyridazinotetrazinyl, pyrazinotetrazinyl, pyrimidinotetrazinyl, pyrindinyl, isoindolyl, indoleninyl, pyrazolopyrimidinyl, pyrazolopyrazinyl, pyrazolopyridazyl, benzodioxolyl, chromanyl, isochromanyl, thiochromanyl, isothiochromanyl, chromenyl, isochromenyl, thiochromenyl, isothiochromenyl, benzodioxanyl, tetrahydroisoquinolinyl, 4H-quinolizinyl, benzoxazinyl, and benzoisoxazinyl. In some embodiments, preferred 2-fused-ring heterocyclyls include benzofuranyl, isobenzofuranyl, benzoxazolyl, benzoisoxazolyl, anthranilyl, benzothienyl, isobenzothienyl, benzothiazolyl, benzothiadiazolyl, indolizinyl, pyranopyrrolyl, benzoxadiazolyl, indolyl, isoindazolyl, benzoimidazolyl, benzotriazolyl, purinyl, quinolinyl, isoquinolinyl, pyridopyridinyl, phthalazinyl, quinoxalinyl, benzodiazinyl, pteridinyl, pyrindinyl, isoindolyl, indoleninyl, benzodioxolyl, benzodioxanyl, tetrahydroisoquinolinyl, 4H-quinolizinyl, benzoxazinyl, and benzoisoxazinyl.

The term "heteroaryl" (alone or in combination with another term(s)) means an aromatic heterocyclyl typically containing from 5 to 14 ring atoms. A heteroaryl may be a single ring or multiple (typically 2 or 3) fused rings. Such moieties include, for example, 5-membered rings such as furanyl, thienyl, oxazolyl, isoxazolyl, thiazolyl, isothiazolyl, thiodiazolyl, oxadiazolyl, pyrrolyl, pyrazolyl, imidazolyl, triazolyl, tetrazolyl, oxathiazolyl, and oxatriazolyl; 6-membered rings such as pyridinyl, pyrazinyl, pyrimidinyl, pyridazinyl, triazinyl, and oxathiazinyl; 7-membered rings such as oxepinyl and thiepinyl; 6/5-membered fused-ring systems such as benzofuranyl, isobenzofuranyl, benzoxazolyl, benzoisoxazolyl, anthranilyl, benzothienyl, isobenzothienyl, benzothiazolyl, benzoisothiazolyl, benzothiadiazolyl, indolizinyl, pyranopyrrolyl, benzoxadiazolyl, indolyl, isoindazolyl, benzoimidazolyl, benzotriazolyl, purinyl, imidazopyrazinyl, and imidazolopyridazyl; and 6/6-membered fused-ring systems such as quinolinyl, isoquinolinyl, pyridopyridinyl, phthalazinyl, quinoxalinyl, benzodiazinyl, pteridinyl, pyridazinotetrazinyl, pyrazinotetrazinyl, pyrimidinotetrazinyl, benzoimidazothiazolyl, carbazolyl, and acridinyl. In some embodiments, the preferred 5-membered rings include furanyl, thienyl, oxazolyl, isoxazolyl, thiazolyl, isothiazolyl, oxadiazolyl, pyrazolyl, and imidazolyl; the preferred 6-membered rings include pyridinyl, pyrazinyl, pyrimidinyl, pyridazinyl, and triazinyl; the preferred 6/5-membered fused-ring systems include benzoxazolyl, benzoisoxazolyl, anthranilyl, benzothienyl, isobenzothienyl, and purinyl; and the preferred 6/6-membered fused-ring systems include quinolinyl, isoquinolinyl, and benzodiazinyl.

A carbocyclyl or heterocyclyl can optionally be substituted with, for example, one or more substituents independently selected from the group consisting of halogen, hydroxy, carboxy, oxo, alkyl, alkoxy, alkoxyalkyl, alkylcarbonyl, aryl, arylalkyl, arylalkoxy, arylalkoxyalkyl, arylalkoxycarbonyl, cycloalkyl, cycloalkylalkyl, cycloalkylalkoxy, cycloalkylalkoxyalkyl, and cycloalkylalkoxycarbonyl. More typically, a carbocyclyl or heterocyclyl may optionally be substituted with, for example, one or more substituents independently selected from the group consisting of halogen, —OH, —C(O)—OH, oxo, $C_1$-$C_6$-alkyl, $C_1$-$C_6$-alkoxy, $C_1$-$C_6$-alkoxy-$C_1$-$C_6$-alkyl, $C_1$-$C_6$-alkylcarbonyl, aryl, aryl-$C_1$-$C_6$-alkyl, aryl-$C_1$-$C_6$-alkoxy, aryl-$C_1$-$C_6$-alkoxy-$C_1$-$C_6$-alkyl, aryl-$C_1$-$C_6$-alkoxycarbonyl, cycloalkyl, cycloalkyl-$C_1$-$C_6$-alkyl, cycloalkyl-$C_1$-$C_6$-alkoxy, cycloalkyl-$C_1$-$C_6$-alkoxy-$C_1$-$C_6$-alkyl, and cycloalkyl-$C_1$-$C_6$-alkoxycarbonyl. The alkyl, alkoxy, alkoxyalkyl, alkylcarbonyl, aryl, arylalkyl, arylalkoxy, arylalkoxyalkyl, or arylalkoxycarbonyl substituent(s) may further be substituted with, for example, one or more halogen. The aryl and cycloalkyl portions of such optional substituents are typically single-rings containing from 3 to 6 ring atoms, and more typically from 5 to 6 ring atoms.

An aryl or heteroaryl can optionally be substituted with, for example, one or more substituents independently selected from the group consisting of halogen, —OH, —CN, —NO$_2$, —SH, —C(O)—OH, amino, aminoalkyl, alkyl, alkylsulfanyl, carboxyalkylsulfanyl, alkylcarbonyloxy, alkoxy, alkoxyalkyl, alkoxycarbonylalkoxy, alkoxyalkylsulfanyl, alkoxycarbonylalkylsulfanyl, carboxyalkoxy, alkoxycarbonylalkoxy, carbocyclyl, carbocyclylalkyl, carbocyclyloxy, carbocyclylsulfanyl, carbocyclylalkylsulfanyl, carbocyclylamino, carbocyclylalkylamino, carbocyclylcarbonylamino, carbocyclylalkyl, carbocyclylcarbonyloxy, carbocyclyloxyalkoxycarbocyclyl, carbocyclylsulfanylalkylsulfanylcarbocyclyl, carbocyclylsulfanylalkoxycarbocyclyl, carbocyclyloxyalkylsulfanylcarbocyclyl, heterocyclyl, heterocyclylalkyl, heterocyclyloxy, heterocyclylsulfanyl, heterocyclylalkylsulfanyl, heterocyclylamino, heterocyclylalkylamino, heterocyclylcarbonylamino, heterocyclylcarbonyloxy, heterocyclyloxyalkoxyheterocyclyl, heterocyclylsulfanylalkylsulfanylheterocyclyl, heterocyclylsulfanylalkoxyheterocyclyl, and heterocyclyloxyalkylsulfanylheterocyclyl. More typically, an aryl or heteroaryl may, for example, optionally be substituted with one or more substituents independently selected from the group consisting of halogen, —OH, —CN, —NO$_2$, —SH, —C(O)—OH, amino, amino-$C_1$-$C_6$-alkyl, $C_1$-$C_6$-alkyl, $C_1$-$C_6$-alkylsulfanyl, carboxy-$C_1$-$C_6$-alkylsulfanyl, $C_1$-$C_6$-alkylcarbonyloxy, $C_1$-$C_6$-alkoxy, $C_1$-$C_6$-alkoxy-$C_1$-$C_6$-alkyl, $C_1$-$C_6$-alkoxycarbonyl-$C_1$-$C_6$-alkoxy, $C_1$-$C_6$-alkoxy-$C_1$-$C_6$-alkylsulfanyl, $C_1$-$C_6$-alkoxycarbonyl-$C_1$-$C_6$-alkylsulfanyl, carboxy-$C_1$-$C_6$-alkoxy, $C_1$-$C_6$-alkoxycarbonyl-$C_1$-$C_6$-alkoxy, aryl, aryl-$C_1$-$C_6$-alkyl, aryloxy, arylsulfanyl, aryl-$C_1$-$C_6$-alkylsulfanyl, arylamino, aryl-$C_1$-$C_6$-alkylamino, arylcarbonylamino, arylcarbonyloxy, aryloxy-$C_1$-$C_6$-alkoxyaryl, arylsulfanyl-$C_1$-$C_6$-alkylsulfanylaryl, arylsulfanyl-$C_1$-$C_6$-alkoxyaryl, aryloxy-$C_1$-$C_6$-alkylsulfanylaryl, cycloalkyl, cycloalkyl-$C_1$-$C_6$-alkyl, cycloalkyloxy, cycloalkylsulfanyl, cycloalkyl-$C_1$-$C_6$-alkylsulfanyl, cycloalkylamino, cycloalkyl-$C_1$-$C_6$-alkylamino, cycloalkylcarbonylamino, cycloalkylcarbonyloxy, heteroaryl, heteroaryl-$C_1$-$C_6$-alkyl, heteroaryloxy, heteroarylsulfanyl, heteroaryl-$C_1$-$C_6$-alkylsulfanyl, heteroarylamino, heteroaryl-$C_1$-$C_6$-alkylamino, heteroarylcarbonylamino, and heteroarylcarbonyloxy. Here, one or more hydrogens bound to a carbon in any such substituent may, for example, optionally be replaced with halogen. In addition, any cycloalkyl, aryl, and heteroaryl portions of such optional substituents are typically single-rings containing 3 to 6 ring atoms, and more typically 5 or 6 ring atoms.

A prefix attached to a multi-component substituent only applies to the first component. To illustrate, the term "alkylcycloalkyl" contains two components: alkyl and cycloalkyl. Thus, the $C_1$-$C_6$- prefix on $C_1$-$C_6$-alkylcycloalkyl means that the alkyl component of the alkylcycloalkyl contains from 1 to 6 carbon atoms; the $C_1$-$C_6$- prefix does not describe the cycloalkyl component.

If substituents are described as being "independently selected," each substituent is selected independent of the other. Each substituent, therefore, may be identical to or different from the other selected substituent(s).

When words are used to describe a substituent, the rightmost-described component of the substituent is the component that has the free valence. To illustrate, benzene substituted with methoxyethyl has the following structure:

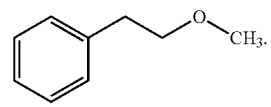

As can be seen, the ethyl is bound to the benzene, and the methoxy is the component of the substituent that is the component furthest from the benzene. As further illustration, benzene substituted with cyclohexanylsulfanylbutoxy has the following structure:

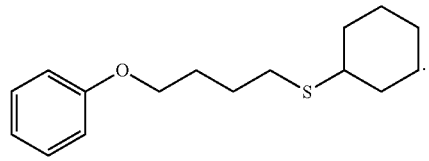 [SMILES: c1ccc(OCCCCSC2CCCCC2)cc1]

When a chemical formula is used to describe a monovalent substituent, the dash on the left side of the formula indicates the portion of the substituent that has the free valence. To illustrate, benzene substituted with —C(O)—OH has the following structure:

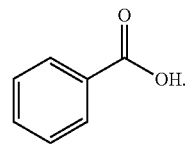

When a chemical formula is used to describe a di-valent (or "linking") component between two other components of a depicted chemical structure (the right and left components), the leftmost dash of the linking component indicates the portion of the linking component that is bound to the left component in the depicted structure. The rightmost dash, on the other hand, indicates the portion of the linking component that is bound to the right component in the depicted structure. To illustrate, if the depicted chemical structure is X-L-Y and L is described as —C(O)—N(H)—, then the chemical would be:

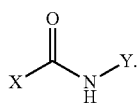

Dashes are not used to characterize a tri-valent component when standing alone. Thus, for example, a tri-valent nitrogen is identified as "N" and a tri-valent carbon bonded to hydrogen is identified as "CH" in this patent.

The term "pharmaceutically acceptable" is used adjectivally to mean that the modified noun is appropriate for use in a pharmaceutical product. When it is used, for example, to describe a salt or excipient, it characterizes the salt or excipient as being compatible with the other ingredients of the composition, and not deleterious to the intended recipient animal to the extent that the deleterious effect(s) outweighs the benefit(s) of the salt.

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

The invention claimed is:

1. A compound or salt thereof, wherein:

the compound corresponds in structure to Formula (I):

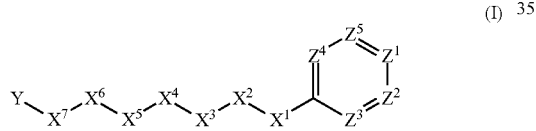

(I)

$X^1$ is selected from the group consisting of —O—, —S—, and —NH—, the —NH— is optionally substituted with a substituent selected from the group consisting of alkyl and alkoxyalkyl, any such substituent is optionally substituted with one or more independently selected halogen;

$X^2$ is selected from the group consisting of straight-chain $C_3$-$C_5$-alkyl, and $C_4$-$C_6$-carbocyclyl the straight-chain $C_3$-$C_5$-alkyl, and $C_4$-$C_6$-carbocyclyl are optionally substituted with one or more independently selected alkyl;

$X^3$ is selected from the group consisting of —CH_2—, —O—, —C(O)—, and —NH—, the —CH_2— is optionally substituted with up to two substituents independently selected from the group consisting of alkyl and carbocyclyl, the —NH— is optionally substituted with a substituent selected from the group consisting of alkyl and alkoxyalkyl, any such substituent of —NH— is optionally substituted with one or more independently selected halogen;

$X^4$ is selected from the group consisting of —CH_2, the —CH_2— is optionally substituted with up to two substituents independently selected from the group consisting of alkyl, haloalkyl and alkenyl;

$X^5$ is selected from the group consisting of —C(S)— and —C(O)—;

$X^6$ is a linker selected from the group consisting of

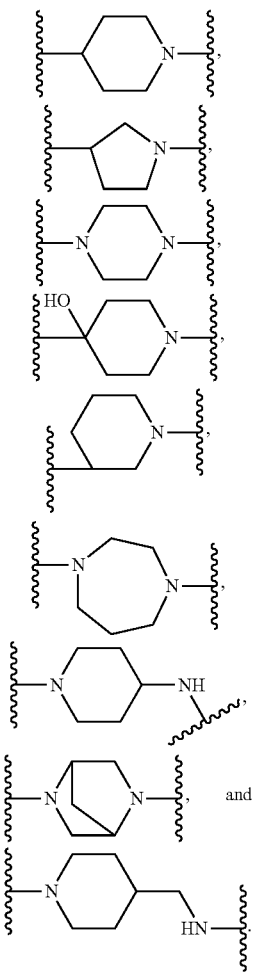

any such group is optionally substituted with one or more substituents independently selected from the group consisting of halogen, $C_1$-$C_6$-alkyl, hydroxy, $C_1$-$C_6$-alkoxy, oxo, and thiocarbonyl;

$X^7$ is selected from the group consisting of a bond, —O—, —NH—, —S—, —CH_2—, the —NH— is optionally substituted with alkyl, the —CH_2— is optionally substituted with one or more independently selected alkyl;

Y is a 5-membered or 6-membered heteroaryl group, selected from the group consisting of furanyl, thienyl, oxazolyl, isoxazolyl, thiazolyl, isothiazolyl, thiodiazolyl, oxadiazolyl, pyrrolyl, pyrazolyl, imidazolyl, tetrazolyl, pyridinyl, pyrazinyl, pyrimidinyl, and pyridazinyl, any such heteroaryl group is optionally substituted with one or more substituents independently selected from the group consisting of halogen, cyano, hydroxy, alkyl, alkoxy, nitro, aminosulfonyl, alkoxycarbonyl, alkylsulfanyl, aryl, aryloxy, arylalkoxy, arylsulfanyl, heteroaryl, heteroaryloxy, and heteroarylsulfanyl, the alkyl, alkoxy, aminosulfonyl, alkoxycarbonyl, alkylsulfanyl, aryl, aryloxy, arylalkoxy, arylsulfanyl, heteroaryl, heteroaryloxy, and heteroarylsulfanyl are optionally substituted with one or more substituents independently selected from the group consisting of halogen, cyano, alkyl, alkoxy, haloalkyl, and haloalkoxy;

109

$Z^1$ is selected from the group consisting of N and CH, the CH is optionally substituted with a substituent selected from the group consisting of halogen, nitro, cyano, aminosulfonyl, alkyl, alkoxy, alkoxycarbonyl, alkylsulfanyl, alkylsulfinyl, alkylsulfonyl, arylsulfanyl, arylsulfinyl, arylsulfonyl, heteroaryl, heteroarylsulfanyl, heteroarylsulfinyl, and heteroarylsulfonyl, the alkyl, alkoxy, alkoxycarbonyl, alkylsulfanyl, alkylsulfinyl, alkylsulfonyl, alkylsulfanyl, aryl, arylsulfanyl, arylsulfinyl, arylsulfonyl, heteroaryl, heteroarylsulfanyl, heteroarylsulfinyl, and heteroarylsulfonyl are optionally substituted with one or more substituents independently selected from the group consisting of halogen and alkyl; and the aminosulfonyl is optionally substituted with up to two independently selected alkyl;

$Z^2$ is selected from the group consisting of N and CH, the CH is optionally substituted with a substituent selected from the group consisting of cyano, halogen, nitro, alkyl, alkoxy, haloalkyl, and haloalkylsulfanyl;

Each of $Z^3$, $Z^4$, and $Z^5$ is independently selected from the group consisting of N and CH, the CH is optionally substituted with a substituent selected from the group consisting of halogen, cyano, nitro, alkyl, alkoxy, alkylsulfanyl, haloalkyl, haloalkoxy, and haloalkylsulfanyl.

2. A compound or salt thereof, wherein:
the compound corresponds in structure to Formula (I):

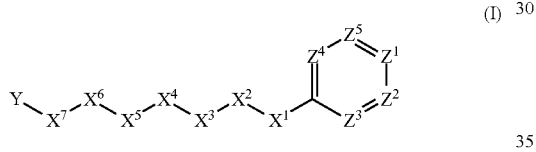

wherein, $X^1$ is selected from the group consisting of —O—, —S—, and —NH—;

$X^2$ is selected from the group consisting of $C_4$-$C_6$-carbocyclyl, the $C_4$-$C_6$-carbocyclyl is optionally substituted with one or more independently selected alkyl;

$X^3$ is selected from the group consisting of —CH$_2$—, and —O—, the —CH$_2$— is optionally substituted with up to two substituents independently selected from the group consisting of alkyl and carbocyclyl;

$X^4$ is selected from the group consisting of —CH$_2$—, the —CH$_2$— is optionally substituted with up to two methyl-substituents;

$X^5$ is selected from the group consisting of —C(S)— and —C(O)—;

$X^6$ is a linker selected from the group consisting of

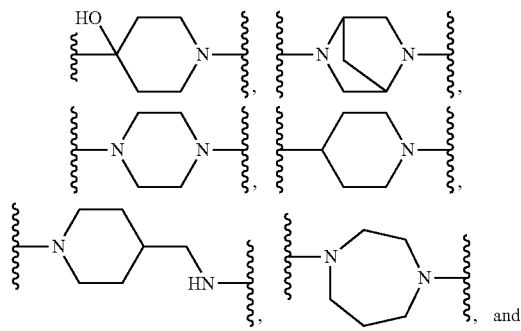

110

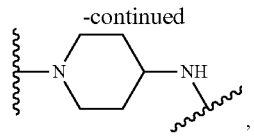

any such group is optionally substituted with one or more substituents independently selected from the group consisting of halogen, $C_1$-$C_6$-alkyl, hydroxy, $C_1$-$C_6$-alkoxy, oxo, and thiocarbonyl;

$X^7$ is selected from the group consisting of a bond, —O—, —NH—, —S—, —CH$_2$—, the —NH— is optionally substituted with alkyl, the —CH$_2$— is optionally substituted with one or more independently selected alkyl;

Y is a nitrogen-containing 5-membered or 6-membered heteroaryl group containing one, two, three or four nitrogen ring atoms, any such heteroaryl group is optionally substituted with one or more substituents independently selected from the group consisting of halogen, cyano, hydroxy, alkyl, alkoxy, nitro, aminosulfonyl, alkylsulfanyl, the alkyl, alkoxy, aminosulfonyl, alkoxycarbonyl, alkylsulfanyl, are optionally substituted with one or more substituents independently selected from the group consisting of fluorine, bromine and chlorine;

$Z^1$ is CH which is substituted with a substituent selected from the group consisting of halogen, nitro, cyano, aminosulfonyl, alkyl, alkoxy, alkoxycarbonyl, alkylsulfanyl, alkylsulfinyl, alkylsulfonyl, arylsulfanyl, arylsulfinyl, arylsulfonyl, heteroaryl, heteroarylsulfanyl, heteroarylsulfinyl, and heteroarylsulfonyl, the alkyl, alkoxy, alkoxycarbonyl, alkylsulfanyl, alkylsulfinyl, alkylsulfonyl, alkylsulfanyl, aryl, arylsulfanyl, arylsulfinyl, arylsulfonyl, heteroaryl, heteroarylsulfanyl, heteroarylsulfinyl, and heteroarylsulfonyl are optionally substituted with one or more substituents independently selected from the group consisting of halogen and alkyl; and the aminosulfonyl is optionally substituted with up to two independently selected alkyl;

$Z^2$ is CH which is substituted with a substituent selected from the group consisting of cyano, halogen, nitro, alkyl, alkoxy, haloalkyl, and haloalkylsulfanyl;

Each of $Z^3$, $Z^4$, and $Z^5$ is CH, the CH is optionally substituted with a substituent selected from the group consisting of halogen, cyano, nitro, alkyl, alkoxy, alkylsulfanyl, haloalkyl, haloalkoxy, and haloalkylsulfanyl.

3. A compound or salt thereof, wherein:
the compound corresponds in structure to Formula (I):

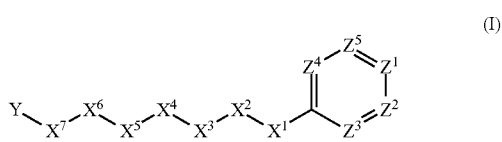

wherein, $X^1$ is —O— or —NH—;

$X^2$ is cyclohexyl;

$X^3$ is —O—;

$X^4$ is —CH$_2$—;

$X^5$ is —C(S)— or —C(O)—;

$X^6$ is a linker selected from the group consisting of

[structures: piperazine-1,4-diyl; 4-piperidinyl-N-; 4-hydroxy-piperidine linker; piperidine-NH linker; and 1,4-diazepane]

$X^7$ is a bond or —NH—;

Y is thiadiazolyl, pyridinyl or, pyrimidinyl, the thiadiazolyl, pyridinyl and pyrimidinyl are optionally substituted with one or more substituents independently selected from the group consisting of chloro, cyano, trifluoromethyl, difluoromethyl, methoxy, trifluoromethoxy, and hydroxy;

$Z^1$ is C-cyano or C-nitro;
$Z^2$ is C-difluoromethyl or C-trifluoromethyl;
$Z^3$, $Z^4$, and $Z^5$ are CH.

4. A compound or salt thereof, wherein:
the compound corresponds in structure to Formula (I):

[structure of Formula (I)]

wherein, $X^1$ is —O— or —NH—;
$X^2$ is cyclohexyl;
$X^3$ is —O—;
$X^4$ is —CH$_2$—;
$X^5$ is —C(S)— or —C(O)—;
$X^6$ is a linker selected from the group consisting of

[structures: piperazine linker; piperidine linker; piperidine-NH; 1,4-diazepane]

$X^7$ is a bond or —NH—;

Y is thiadiazolyl or pyridinyl, the thiadiazolyl and pyridinyl are optionally substituted with one or more substituents R independently selected from the group consisting of chloro, cyano, trifluoromethyl, difluoromethyl, methoxy, and trifluoromethoxy;

$Z^1$ is C-cyano or C-nitro;
$Z^2$ is C-difluoromethyl or C-trifluoromethyl;
$Z^3$, $Z^4$, and $Z^5$ are CH.

5. A pharmaceutical composition, wherein the composition comprises:
a) one or more compounds of the formula (I) or salts thereof, as defined in claim 1; and
b) one or more excipients, and/or one or more active ingredients which differ in structure from component a).

6. A method of treating a disease in an animal, wherein the disease is a helminth infection, wherein the method comprises administering to the animal one or more compounds of the formula (I) or salts thereof, as defined in claim 1.

7. A method as claimed in claim 6, wherein one or more of the helminths are resistant to one or more anthelmintic compounds.

8. A method as claimed in claim 6, wherein the animal is a mammal.

9. A kit, wherein the kit comprises:
a) one or more compounds of the formula (I) or salts thereof, as defined in claim 1, and
b) one or more other components selected from the group consisting of an excipient, an active ingredient, an apparatus for combining the compound of component a) with an excipient or active ingredient, an apparatus for administering the compound of component a) to an animal, and a diagnostic tool.

10. A compound or salt thereof, wherein:
the compound corresponds in structure to:

[chemical structure]

* * * * *